(12) United States Patent
Talingting Pabalan et al.

(10) Patent No.: US 8,969,261 B2
(45) Date of Patent: Mar. 3, 2015

(54) RHEOLOGY MODIFIER COMPOSITIONS AND METHODS OF USE

(75) Inventors: Ruela Talingting Pabalan, Burlington, NJ (US); Nemesio Martinez-Castro, Bristol, PA (US); Subramanian Kesavan, East Windsor, NJ (US); Marie Pierre Labeau, Burlington, NJ (US); Bruno Langlois, Paris (FR)

(73) Assignee: Rhodia Operations, Paris (FR)

( * ) Notice: Subject to any disclaimer, the term of this patent is extended or adjusted under 35 U.S.C. 154(b) by 606 days.

(21) Appl. No.: 13/026,705

(22) Filed: Feb. 14, 2011

(65) Prior Publication Data

US 2011/0256085 A1   Oct. 20, 2011

Related U.S. Application Data

(60) Provisional application No. 61/337,927, filed on Feb. 12, 2010, provisional application No. 61/436,944, filed on Jan. 27, 2011.

(51) Int. Cl.
| | | |
|---|---|---|
| *C11D 3/37* | (2006.01) |
| *C09K 8/80* | (2006.01) |
| *C09D 133/26* | (2006.01) |
| *C09D 133/02* | (2006.01) |
| *C11D 17/00* | (2006.01) |
| *C11D 3/22* | (2006.01) |
| *A61K 8/04* | (2006.01) |
| *A61K 8/73* | (2006.01) |
| *A61K 8/81* | (2006.01) |
| *A61K 8/86* | (2006.01) |
| *A61Q 19/00* | (2006.01) |
| *C08L 1/28* | (2006.01) |
| *C08L 5/00* | (2006.01) |
| *C11D 3/40* | (2006.01) |
| *C08L 5/08* | (2006.01) |

(52) U.S. Cl.
CPC ............... *C11D 3/227* (2013.01); *A61K 8/042* (2013.01); *A61K 8/731* (2013.01); *A61K 8/737* (2013.01); *A61K 8/8147* (2013.01); *A61K 8/8158* (2013.01); *A61K 8/817* (2013.01); *A61K 8/86* (2013.01); *A61Q 19/00* (2013.01); *C08L 1/284* (2013.01); *C08L 5/00* (2013.01); *C09D 133/02* (2013.01); *C11D 3/3765* (2013.01); *C11D 3/3773* (2013.01); *C11D 3/40* (2013.01); *C08L 5/08* (2013.01); *A61K 2800/48* (2013.01); *A61K 2800/5424* (2013.01); *A61K 2800/5426* (2013.01); *A61K 2800/594* (2013.01); *C09K 2208/00* (2013.01)
USPC ........... 507/211; 507/214; 507/215; 507/216; 507/217; 507/219; 507/222; 507/224; 507/225; 507/230; 507/240; 507/248; 507/260; 507/261; 507/263; 507/267; 424/70.13; 424/70.17; 514/772.6; 524/27; 524/521; 524/522

(58) Field of Classification Search
None
See application file for complete search history.

(56) References Cited

U.S. PATENT DOCUMENTS

| | | |
|---|---|---|
| 2,458,888 A | 1/1949 | Rehberg et al. |
| 3,035,004 A | 5/1962 | Glavis |
| 3,652,497 A | 3/1972 | Junas et al. |
| 3,937,283 A | 2/1976 | Blauer et al. |
| 3,976,586 A | 8/1976 | Chakrabarti |
| 4,138,381 A | 2/1979 | Chang et al. |
| 4,146,690 A | 3/1979 | Tago et al. |
| 4,203,858 A | 5/1980 | Chakrabarti |
| 4,351,754 A | 9/1982 | Dupre |
| 4,371,517 A | 2/1983 | Vanlerberghe et al. |
| 4,384,096 A * | 5/1983 | Sonnabend ................... 526/313 |
| 4,432,881 A | 2/1984 | Evani |
| 4,464,524 A * | 8/1984 | Karickhoff .................... 526/313 |
| 4,517,333 A | 5/1985 | Lundberg et al. |
| 4,536,539 A | 8/1985 | Lundberg et al. |
| 4,579,670 A | 4/1986 | Payne |
| 4,591,610 A | 5/1986 | Grollier |
| 4,615,825 A | 10/1986 | Teot et al. |
| 4,620,028 A | 10/1986 | Gorman et al. |
| 4,668,410 A | 5/1987 | Haas et al. |
| 4,683,068 A | 7/1987 | Kucera |

(Continued)

FOREIGN PATENT DOCUMENTS

| | | |
|---|---|---|
| CA | 1298697 | 4/1992 |
| DE | 3822202 A1 | 1/1998 |

(Continued)

OTHER PUBLICATIONS

Grant & Hackh's Chemical Dictionary, p. 217 McGraw-Hill, Inc. (1987).

(Continued)

*Primary Examiner* — John J Figueroa

(57) ABSTRACT

A composition for enhancing fluid viscosity including a mixture of at least one cationic or cationizable polymer and at least one anionic or anionizable (hydrolysable) polymer. The composition has a zeta potential at 25° C. in the range of 0.5 to 100 mV or −0.5 to −100 mV, typically 1 to 60 mV or −1 to −60 mV, or is a precursor convertible at a temperature of 100 to 250° C. to the composition having a zeta potential at 25° C. of 0.5 to 100 mV or −0.5 to −100 mV, typically 1 to 60 mV or −1 to −60 mV. Typically the compositions exhibit salt tolerance and interaction of both polymers at very high temperatures (>300° F.) such that the system exhibits an increase of viscosity at extreme temperatures. The compositions are useful for hydraulic fracturing, enhanced oil recovery, subterranean acidization, personal care as well as home and industrial cleaners.

42 Claims, 19 Drawing Sheets

(56) References Cited

U.S. PATENT DOCUMENTS

| | | | |
|---|---|---|---|
| 4,725,372 A | 2/1988 | Teot et al. | |
| 4,734,099 A | 3/1988 | Cyprien | |
| 4,735,731 A | 4/1988 | Rose et al. | |
| 4,801,671 A * | 1/1989 | Shay et al. | 526/214 |
| 4,804,705 A | 2/1989 | Pum et al. | |
| 4,830,769 A | 5/1989 | O'Lenick et al. | |
| 4,839,166 A | 6/1989 | Grollier et al. | |
| 4,857,226 A | 8/1989 | Drapier et al. | |
| 4,892,916 A | 1/1990 | Hawe et al. | |
| 4,970,260 A | 11/1990 | Lundberg et al. | |
| 5,104,643 A | 4/1992 | Grollier et al. | |
| 5,185,062 A | 2/1993 | Begala | |
| 5,292,843 A * | 3/1994 | Jenkins et al. | 526/318.5 |
| 5,294,693 A | 3/1994 | Egraz et al. | |
| 5,338,406 A | 8/1994 | Smith | |
| 5,415,860 A | 5/1995 | Beucherie et al. | |
| 5,510,306 A | 4/1996 | Murray | |
| 5,551,516 A | 9/1996 | Norman et al. | |
| 5,566,760 A | 10/1996 | Harris | |
| 5,607,680 A | 3/1997 | Brissonnet et al. | |
| 5,629,184 A | 5/1997 | Goldenberg et al. | |
| 5,648,584 A | 7/1997 | Murray | |
| 5,648,585 A | 7/1997 | Murray et al. | |
| 5,674,823 A | 10/1997 | Ricca et al. | |
| 5,686,024 A | 11/1997 | Dahanayake et al. | |
| 5,770,760 A * | 6/1998 | Robinson | 560/221 |
| 5,849,960 A | 12/1998 | Singleton et al. | |
| 5,853,710 A | 12/1998 | Dehan et al. | |
| 5,858,343 A | 1/1999 | Szymczak | |
| 5,874,495 A * | 2/1999 | Robinson | 524/300 |
| 5,902,574 A | 5/1999 | Stoner et al. | |
| 5,902,778 A | 5/1999 | Hartmann et al. | |
| 5,964,295 A | 10/1999 | Brown et al. | |
| 5,979,555 A | 11/1999 | Gadberry et al. | |
| 6,063,857 A * | 5/2000 | Greenblatt et al. | 524/561 |
| 6,077,887 A | 6/2000 | Thuresson | |
| 6,150,222 A | 11/2000 | Gardner et al. | |
| 6,150,312 A | 11/2000 | Puvvada et al. | |
| 6,150,322 A | 11/2000 | Singleton et al. | |
| 6,162,877 A | 12/2000 | Sau | |
| 6,222,077 B1 | 4/2001 | Singleton | |
| 6,232,274 B1 | 5/2001 | Hughes et al. | |
| 6,350,718 B1 | 2/2002 | Frisch | |
| 6,433,061 B1 | 8/2002 | Marchant et al. | |
| 6,482,866 B1 | 11/2002 | Dahayanake et al. | |
| 6,703,352 B2 | 3/2004 | Dahayanake et al. | |
| 6,846,798 B2 | 1/2005 | Joye et al. | |
| 6,897,253 B2 * | 5/2005 | Schmucker-Castner et al. | 524/291 |
| 7,217,752 B2 | 5/2007 | Schmucker-Castner et al. | |
| 7,288,616 B2 * | 10/2007 | Tamareselvy et al. | 526/333 |
| 7,378,479 B2 | 5/2008 | Tamareselvy et al. | |
| 7,727,937 B2 | 6/2010 | Pauls et al. | |
| 7,772,421 B2 | 8/2010 | Yang et al. | |
| 7,789,160 B2 | 9/2010 | Hough et al. | |
| 8,071,674 B2 | 12/2011 | Yang et al. | |
| 2003/0134751 A1 | 7/2003 | Lee et al. | |
| 2003/0180246 A1 | 9/2003 | Frantz et al. | |
| 2003/0190302 A1 | 10/2003 | Frantz et al. | |
| 2004/0092414 A1 | 5/2004 | Clapp et al. | |
| 2004/0247549 A1 | 12/2004 | Lu et al. | |
| 2005/0002892 A1 | 1/2005 | Khan et al. | |
| 2005/0107503 A1 | 5/2005 | Couillet et al. | |
| 2005/0175568 A1 | 8/2005 | Asari et al. | |
| 2006/0040837 A1 | 2/2006 | Frantz et al. | |
| 2006/0135627 A1 | 6/2006 | Frantz et al. | |
| 2006/0135683 A1 | 6/2006 | Adam | |
| 2006/0270563 A1 * | 11/2006 | Yang et al. | 507/119 |
| 2007/0014746 A1 | 1/2007 | Bigorra Llosas et al. | |
| 2008/0095733 A1 | 4/2008 | Griffin et al. | |
| 2008/0113895 A1 | 5/2008 | Tamareselvy et al. | |
| 2009/0010855 A1 * | 1/2009 | Lepilleur et al. | 424/47 |
| 2009/0074695 A1 | 3/2009 | Mahe et al. | |
| 2009/0145607 A1 | 6/2009 | Li | |
| 2009/0192051 A1 | 7/2009 | Carman | |
| 2011/0223125 A1 | 9/2011 | Hough et al. | |
| 2011/0243873 A1 | 10/2011 | Hough et al. | |
| 2012/0116005 A1 | 5/2012 | Yang et al. | |
| 2012/0116040 A1 | 5/2012 | Yang et al. | |
| 2012/0121523 A1 | 5/2012 | Yang et al. | |
| 2012/0123149 A1 | 5/2012 | Yang et al. | |
| 2013/0129647 A1 | 5/2013 | Yang et al. | |

FOREIGN PATENT DOCUMENTS

| | | |
|---|---|---|
| EP | 0362770 A2 | 4/1990 |
| EP | 226097 B1 | 5/1990 |
| EP | 705852 B1 | 12/1998 |
| EP | 1721915 A1 | 11/2006 |
| EP | 1721915 B1 | 5/2008 |
| EP | 1465932 B1 | 7/2008 |
| EP | 1949888 A1 | 7/2008 |
| WO | 8701758 A1 | 3/1987 |
| WO | 98/41505 A1 | 9/1998 |
| WO | 2006130675 A2 | 12/2006 |
| WO | 2008060997 A1 | 5/2008 |

OTHER PUBLICATIONS

Zeta Potential, URL:<en.wikipedia.org/wiki/Zeta_potential>, retrieved from the Internet May 25, 2010.

Optimization of a Visco-Elastic Surfactant VES) Fracturing Fluid for Application in High-Permeability Formations, Sullivan et al, Abstract, 2006, URL:<http://www.onepetro.org/mslib/servlet/onepetropreview?id=SPE-98338-MS&soc=SPE>, retrieved from the Internet Oct. 28, 2010.

QUAB 151, QUAB Chemicals, URL:<http://www.quab.com/products_quab151_general.html>, retrieved from the Internet Oct. 26, 2010.

Zetasizer Nano Technical Note MRK570-02, Measuring Zeta Potential—Laser Doppler Electrophoresis, Malvern Instruments, pp. 1-2 (2010).

Zeta Potential Measurement Using Laser Doppler Electrophoresis (LDE), Malvern Instruments, (2010), URL:<http:// www.malvern.com/LabEng/technology/zeta_potential/zeta_potential_LDE.htm>, retrieved from the Internet Oct. 26, 2010.

Zetasizer Nano Application Note MRK571-01, Measuring Zeta Potential Using Phase Analysis Light Scattering (PALS), Malvern Instruments, pp. 1-3 (2010).

Zetasizer Nano Technical Note MRK654-01, Zeta Potential An Introduction in 30 Minutes, Malvern Instruments , pp. 1-6 (2010).

Zetasizer Nano Application Note MRK512-01, Malvern Instruments, Simplifying the Measurement of Zeta Potential Using M3-PALS, pp. 1-3 (2010).

International Search Report dated Oct. 20, 2011 from PCT/US2011/024721 to Rhodia Operations et al.

C.E. Rehberg, et al., "Preparation and Properties of Monomeric and Polymeric Acrylic Esters of Ether-Alcohols," Journal of Organic Chemistry, vol. 14, 1949, pp. 1094-1098, XP002594784.

Jarchem Industries, Inc., Specialty Monomers, Acrylamides Methacrylates Acrylates others, brochure (2004).

Johansson (Specialty Chemicals Magazine, Nov. 2004: online at URL:<http://www.firp.ula.ve/archivos/material_web_4xx/04_SCM_Johansson.pdf>).

Jarchem, URL:<http://www.jarchem.com/monomers/acrylate_mono.htm>, 2003, retrieved from the Internet via URL: <http://web.archive.org> (WaybackMachine webpage) Aug. 13, 2012.

STN Search Results (Apr. 5, 2012) listed in Notice of References Cited of Office action of Apr. 12, 2012 for U.S. Appl. No. 13/373,162 to Yang et al, filed Nov. 7, 2011.

Office Action of Apr. 12, 2012 for U.S. Appl. No. 13/373,162 to Yang et al, filed Nov. 7, 2011.

Office Action of May 2, 2012 for U.S. Appl. No. 13/317,948 to Yang et al, filed Nov. 1, 2011.

Office Action of Feb. 22, 2013 for U.S. Appl. No. 13/026,686 to Hough et al, filed Feb. 14, 2011.

(56) References Cited

OTHER PUBLICATIONS

Office Action of Aug. 6, 2013 for U.S. Appl. No. 13/026,686 to Hough et al, filed Feb. 14, 2011.
Office Action of Feb. 27, 2013 from U.S. Appl. No. 12/931,903 to Hough et al, filed Feb. 14, 2011.
Notice of Allowance of Apr. 15, 2013 from U.S. Appl. No. 13/317,948 to Yang et al, filed Nov. 1, 2011.
Notice of Allowance of Apr. 19, 2013 from U.S. Appl. No. 13/373,162 to Yang et al, filed Nov. 7, 2011.
Notice of Allowance of Apr. 16, 2013 from U.S. Appl. No. 13/373,154 to Yang et al, filed Nov. 7, 2011.
Notice of Allowance of Apr. 15, 2013 from U.S. Appl. No. 13/373,170 to Yang et al, filed Nov. 7, 2011.
Notice of Allowance of May 14, 2013 from U.S. Appl. No. 13/728,434 to Yang et al, filed Dec. 27, 2012.
Search Report dated Mar. 19, 2014 from Chinese application 201180018270.X, filed Feb. 14, 2011.
The extended European Search Report mailed Oct. 6, 2014 in EP application No. 11742944.9.

\* cited by examiner

RHEOLOGY MODIFIER COMPOSITIONS AND METHODS OF USE

CROSS-REFERENCE TO RELATED APPLICATIONS

This claims the benefit of U.S. provisional patent application No. 61/337,927 filed Feb. 12, 2010 and U.S. provisional patent application No. 61/436,944 filed Jan. 27, 2011, both incorporated herein by reference in their entirety.

FIELD OF THE INVENTION

The present invention relates to a rheology modifier polymer for use in aqueous media. The composition includes a cationic or cationizable polymer and a anionic polymer. The composition has a zeta potential not equal to zero. This invention has many uses, for example treatment fluids for subterranean formations, cleaning compositions and hydrophilized personal care formulation, which can be in the form of a hand or body soap (liquid or bar), lipstick, body wash, makeup remover, skin cleaner, hair conditioner, skin or hair moisturizer.

BACKGROUND

There is an ongoing unresolved need for polymer compositions having improved rheological and aesthetic properties in aqueous media.

Synthetic rheology modifier polymers typically fall within one of four categories: alkali-soluble emulsion ("ASE") polymers, hydrophobically modified alkali-soluble emulsion ("HASE") polymers, hydrophobically modified ethoxylated urethane ("HEUR") polymers, and hydrophobically modified nonionic polyol ("HNP") polymers. HASE is typically a low viscosity emulsion at low pHs. To increase viscosity, the emulsion is neutralized to pH above 7, preferably above 8. When it is neutralized, HASE swells and viscosifies. The hydrophobic modifications, for example, the terpene alkoxylate components acting like stickers and the acrylate-based extended hydrophilic brushes are responsible for creating the swollen 3-D structure as viscous gels. FIG. 1 shows an idealized diagram of the swelling of HASE polymer at alkaline pH. In particular FIG. 1 shows a low viscosity emulsion 2 containing a HASE latex particle 4 reacted with base forms a viscous solution 6 having a HASE 3D Network 8.

HASE and ASE polymers, see, for example those described in, U.S. Pat. No. 3,035,004, U.S. Pat. No. 5,292,843, U.S. Pat. No. 6,897,253, U.S. Pat. No. 7,288,616, U.S. Pat. No. 7,378,479, and US Patent Publication No. 2006/0270563, have each been widely used as rheology modifiers in aqueous systems.

However, there is a continuing need to compositions with improved resistance to high salt concentrations, and improved resistance to the potentially high temperatures involved in some of their uses.

For example, there is a need for improved polymer compositions for use in a variety of methods for recovering natural gas and crude oil from subterranean formations. One such technique is hydraulic fracturing of the subterranean formation conducted to increase oil and/or gas production. Fracturing is caused by injecting a viscous fracturing fluid or a foam at a high pressure (hereinafter injection pressure) into the well to form a fracture. As the fracture is formed, the particulate material, referred to as a "propping agent" or "proppant" is placed in the formation to maintain the fracture in a propped condition when the injection pressure is released. Coated and/or uncoated particles are often used as proppants to keep open fractures imposed by hydraulic fracturing upon a subterranean formation, e.g., an oil or gas bearing strata. Particles typically used to prop fractures generally comprise sand or sintered ceramic particles as the fracture forms, the proppants are carried into the fracture by suspending them in additional fluid or foam to fill the fracture with a slurry of proppant in the fluid or foam. Upon release of the pressure, the proppants form a pack that serves to hold open the fractures. Thus, the proppants increase production of oil and/or gas by providing a conductive channel in the formation. The degree of stimulation afforded by the hydraulic fracture treatment is largely dependent upon formation parameters, the fracture's permeability and the fracture's propped width.

In oilfield fracturing, there is a need for a proppant carrier that is a viscoelastic medium that can prevent proppants or sand from settling while being position in the fractures. Two common chemistries are in the market: natural polymers (guars, etc), and visco-elastic surfactant systems (VES). Guar and VES are existing proppant carriers used in fracturing fluids. Guar is a polysaccharide and is being used for many decades. VES in fracturing has been used for about a decade. Visco-Elastic Surfactant (VES) fluids are polymer-free fluids that generate viscosities suitable for fracturing operations without the use of polymer additives. Viscosity of a VES fluid is created by self-assembly of surfactant molecules in an aqueous solution. The use of synthetic polymers, like polyacrylamides, polyacrylates and other copolymers by themselves or with combination with VES or guar and/or the use of various crosslinkers is more recent.

US Patent Application Publication No. 2009/0145607 to Li et al entitled High Temperature Fracturing Fluids and Method of Use discloses a treatment fluid for treating a subterranean formation comprising: an aqueous solution of a polysaccharide, a polyacrylamide, a crosslinking agent, and less than 0.1% by weight of any clay component, wherein the polyacrylamide is present in an amount of from about 0.01 percent to about 1 percent by weight of the fluid. In an embodiment the polysaccharide is selected from carboxymethylhydroxypropyl guar (CMHPG), hydroxypropyl guar, guar and combinations of these.

US Patent Application Publication No. 2006/0270563 to Yang et al. discloses a HASE copolymer also known as a pH responsive polymer. Yang et al also discloses a hydraulic fracturing composition comprising water and this pH responsive polymer and a proppant.

A number of polymer-free aqueous fracturing fluids are based on viscoelastic surfactants. The principal advantages of viscoelastic surfactant fluids are ease of preparation, minimal formation damage and high retained permeability in the proppant pack. Viscoelastic surfactant fluids are disclosed, for example, in U.S. Pat. Nos. 4,615,825, 4,725,372, 4,735,731, CA-1298697, U.S. Pat. Nos. 5,551,516, 5,964,295, 5,979,555 and 6,232,274. One well-known polymer-free aqueous fracturing fluid comprising a viscoelastic surfactant, which has been commercialized by the company group Schlumberger under the trademark ClearFRAC, and a mixture of a quaternary ammonium salt, the N-erucyl-N,N-bis(2-hydroxyethyl)-N-methyl ammonium chloride, with isopropanol and brine, the brine preferably including 3% by weight of ammonium chloride and 4% by weight of potassium chloride.

Published PCT application WO 87/01758 entitled "Hydraulic Fracturing Process and Compositions" discloses fracturing processes which use aqueous hydraulic fracturing fluids. The fluids comprise: (a) an aqueous medium, and (b) a thickening amount of a thickener composition comprising (i) a water-soluble or water-dispersible interpolymer having pendant hydrophobic groups chemically bonded thereto, (ii) a nonionic surfactant having a hydrophobic group(s) that is capable of associating with the hydrophobic groups on said organic polymer, and (iii) a water-soluble electrolyte. Additionally, the fluids preferably contain a stabilizing amount of a thiosulfate salt. As an example, an interpolymer of acrylamide and dodecyl acrylate was used in combination with a nonionic surfactant (HLB of from 10 to 14) to thicken a dilute aqueous solution of KCl and sodium thiosulfate; the aqueous solution had excellent properties for use as a high temperature hydraulic fracturing fluid.

U.S. Pat. No. 4,432,881 entitled "Water-Dispersible Hydrophobic Thickening Agent" discloses an aqueous liquid medium having increased low shear viscosity as provided by dispersing into the aqueous medium (1) a water-soluble polymer having pendant hydrophobic groups, e.g., an acrylamide dodecyl acrylate copolymer, and (2) a water-dispersible surfactant, e.g., sodium oleate, or dodecyl polyethyleneoxy glycol monoether. The thickened aqueous medium is suitably employed in applications requiring viscous liquids which retain their viscosity when subjected to shear, heat or high electrolyte (salt) concentrations. Such applications include uses in oil recovery processes, as fluid mobility control agents, fracturing fluids and drilling muds, as well as hydraulic fluids and lubricants in many applications.

Also, U.S. Pat. No. 5,566,760 entitled "Method of Using a Foamed Fracturing Fluid" discloses a fracturing fluid comprising surfactants and hydrophobically-modified polymers. In these fluids, surfactant molecules form the interface between gas bubbles and the polymer molecules that form a polymeric network similar to those of the pure polymeric fluids. Still, there is no mention of viscoelastic surfactants or of the responsiveness of the fluids to hydrocarbons.

In addition to fracturing, other techniques may be employed to further improve hydrocarbon recovery from subterranean formations. There is also a need for improved treatment fluids for "enhanced oil recovery" techniques for treating subterranean formations after the oil has been produced from a formation by pressure depletion (primary recover). In pressure depletion, the differential pressure between the formation and a production well or wells forces the oil contained within the formation toward a production well where it can be recovered. Typically, up to about 35 percent of the oil initially contained in a formation can be recovered using pressure depletion. This leaves a large quantity of oil within the formation. Additionally, some formations contain oil which is too viscous to be efficiently recovered from the formation using pressure depletion methods. Because of the need to recover a larger percentage of the oil from a formation, methods have been developed to recover oil which could not be recovered using only pressure depletion techniques or secondary recovery techniques. These methods are typically referred to as "enhanced oil recovery techniques" (EOR).

U.S. Pat. No. 7,727,937 to Pauls et al, incorporated herein by reference in its entirety discloses acidic treatment fluids used in industrial and/or subterranean operations, and more particularly, acidic treatment fluids comprising clarified xanthan gelling agents, and methods of use in industrial and/or subterranean operations, are provided. In one embodiment, the acidic treatment fluids comprise an aqueous base fluid, an acid, and a gelling agent comprising clarified xanthan.

U.S. Pat. No. 7,789,160 to Hough et al, incorporated herein by reference in its entirety discloses an aqueous fluid useful for the recovery of crude oil from a subterranean formation, which includes a composition including a mixture of water, a water soluble block copolymer, an inorganic salt and at least one member of the group of a nonionic surfactant having an HLB of less than 12, and methods for using same.

U.S. Patent Application Publication 2003/0134751 discloses addition of polymers to a viscoelastic surfactant base system allows adjusting the rheological properties of the base fluid. The polymer can perform different functions (breaker, viscosity enhancer, or viscosity recovery enhancer) depending upon its molecular weight and concentration in the fluid. The methods and compositions are presented for adjusting the viscosity of viscoelastic surfactant fluids based on anionic, cationic, nonionic and zwitterionic surfactants.

U.S. Patent Application Publication 2005/0107503 A1 describes an aqueous viscoelastic fracturing fluid for use in the recovery of hydrocarbons. The fluid comprises a viscoelastic surfactant and a hydrophobically modified polymer. The viscoelastic surfactant is usually ionic. It may be cationic, anionic or zwitterionic depending on the charge of its head group.

Among the more promising of the methods being used today is an enhanced oil recovery process referred to as a surfactant flood. An aqueous fluid containing surfactant is injected into an oil rich formation to displace oil from the formation and the displaced oil is then recovered.

Another promising method being used today is an enhanced oil recovery process referred to as chemical flooding which generally covers the use of polymer and/or surfactant slugs. In polymer flooding, a polymer solution is injected to displace oil toward producing wells. The polymer solution is designed to develop a favorable mobility ratio between the injected polymer solution and the oil/water bank being displaced ahead of the polymer. However, the use of polymer is not always satisfactory as many polymer solutions are sensitive to brine type and concentration which can affect the apparent viscosity of the solution. In surfactant flooding, an aqueous solution containing surfactant is injected into the oil rich formation. Residual oil drops are deformed as a result of low Interfacial Tension provided by surfactant solution and drops are displaced through the pore throats and displaced oil is the recovered.

It would be desirable to provide high temperature stable fracturing fluids and EOR fluids for subterranean formations, such as natural gas and/or oil field.

Also there is a need to enhance viscosity to improve personal care compositions and cleaning compositions for home and industry. In home and personal care there is a need for stable combinations of polyanionic and cationic polymers for personal care products 2-in-1 shampoo and conditioner. For home care it is in detergent and softener in one.

SUMMARY OF THE INVENTION

Unexpectedly, the inventors have discovered a composition for enhancing viscosity of a fluid comprising a mixture of cationic or cationizable polysaccharide or synthetic polymers, and blends thereof, and anionic polymers, and blends thereof, where the mixture exhibits viscosities higher than individual components.

In an embodiment the invention is a composition for enhancing viscosity of a fluid comprising a mixture of:

(A) at least a first polymer having a weight average molecular weight of 35,000 to 10,000,000, more typically in the range of about 200,000 to about 3,000,000 grams/mol, selected from at least one member of the group consisting of (1) a cationic polysaccharide with quarternized amino functional groups and cationic charge density of 0.3 to 2, typically 0.4 to 1.7 milliequivalents/gram, (2) cationizable polysaccharides with primary amino groups and which are at least partially cationizable to a cationic polymer having a cationic charge density of 0.3 to 2, typically 0.4 to 1.7 milliequivalents/gram at a temperature of 100 to 250° C., and (3) cationizable polymers with at least one member of the group consisting of primary, secondary and tertiary amino groups and which at least partially cationizable to a cationic polymer having a cationic charge density of 0.3 to 2, typically 0.4 to 1.7 milliequivalents/gram at a temperature of 100 to 250° C.;

(B) at least a second polymer having a weight average molecular weight of 30,000 g/mol to 10,000,000 g/mol, for example, 30,000 to 500,000 g/mol, more typically 50,000 g/mol to 500,000 g/mol, selected from the group consisting of:

(1) anionic polymers selected from the group consisting of polyacrylic acid, polyacrylamide and acrylate copolymer (for example, HASE; copolymers of alkylacrylate, methylacrylate, methylmethacrylate and/or ethylacrylates with acrylic acid and/or acrylamide), the at least one anionic polymer, and having an anionic charge density of 0.1 to 20 milliequivalents/gram, typically 0.4 to 15 milliequivalents/gram, or typically 1 to 15 milliequivalents/gram, or typically 1 to 10 milliequivalents/gram, or typically 1 to 5 milliequivalents/gram, or typically 9 to 15 milliequivalents/gram, wherein the anionic polymer has functional groups selected from the group consisting of carboxylate, sulfate, sulfonate, phosphate or phosphonate, and (2) at least one hydrolysable polymer selected from the group consisting of polyalkylacrylate, polyacrylamide and copolymers of polyalkylacrylate and polyacrylamide, the at least one hydrolysable polymer having a weight average molecular weight of 30,000 g/mol to 10,000,000 g/mol, and which is at least partially hydrolyzable to an anionic polymer having an anionic charge density of 0.1 to 20 milliequivalents/gram, typically 0.4 to 15 milliequivalents/gram, or typically 1 to 15 milliequivalents/gram, or typically 1 to 10 milliequivalents/gram, or typically 1 to 5 milliequivalents/gram, or typically 9 to 15 milliequivalents/gram at a temperature of 100 to 250° C., wherein the hydrolysable polymer optionally has functional groups selected from the group consisting of sulfate, sulfonate, phosphate or phosphonate;

wherein the composition has a zeta potential at 25° C. in the range of 0.5 to 100 mV or −0.5 to −100 mV, typically 1 to 60 mV or −1 to −60 mV, also typically 14 to 50 mV or −14 to −50 mV, also typically 30 to 50 mV or −30 to −50 mV or is a precursor convertible at a temperature of 100 to 250° C. to the composition having a zeta potential at 25° C. of 0.5 to 100 mV or −0.5 to −100 mV, typically 1 to 60 mV or −1 to −60 mV, also typically 14 to 50 mV or −14 to −50 mV, also typically 30 to 50 mV or −30 to −50 mV.

In the present invention the zeta potential of the composition at 25° C. is not zero. Thus, zeta potential ranges are typically specified by a positive charge range and a negative charge range. In the remainder of the specification ranges such as 0.5 to 100 mV and −0.5 to −100 mV will be written as +/−0.5 to +/−100 mV. This terminology excludes, for example, the range from −0.4 to +0.4 mV. Typically the cationizable polysaccharides and cationizable polymers cationize at a pH of 7 to 11. Typically the suitable $pK_a$ for cationizing also ranges from 7 to 11.

The anionic polymers are typically carboxylate-containing, sulfate-containing, sulfonate-containing, phosphonate-containing, phosphate-containing, or neutral but hydrolysable to gain negative charges, such as but not limited to the above-mentioned polyacrylamides. Typical anionic polymers contain carboxylate functionalities from acrylic acid, methacrylic acid, itaconic acid, fumaric acid, crotonic acid, and maleic acid.

Typical acid monomers to provide the carboxylate-containing, sulfate-containing, sulfonate-containing, phosphonate-containing, or phosphate-containing functional groups include, for example, ethylenically unsaturated carboxylic acid monomers, such as acrylic acid and methacrylic acid, ethylenically unsaturated dicarboxylic acid monomers, such ac maleic acid and fumaric acid, ethylenically unsaturated alkyl monoesters of dicarboxylic acid monomers, such as butyl methyl maleate, ethylenically unsaturated sulphonic acid monomers, such as vinyl sulfonic acid 2-acrylamido-2-methylpropane sulfonic acid, and styrene sulfonic acid, and ethylenically unsaturated phosphonic acid monomers, such as vinyl phosphonic acid and allyl phosphonic acid, salts of any thereof, and mixtures of any thereof. Alternatively, corresponding ethylenically unsaturated anhydride or acid chloride monomers, such as maleic anhydride, may be used and subsequently hydrolyzed to give a pendant moiety having two acid groups.

The anionic polymers and cationic polymers are typically synthesized by emulsion or latex polymerization, solution polymerization, or bulk polymerization.

The composition may further comprise a monovalent salt concentration of 0.1 to 25 wt. %, e.g., 2 to 5 wt. %, on a wet (aqueous) basis and/or a divalent salt concentration of 0.01 to 25 wt. %, e.g., 2 to 5 wt. %. For example, the composition may further comprise a monovalent salt concentration of 2 to 25 wt. % on a wet (aqueous) basis and/or a divalent salt concentration of 2 to 25 wt. %, wherein the composition is a first composition having no phase separation at 20° C., whereas a second composition having the same composition as the first composition but having an absence of the cationic polymer typically can have phase separation at 20° C., particularly in the presence of divalent salt. For example, the composition may comprise calcium chloride.

The anionic polymer is mixed with cationic polymer for high salt (e.g., brine) and high temperatures tolerance. Anionic polymers for example, acrylates/methacrylates are normally intolerant to salts. It is theorized the cationic polymer masks most or all of anionic polymer, e.g., acrylates, to create a more stable association in the presence of monovalent and divalent salts. (See FIG. 2).

In addition to salt tolerance, there is surprising interaction of both polymers at very high temperatures (>300° F.). The system exhibits an increase of viscosity at these extreme temperatures.

Typically the composition has a viscosity of at least 50 cp at $100 \sec^{-1}$ measured by Brookfield rheometer at a temperature of 350° F. This is preferable for use in subterranean formations.

As reflected by the Zeta Potential not equal to zero, the composition satisfies Equation I:

$$(AW \times ACD) - (CW \times CCD) \text{ is not equal to } 0 \qquad \text{I.}$$

In Equation I AW is weight of the anionic polymer, ACD is charge density of the anionic polymer, CW is weight of the cationic polymer, and CDD is charge density of the cationic polymer.

In other words, for example, for the overall composition, $[COO] + [^+NH_x]$ is not equal to 0.

Moreover, in the composition the typical ratio of anionic polymer to cationic polymer is 1 to 100:100 to 1.

This composition which includes an anionic polymer and a cationic polymer may be used, for example, in compositions for fracturing a subterranean formation, enhanced oil recovery, personal care and industrial and home cleaning products.

The composition typically comprises 0.1 to 15 or 0.5 to 10, more typically 1 to 5 parts by weight anionic polymer and 0.1 to 15 or 0.5 to 10, more typically 1 to 5 parts by weight cationic polymer.

The anionic polymer of a typical composition includes a HASE polymer. The HASE polymer includes (a) one or more first monomeric units, each independently including at least one bicycloheptyl-polyether, bicycloheptenyl-polyether or branched ($C_5$-$C_{50}$)alkyl-polyether group per monomeric unit, wherein the bicycloheptyl-polyether or bicycloheptenyl-polyether group may optionally be substituted on one or more ring carbon atoms by one or two ($C_1$-$C_6$)alkyl groups per carbon atom, and (b) optionally one or more second monomeric units, each independently including at least one pendant linear or branched ($C_5$-$C_{50}$)alkyl-polyether group per monomeric unit, provided that the first and second monomeric units cannot both include a branched ($C_5$-$C_{50}$)alkyl-polyether group, and has a weight average molecular weight of greater than or equal to about 30,000 grams per mole, for example 30,000 to 10,000,000 grams per mole.

DETAILED DESCRIPTION OF THE INVENTION

Figure 1:
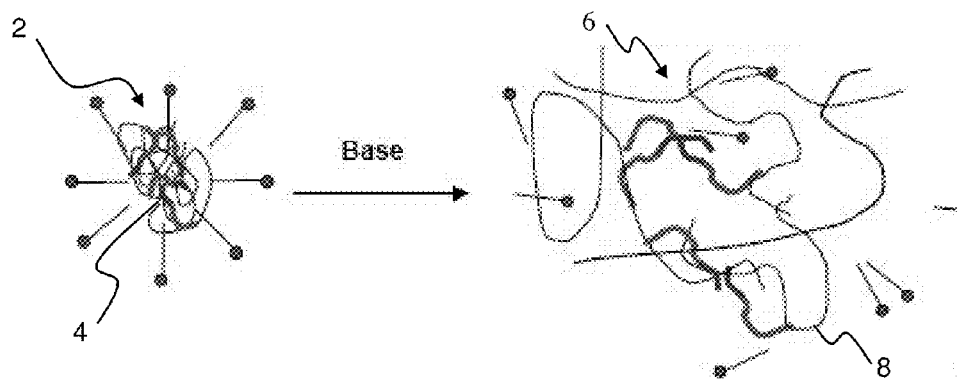
FIG. 1 shows an idealized diagram of the swelling of HASE polymer.
Figure 2:
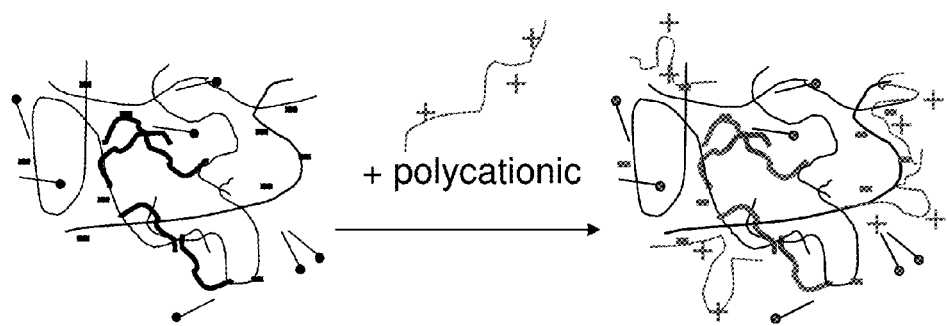
FIG. 2 shows an idealized diagram of using cationic polymers to mask most or all of the acrylates of a HASE polymer.

As used herein, the term "alkyl" means a monovalent straight or branched saturated hydrocarbon radical, more typically, a monovalent straight or branched saturated ($C_1$-$C_{40}$) hydrocarbon radical, such as, for example, methyl, ethyl, n-propyl, isopropyl, n-butyl, isobutyl, tert-butyl, hexyl, octyl, hexadecyl, octadecyl, eicosyl, behenyl, tricontyl, and tertacontyl.

As used herein, the term "alkoxyl" means an oxy radical that is substituted with an alkyl group, such as for example, methoxyl, ethoxyl, propoxyl, isopropoxyl, or butoxyl, which may optionally be further substituted on one or more of the carbon atoms of the radical.

As used herein, the term "alkoxyalkyl" means an alkyl radical that is substituted with one or more alkoxy substituents, more typically a ($C_1$-$C_{22}$)alkyloxy-($C_1$-$C_6$)alkyl radical, such as methoxymethyl, and ethoxybutyl.

As used herein, the term "alkenyl" means an unsaturated straight or branched hydrocarbon radical, more typically an unsaturated straight, branched, ($C_2$-$C_{22}$) hydrocarbon radical, that contains one or more carbon-carbon double bonds, such as, for example, ethenyl, n-propenyl, iso-propenyl.

As used herein, terms "aqueous medium" and "aqueous media" are used herein to refer to any liquid medium of which water is a major component. Thus, the term includes water per se as well as aqueous solutions and dispersions.

As used herein, the term "aryl" means a monovalent unsaturated hydrocarbon radical containing one or more six-membered carbon rings in which the unsaturation may be represented by three conjugated double bonds, which may be substituted one or more of carbons of the ring with hydroxy, alkyl, alkoxyl, alkenyl, halo, haloalkyl, monocyclic aryl, or amino, such as, for example, phenyl, methylphenyl, methoxyphenyl, dimethylphenyl, trimethylphenyl, chlorophenyl, trichloromethylphenyl, triisobutyl phenyl, tristyrylphenyl, and aminophenyl.

As used herein, the term "aralkyl" means an alkyl group substituted with one or more aryl groups, more typically a $(C_1-C_{18})$alkyl substituted with one or more $(C_6-C_{14})$aryl substituents, such as, for example, phenylmethyl, phenylethyl, and triphenylmethyl.

As used herein, the term "aryloxy" means an oxy radical substituted with an aryl group, such as for example, phenyloxy, methylphenyl oxy, isopropylmethylphenyloxy.

The "bicyclo[d.e.f]" notation is used herein in reference to bicycloheptyl and bicycloheptenyl ring systems in accordance with the von Baeyer system for naming polycyclic compounds, wherein a bicyclic system is named by the prefix "bicyclo-" to indicate number of rings in the system, followed by a series of three arabic numbers, listed in descending numerical order, separated by full stops, and enclosed in square brackets, to indicate the respective number of skeletal atoms in each acyclic chain connecting the two common atoms (the "bridgehead atoms"), excluding the bridgehead atoms. A bridgehead atom is any skeletal atom of the ring system bonded to three or more skeletal atoms (excluding hydrogen). A bicyclic system (which comprises the main ring and main bridge only) is named by: the prefix bicyclo—(indicating the number of rings); numbers indicating the bridge lengths (i.e. number of skeletal atoms excluding the bridgehead atoms) separated by full stops and placed in square brackets. The three numbers are cited in decreasing order of size (e.g.[3.2.1]); the name of the hydrocarbon indicating the total number of skeletal atoms. For example, bicyclo[3.2.1]octane is the name for the structure of Formula I.

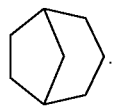

I

As used herein, the terminology "$(C_x-C_y)$" in reference to an organic group, wherein x and y are each integers, indicates that the group may contain from x carbon atoms to y carbon atoms per group.

As used herein, the term "cycloalkenyl" means an unsaturated hydrocarbon radical, typically an unsaturated $(C_5-C_{22})$ hydrocarbon radical, that contains one or more cyclic alkenyl rings and which may optionally be substituted on one or more carbon atoms of the ring with one or two $(C_1-C_6)$alkyl groups per carbon atom, such as cyclohexenyl, cycloheptenyl, and "bicycloalkenyl" means a cycloalkenyl ring system that comprises two condensed rings, such as bicycloheptenyl.

As used herein, the term "cycloalkyl" means a saturated hydrocarbon radical, more typically a saturated $(C_5-C_{22})$ hydrocarbon radical, that includes one or more cyclic alkyl rings, which may optionally be substituted on one or more carbon atoms of the ring with one or two $(C_1-C_6)$alkyl groups per carbon atom, such as, for example, cyclopentyl, cycloheptyl, cyclooctyl, and "bicyloalkyl" means a cycloalkyl ring system that comprises two condensed rings, such as bicycloheptyl.

As used herein, an indication that a composition is "free" of a specific material means the composition contains no measurable amount of that material.

As used herein, the term "heterocyclic" means a saturated or unsaturated organic radical that comprises a ring or condensed ring system, typically comprising from 4 to 16 ring atoms per ring or ring system, wherein such ring atoms comprise carbon atoms and at least one heteroatom, such as for example, O, N, S, or P per ring or ring system, which may optionally be substituted on one or more of the ring atoms, such as, for example, thiophenyl, benzothiphenyl, thianthrenyl, pyranyl, benzofuranyl, xanthenyl, pyrrolidinyl, pyrrolyl, pyradinyl, pyrazinyl, pyrimadinyl, pyridazinyl, indolyl, quinonyl, carbazolyl, phenathrolinyl, thiazolyl, oxazolyl, phenoxazinyl, or phosphabenzenyl.

As used herein, the term "hydroxyalkyl" means an alkyl radical, more typically a $(C_1-C_{22})$alkyl radical, that is substituted with one or more hydroxyl groups, such as for example, hydroxymethyl, hydroxyethyl, hydroxypropyl, and hydroxydecyl.

As used herein, the terminology "hydrophobic surface" means a surface that exhibits a tendency to repel water and to thus resist being wetted by water, as evidenced by a water contact angle of greater than or equal to 70°, more typically greater than or equal to 90°, and/or a surface free energy of less than or equal to about 40 dynes/cm.

As used herein, the terminology "hydrophilic surface" means a surface that exhibits an affinity for water and to thus be wettable by water, as evidenced by a water contact angle of less than 70°, more typically less than 60° and/or a surface energy of greater than about 40 dynes/cm, more typically greater than or equal to about 50 dynes/cm.

As used herein in reference to a hydrophobic surface, the term "hydrophilizing" means rendering such surface more hydrophilic and thus less hydrophobic, as indicated by a decreased water contact angle. One indication of increased hydrophilicity of a treated hydrophobic surface is a decreased water contact angle with a treated surface compared to the water contact angle with an untreated surface.

As used herein the term "(meth)acrylate" refers collectively and alternatively to the acrylate and methacrylate and the term "(meth)acrylamide" refers collectively and alternatively to the acrylamide and methacrylamide, so that, for example, "butyl (meth)acrylate" means butyl acrylate and/or butyl methacrylate.

As used herein, "molecular weight" in reference to a polymer or any portion thereof, means to the weight-average molecular weight ("$M_w$") of said polymer or portion, wherein $M_w$ of a polymer is a value measured by gel permeation chromatography with an aqueous eluent or an organic eluent (for example dimethylacetamide, dimethylformamide, and the like), depending on the composition of the polymer, light scattering (DLS or alternatively MALLS), viscometry, or a number of other standard techniques and $M_w$ of a portion of a polymer is a value calculated according to known techniques from the amounts of monomers, polymers, initiators and/or transfer agents used to make the said portion.

As used herein, the indication that a radical may be "optionally substituted" or "optionally further substituted" means, in general, that is unless further limited, either explicitly or by the context of such reference, that such radical may be substituted with one or more inorganic or organic substituent groups, such as, for example, alkyl, alkenyl, aryl, aralkyl, alkaryl, a hetero atom, or heterocyclyl, or with one or more functional groups that are capable of coordinating to metal ions, such as hydroxyl, carbonyl, carboxyl, amino, imino, amido, phosphonic acid, sulphonic acid, or arsenate, or inorganic and organic esters thereof, such as, for example, sulphate or phosphate, or salts thereof.

As used herein, "parts by weight" or "pbw" in reference to a named compound refers to the amount of the named compound, exclusive, for example, of any associated solvent. In some instances, the trade name of the commercial source of the compound is also given, typically in parentheses. For example, a reference to "10 pbw cocoamidopropylbetaine ("CAPB", as MIRATAINE BET C-30)" means 10 pbw of the actual betaine compound, added in the form of a commercially available aqueous solution of the betaine compound having the trade name "MIRATAINE BET C-30", and exclusive of the water contained in the aqueous solution.

As used herein, an indication that a composition is "substantially free" of a specific material, means the composition contains no more than an insubstantial amount of that material, and an "insubstantial amount" means an amount that does not measurably affect the desired properties of the composition.

Surface energy is estimated using the Young equation:

$$\cos(\theta) * \gamma_{lv} = \gamma_{sv} - \gamma_{sl}$$

with the contact angle $\theta$ the interfacial energy $\gamma_{sv}$ between the solid and the vapor phase, the interfacial energy $\gamma_{sl}$ between the solid and the liquid phase, and the interfacial energy $\gamma_{lv}$ between the liquid and the vapor phase, and $\gamma_{sv}$ represents the surface energy of the solid.

As used herein, the term "surfactant" means a compound that reduces surface tension when dissolved in water.

As used herein in reference to a substrate, the terminology "water contact angle" means the contact angle exhibited by a droplet of water on the surface as measured by a conventional image analysis method, that is, by disposing a droplet of water on the surface, typically a substantially flat surface, at 25° C., photographing the droplet, and measuring the contact angle shown in the photographic image.

Zeta Potential

As used herein Zeta potential is a scientific term for electrokinetic potential in colloidal systems. In the colloidal chemistry literature, it is usually denoted using the Greek letter zeta, hence ζ-potential.

Zeta potential is a measure of the magnitude of the repulsion or attraction between particles. Zeta potential is an index of the magnitude of interaction between colloidal particles and measurements of zeta potential are used to access the stability of colloidal systems.

Most colloidal dispersions in aqueous media carry a surface charge. Dissociation of acidic groups on the surface of a particle will give rise to a negatively charged surface. In contrast, a basic surface will take a positive charge. The magnitude of the surface charge depends on the acidic or basic strengths of the surface groups and the pH of the solution. The surface charge can be reduced to zero by suppressing the surface ionization by decreasing the pH in the case of negatively charged particles or increasing the pH in the case of positively charged particles. Surfactant ions may be specifically adsorbed on the surface of a particle leading, in the case of cationic surfactants, to a positively charged surface and, in the case of anionic surfactants, to a negatively charged surface. *Zeta Potential an Introduction in* 30 *Minutes*, Zetasizer Nano Series Technical Note, p. 3 (prior to September 2010). The development of a net charge at the particle surface affecs the distribution of ions in the surrounding interfacial region, resulting in an increased concentration of counter ions, ions of opposite charge to that of the particle, close to the surface. Thus, an electrical double layer exists round each particle. The liquid layer surrounding the particle exits as two parts; an inner region (Stern layer) where the ions are strongly bound and an outer (difused) region where they are less firmly associated. Within the diffuse layer there is a notional boundary inside which the ions and particles form a stable entity. When a particle moves (e.g., due to gravity), ions within the boundry move with it. Those ions beyond the boundary stay with the bulk dispersant. The potential at the boundary (surface of hydrodynamic shear) is the zeta potential.

From a theoretical viewpoint, zeta potential is electric potential in the interfacial double layer (DL) at the location of the slipping plane versus a point in the bulk fluid away from the interface. In other words, zeta potential is the potential difference between the dispersion medium and the stationary layer of fluid attached to the dispersed particle.

Zeta potential is widely used for quantification of the magnitude of the electrical charge at the double layer. Zeta potential should not be confused with electrode potential or electrochemical potential (because electrochemical reactions are generally not involved in the development of zeta potential).

In aqueous media, the pH of the sample affects its zeta potential. For example, if alkali is added to a suspension with a negative zeta potential the particles tend to acquire more negative charge. If sufficient acid is added to the suspension then a point will be reached where the charge will be neutralized. Further addition of acid will cause a buildup of positive charge.

Zeta potential is not measurable directly but it can be calculated using theoretical models and an experimentally-determined electrophoretic mobility or dynamic electrophoretic mobility. Electrokinetic phenomena and electroacoustic phenomena are the usual sources of data for calculation of zeta potential. However, for purposes of the present specification zeta potential is calculated using electrokinetic phemomena, in particular electrophoresis. Electrophoresis is used for estimating zeta potential of particulates, whereas streaming potential/current is used for porous bodies and flat surfaces.

Electrophoresis is the movement of a charged particle relative to the liquid it is suspended in under the influence of an applied electric field. When an electric field is applied across an electrolyte, charged particles suspended in the electrolyte are attracted towards the electrode of opposite charge. Viscous forces acting on the particles tend to oppose this movement. When equilibrium is reached between these two opposing forces, the particles move with constant velocity.

The velocity is dependent on the strength of electric field or voltage gradient, the dielectric contant of the medium, the viscosity of the medium and the zeta potential.

The velocity of the particle in a unit electric field is referred to as its electrophoretic mobility. Zeta potential is related to the electrophoretic mobility by the Henry equation: $-UE = (2 \in zf(\kappa a))/3n$ where UE=electrophoretic mobility, z=zeta potential, $\in$=dielectric constant, n=viscosity and $f(\kappa a)$=Henry's function. The units of k, termed the Debye length, are reciprocal length and $\kappa-1$ is often taken as a measure of the "thickness" of the electrical double layer. The parameter 'a' refers to the radius of the particle and therefore κa measures the ratio of the particle radius to electrical double layer thickness. Electrophoretic determinations of zeta potential are most commonly made in aqueous media and moderate electrolyte concentration. F(κa) in this case is 1.5, and this is referred to as the Smoluchowski approximation.

Therefore calculation of zeta potential from the mobility is straightforward for systems that fit the Smoluchowski model, i.e. particles larger than about 0.2 microns dispersed in electrolytes containing more that 10-3 molar salt. For small particles in low dielectric constant media (eg non-aqueous media), f(κa) becomes 1.0 and allows an equally simple calculation. This is referred to as the Huckel approximation.

Thus, particles within the dispersion with a zeta potential will migrate toward the electrode of opposite charge with a velocity proportional to the magnitude of the zeta potential.

The essence of a classical microelectrophoresis system is a capillary cell with electrodes at either end to which a potential is applied. Particles move towards the electrode, their velocity is measured and expressed in unit field strength as their mobility. Early methods involved the process of directly observing individual particles using ultra-microscope techniques and manually tracking their progress over a measured distance. This procedure, although still being used by many groups world wide, suffers from several disadvantages, not least that of the strenuous effort required to make a measurement, particularly with small or poorly scattering particles.

More typically, this velocity is measured using the technique of the Laser Doppler Anemometer. The frequency shift or phase shift of an incident laser beam caused by these moving particles is measured as the particle mobility, and this mobility is converted to the zeta potential by inputting the dispersant viscosity and dielectric permittivity, and the application of the Smoluchowski theories.

The ZETASIZER NANO Series available from Malvern Instruments, United Kingdom uses a combination of laser Doppler velocimetry and phase analysis light scattering (PALS) in a patented technique called M3-PALS to measure particle electrophoretic mobility.

A zeta potential measurement system of the ZETASIZER NANO Series available from Malvern Instruments comprises six main components. Firstly, a laser is used to provide a light source to illuminate the particles within the sample. For zeta potential measurements, this light source is split to provide an incident and reference beam. The incident laser beam passes through the centre of the sample cell, and the scattered light at an angle of about 13° is detected. When an electric field is applied to the cell, any particles moving through the measurement volume will cause the intensity of light detected to fluctuate with a frequency proportional to the particle speed and this information is passed to a digital signal processor and then to a computer. The ZETASIZER NANO software produces a frequency spectrum from which the electrophoretic mobility and hence zeta potential is calculated. The intensity of the detected, scattered light must be within a specific range for the detector to successfully measure it. This is achieved using an attenuator, which adjusts the intensity of the light reaching the sample and hence the intensity of the scattering. To correct for any differences in the cell wall thickness and dispersant refraction, compensation optics are installed to maintain optimum alignment.

Cationic Polymer

The cationic polymers of the composition include at least one member of the group consisting of cationically-modified polysaccharides, cationizable polysaccharides, and polyvinyl amines and copolymers, for example, vinyl amine/vinyl alcohol copolymers, and vinyl amine/acrylamide copolymers. The cationic polymers have a weight average molecular weight of 35,000 to 10,000,000, more typically in the range of about 200,000 to about 3,000,000 grams/mol.

The cationic charge density is defined as the amount of cationic charge on a given polymer, either by permanent cationic groups or via protonated groups, at the desired pH.

The cationic polymers typically have a cationic charge density of 0.3 to 2, typically 0.4 to 1.7 milliequivalents/gram.

Charge Density (Eq/Grams or Milliequivalents/Gram):

Charge density is the number of charges per weight unit. An equivalent of charge is the amount of charge on a gram equivalent of a substance, i.e., $6.022 \times 10^{23}$ electron charges (Grant & Hackh's Chemical Dictionary Fifth Edition, McGraw-Hill Book Company (1987)). Since charge densities of commercial products are low, those of ordinary skill in the art usually prefer to use millieq/gram.

Cationic charge density (CCD) equals the number of cationic charges per weight unit, in particular, equivalents of cationic units/gram of cationic polymer. An equivalent of cationic charges is a mole of cationic charges. Thus, if a polymer has 100 equivalents/mol of cationic charge and a weight average molecular weight of 1000 g/mol the average CCD is (100 eq/mol)/(1000 g/mol) which equals 0.1 eq/gram or 100 millieq/gram. Typically for polymers average CCD is calculated from the composition of the cationic polymer.

The same average CCD value can also be arrived at by dividing the number of cationic equivalents added to other ingredients to produce a cationic polymer divided by the total weight of the produced cationic polymer.

The CCD of a single molecule of the cationic polymer can also be calculated. If a single molecule of polymer has 100 equivalents/gram of cationic charge and a molecular weight of 1000 g/mol the CCD is (100 eq/mol)/(1000 g/mol) which equals 0.1 eq/gram or 100 millieq/gram.

The cationizable groups are included as a group having a cationic charge for purposes of this CCD calculation if the composition is at a pH suitable for cationizing the cationizable groups.

For polysaccharides, charge density equals the number of charges per sugar ring/molecular weight of the derivatized sugar ring. Thus, for a cationically derivatized polysaccharide, CCD is the number of charges per sugar ring divided by the weight of the derivatized sugar ring. If the cationic polymer is a cationically substituted polysaccharide having monomeric sugar rings as its monomeric units, and there is one cationic equivalent per mol of cationic substitutions, and optionally a non-cationic (typically non-ionic) substituent then average CCD may be calculated from the following formula, wherein MW means molecular weight:

$$CCD = [(X \text{ mol cationic substitutions/mol monomeric units})]/[(MW \text{ non modified monomeric unit (g/mol)}) + ((X \text{ mol cationic substitutions/mol monomeric units}) \times MW \text{ cationic substituent (g/mol)}) + (Y \text{ mol non-cationic substitutions/mol monomeric unit}) \times (MW \text{ non-cationic substituent (g/mol)})]$$

For the polysaccharide, the OH sites of the non modified monomeric sugar ring units are the sites for cationic substitution. For the polysaccharides cationic substitution is typically described in terms of Degree of Substitution (DS).

Degree of Substitution (DS) is the number of substituted hydroxyl groups relative to total number of available hydroxyl groups per monomeric sugar unit. The monomeric sugar units of most polysaccharides (guar, cellulosics, starch, etc) have in average 3 hydroxyl groups available for functionalization. Thus, DS is necessarily in the range 0 and 3.0. DS of 0.1 corresponds to 0.1 hydroxyl group functionalised per sugar unit. In other words, DS of 0.1 corresponds to 1 cationic group per every 10 sugar units. This results in the same number as 1 mol cationic substitutions/10 mols monomeric units since the mols in the numerator and denominator cancel out.

Assuming the molecular weight of a cationization reagent is the molecular weight of the cationic substituent added to the ring and the molecular weight of a non-cationization (typically non-ionic) reagent is the molecular weight of the non-cationic substituent added to the ring then the CCD is calculated as follows for a mol of sugar unit rings of a polysaccharide:

CCD millieq/gm=[DS×(1000millieq/eq)]/[(MW sugar unit (g/mol))+(DS×MW cationization reagent (g/mol))+(MS×MW non-cationic reagent (g/mol))]

MW stands for Molecular Weight (g/mol). As additional background it is mentioned that 1 g/mol=1 Dalton.

MS stands for Molar Substitution: This terminology is used for reagents that can, in theory, form oligomers (propylene oxide, ethylene oxide). In contrast, the term DS is used for reagents which in theory can not oligomerize. So MS can exceed 3.0 whereas DS is in the range from 0 to 3.0 in the case of polysaccharides whose monomeric sugar units possess in average 3 hydroxyl groups.

Thus, if the repeating monomeric unit is a sugar unit, QUAB151 is the cationization reagent, and a hydroxypropyl group (HP) is the non-cationic substituent then this simplifies to the following equation:

CCD millieq/gm=[(DS)×(1000millieq/eq)]/[(MW non-modified sugar unit (g/mol))+(DS×MW QUAB151(g/mol))+(MS×MW HP unit (g/mol))]

MW non modified sugar monomeric unit=162 g/mol

MW QUAB151=151 g/mol (Cationization reagent); QUAB 151 is the trade name for the aqueous solution of the active substance 2,3-epoxypropyltrimethylammonium chloride (glycidyltrimethylammonium chloride; commonly referred to as epoxide) available from QUAB Chemicals. It has the formula II:

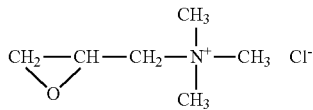

II

MW HP=58 g/mol (Hydroxypropyl group grafted by reaction with propylene oxide $C_3H_6O$)

Hypothetical Sample CCD Calculation 1: for cationic guar of DS=0.1 and MS=0; one cationic charge unit per substitution; calculated based upon a single monomeric sugar ring. Each substituted hydroxyl group is a cationic group with one unit of charge or cationizable group potentially with one unit of charge. Each substituted hydroxyl group included as a cationic unit for purposes of calculating cationic charge density.

$$CCD = [(DS) \times (1000 \text{ millieq/eq})] /$$
$$[(\text{MW sugar unit (g/mol)}) +$$
$$(DS \times \text{MW QUAB151 (g/mol)}) +$$
$$(MS \times \text{MW } HP \text{ unit (g/mol)})]$$
$$= [(0.1) \times (1000 \text{ millieq/eq})] /$$
$$[(162 \text{ g/mol}) + (0.1 \times 151 \text{ g/mol})]$$
$$= 0.56 \text{ millieq/gram}$$

Hypothetical Sample Calculation 2: for cationic HP guar of DS=0.1 and MS=0.6; each hydroxyl group bringing one unit of cationic charge:

$$CCD = [(DS) \times (1000 \text{ millieq/eq})] / [(\text{MW sugar unit (g/mol)}) +$$
$$(DS \times \text{MW QUAB151 (g/mol)}) + (MS \times \text{MW } HP \text{ unit (g/mol)})]$$
$$CCD = [(0.1 \times (1000 \text{ millieq/eq})] / [(162 \text{ g/mol}) + (0.1 \times 151 \text{ g/mol}) +$$
$$(0.6 \times 58 \text{ g/mol})]$$
$$= 0.47 \text{ millieq/gram}$$

At a constant DS in cationic charges, charge density is lower in HP-cationic guars compared to regular cationic guars because the MS increases the molecular weight of the derivatized sugar unit.

TABLE 1 lists ranges of Degree of Substitution/Molecular Substitution/Charge density for JAGUAR guars available from Rhodia Inc, Cranbury, N.J.

TABLE 1

JAGUAR range Degree of Substitution/Molecular Substitution/Charge density

| Product Name | DS | MS | Charge Density calculated value (millieq/grams) |
|---|---|---|---|
| JAGUAR C13S | 0.10-0.13 | | 0.6-0.7 |
| JAGUAR C14S | 0.10-0.13 | | 0.6-0.7 |
| JAGUAR C17 | 0.17-0.20 | | 0.9-1.1 |
| JAGUAR C-HT | 0.25 | | 1.2 |
| JAGUAR EXCEL | 0.10-0.13 | | 0.6-0.7 |
| JAGUAR C1000 | 0.09-0.10 | | 0.5-0.6 |
| JAGUAR C162 | 0.10 | 0.6 | 0.5 |

As mentioned above, for polysaccharides, cationic charge density can also be represented by degree of substitution (DS) in reference to a given type of derivatizing group and a given polysaccharide polymer. DS is in different units than eq/gm. DS means the average number of such derivatizing groups attached to each monomeric unit of the polysaccharide polymer. In one embodiment, the cationically derivatized polysaccharide exhibits a total degree of substitution ("DST") of from about 0.001 to about 3, and more typically from about 0.001 to about 1.0.

DST is the sum of the DS for cationic substituent groups ("DScationic") and the DS for nonionic substituent groups ("DSnonionic").

For a cationic polymer DScationic is typically from >0 to 3, for example about 0.001 to 3, and more typically from about 0.01 to 3.0 or from about 0.01 to about 1.0.

DSnonionic is from 0 to 3.0, more typically from about 0.001 to about 2.5, and even more typically from about 0.001 to about 1.0.

Cationic groups are typically $-N^+R^2R^3R^4X^-$ for amine salt groups $R^2$, $R^3$, and $R^4$ are each independently organic groups or H; for quaternary ammonium groups $R^2$, $R^3$, and $R^4$ are each independently organic groups, or any 2 of $R^2$, $R^3$, and $R^4$ may be fused to form with the nitrogen atom to which they are attached a heterocyclic group, and $X^-$ is an anion.

In one embodiment, the derivatizing agent (also known as a cationic reagent) comprises a cationic substituent group that comprises a cationic nitrogen radical, more typically, a quaternary ammonium radical. Typical quaternary ammonium radicals are trialkylammonium radicals, such as trimethylammonium radicals, triethylammonium radicals, tributylammonium radicals, aryldialkylammonium radicals, such as benzyldimethylammonium radicals, radicals, and ammonium radicals in which the nitrogen atom is a member of a ring structure, such as pyridinium radicals and imidazoline radicals, each in combination with a counterion, typically a chloride, bromide, or iodide counterion. In one embodiment, the cationic substituent group is linked to the reactive functional group of the cationizing agent by an alkylene or oxyalkylene linking group.

Suitable cationizing reagents include, for example: epoxy-functional cationic nitrogen compounds, such as, for example, 2,3 epoxypropyltrimethylammonium chloride; chlorohydrin-functional cationic nitrogen compounds, such as, for example, 3-chloro-2-hydroxypropyl trimethylammonium chloride, 3-chloro-2-hydroxypropyl-lauryldimethylammonium chloride, 3-chloro-2-hydroxypropyl-stearyldimethylammonium chloride, and vinyl-, or (meth)acrylamide-functional nitrogen compounds, such as methacrylamidopropyl trimethylammonium chloride.

Polysaccharide with Primary Amino Groups; Secondary Amino Groups; Tertiary Amino Groups or Guaternized Amino Functional Groups To be cationizable the polysaccharide has primary amino, secondary amino or tertiary amino functional groups. Hereinafter cationizable and polycationic polysaccharides are collectively termed "cationically-modified polysaccharides" and are typically water-soluble.

The solvatable cationically-modified polysaccharides useful herein constitute cationically-modified versions of any of the known class of polysaccharides hydratable in water or an aqueous medium to form a "solution" in which the polysaccharide is uniformly dispersed in the water or aqueous medium.

The polysaccharide with primary, secondary, tertiary or quarternized amine functional groups is schematically shown according to formula (III):

Formula (III) illustrates derivatives of typical galactomannans, characterized by a linear backbone of 1,4-linked b-D-mannopyranose units with a-D-galactopyranose single lateral units attached to the 6-O position of mannose units. Other polysaccharides, with macromolecular architectures and composition that differ from the galactomannans' ones are also included, for example cellulosics, starches, chitosan, chitin, etc.

The value of n sufficient to achieve above described molecular weight. If $^+N(R)_3$ is present then there is also $X^-$ which is an anion, typically a chloride, bromide, methosulfate, ethosulfate, lactate, saccharinate, acetate or phosphate anion. Multiple quarternized amine functional groups of the cationic polymer may be the same or different.

A typical subclass of cationically modified-polysaccharides includes those polysaccharides which have a plurality of vicinal hydroxy groups oriented sterically in a cis configuration. The broad class of solvatable polysaccharides include galactomannan gums, glucomannan gums, and other such hydrophilic vegetable gums, and certain cellulose derivatives. The solvatable galactomannan gums and glucomannan gums are, of course, naturally occurring. However, the cellulose derivatives are reaction products of cellulose with compounds which render the cellulose derivatives solvatable and crosslinkable by the chemical attachment of hydrophilic constituents to the cellulose backbone. Similarly, derivatives of the naturally occurring gums can be prepared and used herein so long as the derivatives thereof are solvatable and crosslinkable. For example, the reaction product of guar gum with propylene oxide gives a derivative known as hydroxypropylguar (HPG). As a galactomannan, guar gum is a branched copolymer containing a mannose backbone with galactose branches. Of the cationically-modified polysaccharides, cationically-modified guar and its derivatives are particularly well suited for the present invention. These include cationically-modified guar gum, cationically-modified hydroxyalkylguar, for example cationically-modified hydroxyethylguar, cationically-modified hydroxypropylguar, cationically-modified guar, and combinations thereof. Cationically-modified heteropolysaccharides, such as diutan,

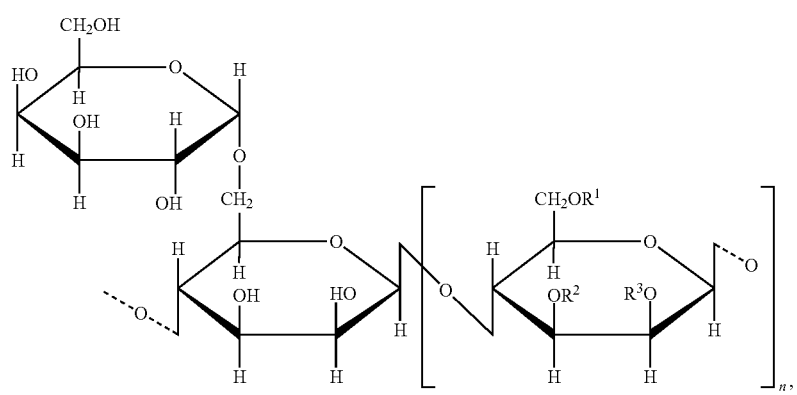

III wherein each of $R^1$, $R^2$, $R^3$ is independently H, C1-C20 alkyl, C1-C20 alkoxy, COOH, COOM, $ANH_2$, ANRH, $ANR^2$, or $A^+N(R)^3$, at least one of $R^1$, $R^2$, $R^3$ is $ANH_2$, ANRH, or $A^+N(R)^3$, wherein R is H or C1-C20 alkyl, wherein A is C1-10 alkyl, typically C1-4 alkyl. Typically, each of $R^1$, $R^2$, $R^3$ is independently H, C1-C6 alkyl, C1-C6 alkoxy, COOH, COOM, $ANH_2$, ANRH, or $A^+N(R)_3$, at least one of $R^1$, $R^2$, $R^3$ is $ANH_2$, ANRH, or $A^+N(R)_3$, wherein R is H or C1-C6 alkyl, wherein A is C1-10 alkyl, typically C1-4 alkyl. M is hydrogen or sodium.

may also be used as the hydratable cationic polymer. Hydrophobically-modified cationic guar may also be used as the cationic polymer. Typically the hydrophobes of the hydrophobically-modified cationic guar are C12-30, for example C12-18, alkyl groups.

The known class of solvatable polysaccharides suitable for being cationically-modified includes, for example, cara gum, locust bean gum and guar gum, as well as other galactomannan and glucomannan gums, such as those from endosperms of seeds of other leguminous plants such as the sennas, Brazilwood, Tera, Honey locust, Karaya gum and the like. Other examples include cationically modified derivatives of such gums, such as hydroxyethylguar, hydroxypropylguar, and the like. Other examples include cationically modified cellulose derivatives containing hydroxy groups such as, cationically modified cellulose, cationically modified hydroxyl alkyl cellulose, such as hydroxyethyl cellulose and the like.

There is typically an absence of anionic guar, for example there is typically an absence of carboxymethylhydroxyalkyl guar, such as carboxymethylhydroxypropyl guar (CMHPG). Typically, CMHPG is anionic.

Cationically-modified polysaccharides such as guar gum and hydroxypropylguar are preferred for use in the present invention and cationically-modified guar gum and cationically-modified cellulose are the most preferred based upon commercial availability and desirable properties. The solvatable cationically-modified polysaccharides can be used individually or in combination; usually, however, a single material is used.

In the present invention, the solvatable cationically-modified polysaccharides are normally blended with water or an aqueous medium (e.g. aqueous methanol, ethanol, 1 to 3% HCl, potassium chloride, etc.) to form an uncrosslinked gel as a first step. If desired a cross-linker is subsequently added to cause the polysaccharide to cross-link. Typical crosslinking agents are Group 4 transition metal compound crosslinking agents, for example crosslinking agents which contain a polyvalent zirconium ion (i.e. a zirconium atom in the plus four oxidation state). However, compositions of the present invention may also have an absence of cross-linker.

The amount of solvatable cationically-modified polysaccharide used in making a composition can vary in the instant invention. Usually only a small amount of cationically-modified polysaccharide is employed because of the high efficiency such cationically-modified polysaccharides display in thickening aqueous media. For most applications, satisfactory composition are made by adding the solvatable cationically-modified polysaccharide in amounts up to about 5 weight percent, based on the weight of the aqueous liquid. Preferred amounts of cationically-modified polymer generally range from about 0.3 to about 3 weight percent.

Typical polysaccharides for use in the invention are polysaccharides with primary amino groups, such as glucosamine units, or their precursors, such as N-acetyl-glucosamine units. For example, chitin or chitosan. Chitin is shown in Formula IVa:

The following 3 references give additional information about chitin or chitosan: Reactive and Functional Polymers, Volume 46, Issue 1, November 2000, Pages 1-27; Industrially important polysaccharides Applied Polymer Science: 21st Century, 2000, Pages 303-323; Chitin and chitosan: Properties and applications, Progress in Polymer Science, Volume 31, Issue 7, July 2006, Pages 603-632

Cationically modified xanthan gum is another suitable polysaccharide for use in the invention.

Polyvinyl Amines and Copolymers

Polyvinyl amines and copolymers, for example, vinyl amine/vinyl alcohol copolymers, and vinyl amine/acrylamide copolymers.

Polyvinyl amines and copolymers are cationizable polymers that have primary amino groups and typically are water-soluble.

Polyvinyl amine homopolymers contain the monomeric unit shown in Formula V:

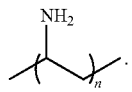

V

In Formula V "n" is sufficient to achieve the desired molecular weight.

The invention also contemplates polyvinyl amine copolymers, for example, vinyl amine-vinyl alcohol copolymers or vinyl-amine acrylamide copolymers. Typical vinyl amine-vinyl alcohol copolymers (PVAVAMs) have the structure of Formula VI, $$-(CH_2-HCOH)_x-(CH_2-NH2)_y-$$  VI, x and y are integers, wherein the sum of x+y is sufficient to achieve the desired molecular weight and CCD. In the PVAVAMs of the present invention, it is typical that x of Formula VI is 91-98.7 mole %, y is 1.3-9.0 mole %. More typically, x is 98.2-92.5 mole %, y is 1.8-7.5 mole %. For purposes of the present invention, "mole %" is defined as the percentage of the total mole units in the polymer.

The vinyl alcohol/vinyl amine copolymers (PVAVAMs) of the present invention have a CCD of about 0.3-about 2.0

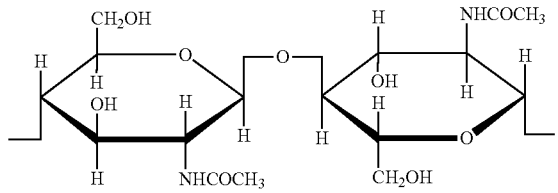

IVa

Chitosan is shown in Formula IVb:

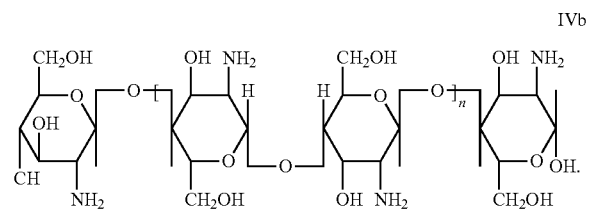

IVb millieq/g, typically 0.4-1.7 millieq/g. Typical molecular weights of monomeric units are: vinyl amine: 43 g/mole; vinyl alcohol units=44 g/mole.

A particular typical vinyl amine-vinyl alcohol copolymer (PVAVAM) has the structure of Formula VII,

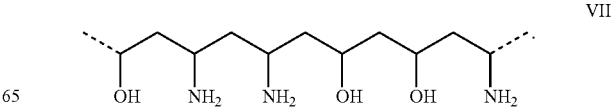

VII

Additional information about polyvinylamines and copolymers is provided by Tappi Journal, 1(10), 20-27 (2002); Journal of Applied Polymer Science, Volume 89, Issue 5, pages 1277-1283 (2003); Macromolecules, 40, 1624-1630 (2007); Colloids and Surfaces A: Physicochemical and Engineering Aspects, Volume 172, Issues 1-3, Pages 47-56 (2000); and Journal of Polymer Science Part A: Polymer Chemistry, Volume 48, Issue 11, pages 2257-2283 (2010).

Modified polyvinyl amines suitable in the present invention include polyvinyl amine modified with polyethylene glycol (PVAm-g-PEG) as shown in Formula VIII.

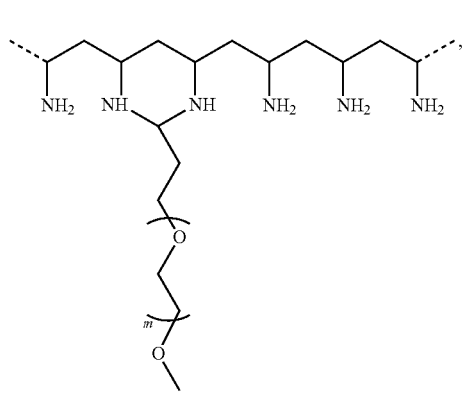

VIII wherein m is 1 to 100. Additonal information about this polymer is available from Journal of Biomedical Materials Research, Volume 50, Issue 3, pages 302-312 (2000).

Polyamine polymers suitable in the present invention with secondary amino groups are polyethylene imines (PEI) shown in Formula IX. An example of polyvinyl amine is Lupasols® from BASF.

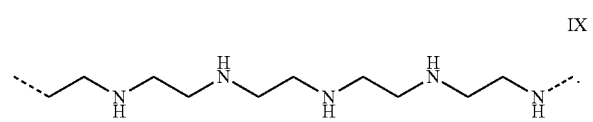

IX

Modified polyamine polymers with secondary amino groups suitable in the present invention include ethoxylated PEIs modified with polyethylene glycol (PEI-g-PEG) as shown in Formula X.

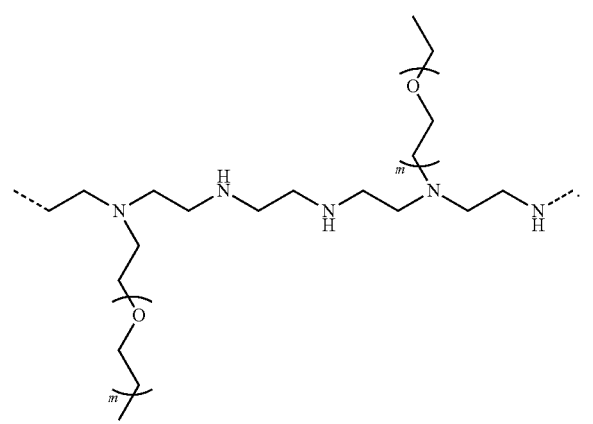

X wherein each m is 1 to 100.

Branched PEIs containing primary, secondary and tertiary amino groups suitable in the present invention are shown in Formula XI. These branched PEIs can also be ethoxylated, yielding PEIs with PEG chains.

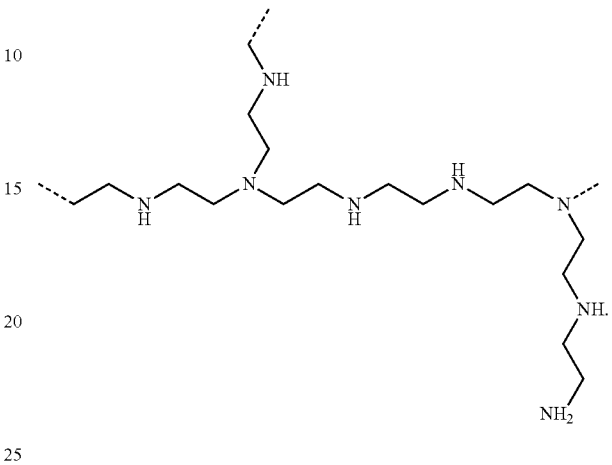

XI

Many cationic or cationizable polymers of interest are disclosed in C. Chappell, Jr., E. L. Mason, and J. A. Siddiqui, Specialty Monomers and Polymers, Chapter 14, pp. 186-199, ACS Symposium Series, Vol. 755.

Polyvinyl amines have extremely high pKa, around 10.5-11, which makes them partially cationic even at high pH. This is a unique property. Next are PEIs with a pKa lower than polyvinyl amines, then Chitosan with a pKa of about 6.5-7. An advantageous property of PVAMs and their copolymers is that they can have very high molecular weight.

Also, pH-sensitive cationic polymers may also be made from monomers with structures of Formula XIIa, XIIb, XIIc, XIId and XIIe.

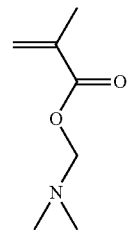

XIIa

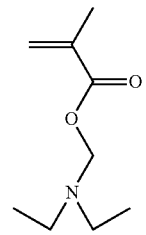

XIIb

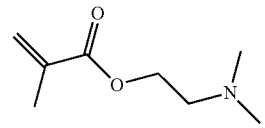

XIIc

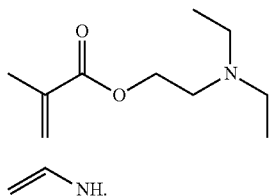 XIId

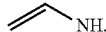 XIIe

Structure XIIa represents N,N'-dimethylaminomethyl methacrylate; Structure XIIb represents N,N'-diethylaminomethyl methacrylate; Structure XIIc represents N,N'-dimethylaminoethyl methacrylate; Structure XIId represents N,N'-diethylaminoethyl methacrylate; and Structure XIIe represents vinyl amine monomer.

Anionic Polymer

The at least one anionic polymer is selected from the group consisting of polyacrylic acid, partially hydrolyzed polyacrylamide, substituted polyacrylamide and acrylate copolymer (HASE; copolymers of alkylacrylate, methylacrylate, methylmethacrylate and/or ethylacrylates with acrylic acid and/or acrylamide), the at least one anionic polymer having a weight average molecular weight of 30,000 g/mol to 10,000,000 g/mol, for example, 30,000 to 500,000 g/mol, more typically 50,000 g/mol to 500,000 g/mol.

The anionic charge range for anionic polymers of the present invention is 0.1 to 20 milliequivalents/gram, or typically 0.4 to 15 milliequivalents/gram, or typically 1 to 15 milliequivalents/gram, or typically 1 to 10 milliequivalents/gram, or typically 9 to 15 milliequivalents/gram of anionic material, or 1 to 5 milliequivalents/gram of anionic material.

Anionic charge density (ACD) equals the number of anionic charges per weight unit, in particular, equivalents of anionic units/gram of anionic polymer. An equivalent of anionic charges is a mole of anionic charges. The method of calculating ACD parallels that of calculating CCD. Thus, if a polymer has 100 equivalents/mol of anionic charge and a weight average molecular weight of 1000 g/mol the average ACD is (100 eq/mol)/(1000 g/mol) which equals 0.1 eq/gram or 100 millieq/gram. Typically for polymers average ACD is calculated using a weight average molecular weight. Since charge densities of commercial products are low, those of ordinary skill in the art usually prefer to use millieq/gram.

The same average ACD value can also be arrived at by dividing the number of anionic equivalents added to other ingredients to produce a anionic polymer divided by the total weight of the produced anionic polymer.

The ACD of a single molecule of the anionic polymer can also be calculated. If a single molecule of polymer has 100 equivalents/gram of anionic charge and a molecular weight of 1000 g/mol the ACD is (100 eq/mol)/(1000 g/mol) which equals 0.1 eq/gram or 100 millieq/gram.

Typically, the anionic polymers can be, but are not limited to, carboxylate-containing, sulfate or sulfonate-containing, phosphonate or phosphate-containing, or neutral but hydrolysable to gain negative charges, such as but not limited to acrylamide. Typically, the polyacrylic acid, partially hydrolyzed polyacrylamide or acrylate copolymer has functional groups selected from at least one member of the group consisting of carboxylate, sulfate, sulfonate, phosphate or phosphonate. Typically, the substituted polyacrylamide optionally has one or more functional groups selected from the group consisting of sulfate, sulfonate, phosphate or phosphonate.

Typical anionic polymers contain carboxylate functionalities from acrylic acid, methacrylic acid, itaconic acid, fumaric acid, crotonic acid, and maleic acid.

Typically, the composition of the present invention has a pH of 6 to 12. However, other pH compositions are also contemplated.

A typical anionic polymer is a polyacrylic acid comprising a functional group selected from the group consisting of carboxylate and/or sulfonate. Another typical anionic polymer is partially hydrolyzed polyacrylamide, comprising a functional group selected from the group consisting of carboxylate and optionaly sulfonate. Another typical anionic polymer is acrylate copolymer comprising a copolymer of acrylic acid and methacrylic acid each comprising a functional group selected from the group consisting of carboxylate and/or sulfonate. Another typical anionic polymer is a copolymer of alkylacrylate with acrylic acid and/or methacrylic acid comprising a functional group selected from the group consisting of carboxylate and/or sulfonate.

Rather than or in combination with the above-mentioned anionic polymer can be used at least one hydrolysable polymer selected from the group consisting of polyalkylacrylate, polyacrylamide and copolymers of polyalkylacrylate and polyacrylamide. The at least one hydrolysable polymer having a weight average molecular weight of 30,000 g/mol to 10,000,000 g/mol. The at least one hydrolysable polymer at least partially hydrolyzes to an anionic polymer having an anionic charge density of 0.1 to 20 milliequivalents/gram, or typically 0.4 to 15 milliequivalents/gram, or typically 1 to 15 milliequivalents/gram, or typically 1 to 10 milliequivalents/gram, or typically 9 to 15 milliequivalents/gram of anionic material, or 1 to 5 milliequivalents/gram at a temperature of greater than 100 to 250° C.

Typical anionic polymer monomeric units have the structure shown in Formula XIII:

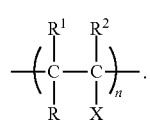 XIII

X is selected from the group consisting of: COOM, SO$_3$M, OSO$_3$M, PO$_3$M$_2$, OPO$_3$M; wherein M is selected from the group consisting of H, Na$^+$, K$^+$, and NH$_4{}^+$. R, R$^1$ and R$^2$ are selected from the group consisting of linear or branched C1-16 alkyl (typically C1-C4), phenyl, methyl- or ethyl-substituedphenyl, monomeric unit, styrene monomeric unit, methyl- or ethyl-substitued styrene monomeric unit.

As a result of combining the cationic (and/or cationizable) and anionic (and/or anionizable or hydrolyzable) polymers the overall composition has a zeta potential at 25° C. in the range of 0.5 to 100 mV or −0.5 to −100 mV, typically 1 to 60 mV or −1 to −60 mV, also typically 14 to 50 mV or −14 to −50 mV, also typically 30 to 50 mV or −30 to −50 mV or is a precursor convertible at a temperature of 100 to 250° C. to the composition having a zeta potential at 25° C. of 0.5 to 100 mV or −0.5 to −100 mV, typically 1 to 60 mV or −1 to −60 mV, also typically 14 to 50 mV or −14 to −50 mV, also typically 30 to 50 mV or −30 to −50 mV. For example, the composition comprising the cationic polymer and the hydrolysable polymer, after it hydrolyzes to an anionic at least partially hydrolyzed polymer, has the desired zeta value.

Polyacrylamide

The polyacrylamide polymer comprises $CH_2:CHCONH_2$ linear polymers polymeric through the vinyl groups. As used herein, the expressions "polyacrylamide" or "acrylamide polymer" are meant to include both acrylamide homopolymers and copolymers of acrylamide with other monomers unless stated otherwise or as is apparent from its context. An acrylamide polymer is generally obtained by polymerizing acrylamide alone or copolymerizing acrylamide and another monomer copolymerizable with acrylamide in an aqueous medium.

The polyacrylamides are catagorized in three catagories. The polyacrylamide in general and specifically in all three catagories has a weight average molecular weight of 30,000 g/mol to 10,000,000 g/mol, typically a weight average molecular weight of 30,000 g/mol to 500,000 g/mol, more typically 50,000 g/mol to 500,000 g/mol.

The first category is hydrolysable polyacrylamide which is nonionic intially but will partially hydrolyze in situ during use to an anionic polymer having an anionic charge density of 0.1 to 20 milliequivalents/gram, typically 0.4 to 15 milliequivalents/gram, or or typically 1 to 15 milliequivalents/gram, or typically 1 to 5, or typically 9 to 15 at a temperature of greater than 100 to 250° C. Thus, during use sufficient acrylamide monomeric units hydrolyze to acrylate monomeric units resulting in a polyacrylamide-acrylate copolymer. Typically, this hydrolysable polyacrylamide is a homopolymer. As used herein, the term homopolymer is meant to encompass polymers having less than about 0.1% by weight of any other monomers. The acrylamide homopolymer is a nonionic polymer made of acrylamide monomers, $CH_2=CHCONH_2$. However, a copolymer of acrylamide momomer and non-acrylamide monomer may also be hydrolysable. In general the compositions of the present invention, encompassing hydrolysable acrylamide polymers, are those in which upon initially making the composition the acrylamide does not have anionic charge density of 0.1 to 50 g/eg and the overall composition does not have a zeta potential of 0.01 to 50 or −0.01 to −50 at 25° C. However, the acrylamide at least partially hydrolyzes to an anionic polymer having an anionic charge density of 0.1 to 50 g/eg at a temperature of greater than 100 to 250° C. As a result, the composition containing the cationic and (after the hydrolysable polymer has been hydrolyzed) anionic polymers has a zeta potential of 0.01 to 50 or −0.01 to −50 at 25° C.

The second category is substituted polyacrylamide that already is anionic due to the presence of anionic functional groups dangling from acrylamide functional groups. Such functional groups are selected from the group consisting of carboxylate, sulfate, sulfonate, phosphate or phosphonate. The substituted polyacrylamide polymer may be an anionically-modified homopolymer.

The third category includes copolymers of acrylamide monomers with one or more different (non-acrylamide) monomers having the functional groups selected from the group consisting of carboxylate, sulfate, sulfonate, phosphate or phosphonate. The non-acrylamide monomers are selected to provide the anionic properties. The copolymers may be block or random copolymers. The non-acrylamide monomers may make up from about 0.1% to up to about 50% or more of the copolymer, more particularly from about 5% to about 15% to provide an anionic charge density of 0.1 to 50 g/eg.

The carboxylate groups are typically provided by acrylate monomeric units. For example, in the acrylamide-acrylate copolymer, the acrylate segments are anionic. Examples of suitable non-acrylamide monomers include acrylate monomers resulting in an acrylate acrylamide copolymer. Typical acrylates for these copolymers are alkylacrylate, sodium acrylate, potassium acrylate and ammonium acrylate. Typically the acrylates are sodium acrylate monomers or alkylacrylate monomers, wherein the alkyl group has 1 to 10 carbon atoms. Typical copolymers have alkylacrylate, methylacrylate, methylmethacrylate and/or ethylacrylates with acrylic acid and/or acrylamide. The acrylate acrylamide copolymer has functional groups provided by a co-monomer in addition to the alkylacrylate monomer or acrylamide monomer or provided by substitution onto the alkylacrylate monomer and/or the acrylamide monomer.

It should be understood, however, that copolymers of polyacrylamide further having non-anionic functional groups are contemplated as falling within the scope of the present invention.

Acrylamide-acrylate copolymers can be formed by copolymerization of acrylamide monomers and acrylate monomers.

Acrylamide-acrylate copolymers may also be formed by hydrolysis of an acrylamide homopolymer typically conducted with heat under alkaline reaction conditions. Acrylamide-acrylate copolymers may also be formed by hydrolysis of an acrylamide homopolymer. These acrylamide-acrylate copolymers formed by hydrolysis are also known as partially hydrolyzed acrylamides.

A suitable formulation utilizes a copolymer of acrylamide and sodium acrylate present in a mol ratio of approximately 70:30; however, different ratios of acrylamide:sodium acrylate also fall within the scope of the present invention. In an embodiment the polyacrylamide is a copolymer of acrylamide and acrylate monomers or other monomers and wherein the acrylate or other monomers comprise from about 0.1% to about 50 wt. % of the copolymer.

The polyacrylamide may be used in the fluids of the invention in an amount of from about 0.01% to about 25% by weight of the fluid. In certain applications, the polyacrylamide may be used in an amount of from about 0.03% to about 010% by weight of the fluid. The polyacrylamide may be added in liquid form, such as dispersed in mineral oil, water or other carrier. The polyacrylamide may also be added in solid or particulate form.

As mentioned above, an acrylamide-acrylate copolymer, also known as a partially-hydrolyzed polymer, may be obtained by treating the acrylamide polymer with an alkaline substance to subject the polyacrylamide to an initial phase of hydrolysis. The polyacrylamide undergoes hydrolysis under alkaline conditions in a controlled degree. For example, a base of a predetermined concentration may be added to the polyacrylamide to the extent that the polymer will be expected to hydrolyze to a certain degree. Conditions should be controlled because hydrolysis of polyacrylamide may lead to by-products, such as ammonia, which may cause subsequent hydrolysis, the polymer may then undergo undesired hydrolysis.

As an industrially-applicable preparation process of a partially-hydrolyzed, solid acrylamide polymer, U.S. Pat. No. 4,146,690 teaches dividing a hydrous gel of a polymer, which has been obtained by polymerization of an aqueous solution of acrylamide, into grains, mixing an aqueous caustic alkali solution with the thus-formed grains and subsequently drying them by hot air. In this process, the hydrolysis reaction of the polymer is allowed to proceed only to the extent of about 20-30% of the intended percentage of hydrolysis during its mixing with the caustic alkali. The remaining part of the hydrolysis reaction is allowed to take place in the hot-air drying step. Namely, the added caustic alkali adheres substantially in its entirety on polymer grains but the hydrolysis reaction of the polymer grains does not take place to any significant extent while the polymer grains are mixed with the caustic alkali, because the reaction velocity of hydrolysis is slow at low temperatures. The hydrolysis is brought to completion in the subsequent hot-air drying step, owing to the action of the caustic alkali adhered on surfaces of the polymer grains.

The hydrolyzed acrylamide polymer used herein has from 1 to 50% unhydrolyzed amide groups. Preferably the polymer has from 10-20% unhydrolyzed amide groups. The hydrolyzed polyacrylamide has carboxylate functional groups in its acrylate groups. If desired the hydrolyzed polyacrylamide also may have functional groups selected from the group consisting of carboxylate, sulfate, sulfonate, phosphate or phosphonate in other monomeric units. Sulfate is typically provided from a sulfate or sulfosuccinate. An example of a suitable acrylamide copolymer including a sulfonate-containing monomeric unit is acryamido-methylpropane sulfonate (AMPS)-acrylamide copolymer.

Structures of typical hydrolyzed monomeric units are disclosed by Formula XIV.

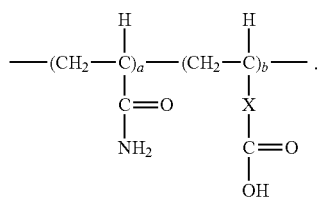

In Formula XIV, X is a bond or C1-6 linear or branched alkyl, a+b is enough to achieve a weight average molecular weight of 30,000 to 100,000 g/mol; a is at least 1; and b is at least 1.

Structures of typical copolymer monomeric units are disclosed by Formula XV:

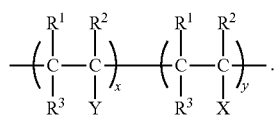

In Formula XV, X is selected from the group consisting of: COOM, —C(O)NH$_2$, SO$_3$M, OSO$_3$M, PO$_3$M$_2$, OPO$_3$M, and CH$_2$OH.

M is selected from the group consisting of H, Na$^+$, K$^+$, and NH$_4^+$.

R$^2$ is X or Y.

R$^1$ and R$^3$ are selected from the group consisting of H and C1-20 alkyl.

Y has the formula XVI:

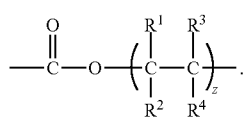

R$^1$ and R$^2$ are selected from the group consisting of H and C1-20 alkyl. R$^4$ is selected from the group consisting of H and C1-20 alkyl.

Parameter "z" is 0 to 100. For example, a random copolymer of 2-hydroxy ethyl methacrylate and alkylamide.

If Y is PO$_3$M$_2$, where M is H or methyl, a typical copolymer is a copolymer of vinyl phosphoric acid and acrylamide. Formula XVII shows an organo-soluble phosphorus-containing polymer suitable for the present invention.

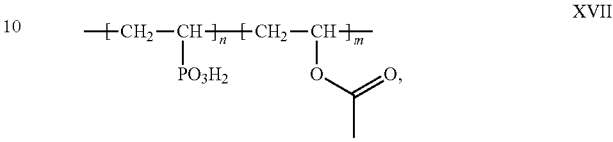

wherein n and m are greater than 0 and sufficient to achieve the above-described molecular weight.

Formulas XVIIIa and XVIIIb show water-soluble phpsphorus-containing polymers suitable for the present invention.

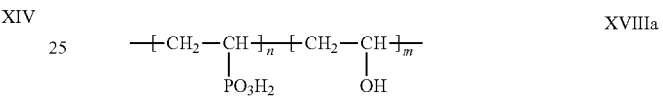

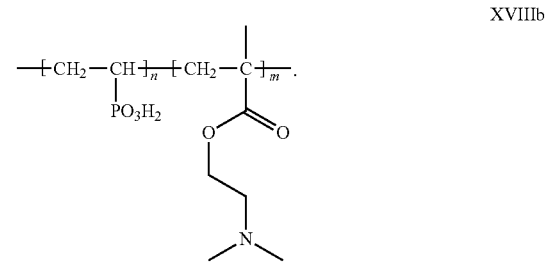

Formula XIX shows poly(VPA-vinyl alcohol-acrylic acid) random terolymer suitable for the present invention. VPA is an abbreviation for vinyl phosphine acid.

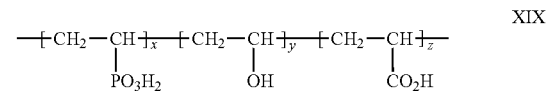

If "y" equals 0 the material is a homopolymer.

Polyacrylic Acid

The polyacrylic acid and salts thereof for use as anionic polymers in the present invention have a molecular weight of from about 30,000 to 10,000,000 g/mol, typically 30,000 to about 500,000 g/mol, more typically 50,000 g/mol to 500,000 g/mol. Polyacrylic acid polymers are commercially available from a variety of sources. The polyacrylic acid polymers are of the type identified in Chapter 17 of the Handbook of Water Soluble Gums and Resins, by R. L. Davidson, McGraw Hill 1980. The polyacrylic acid can be obtained either by polymerization of acrylic acid monomer or by polymerization of a monomer of alkyl acrylate type, such as, for example, methyl or butyl acrylate, followed by a hydrolysis.

The polyacrylic acid polymers and their salts that can be used comprise water soluble low molecular weight polymers having the formula XX.

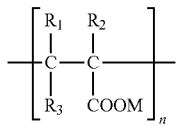

XX wherein the R1, R2 and R3 can be the same or different and can be hydrogen, C1-C4 lower alkyl, or combinations thereof. The value of n is 5 to 2000, preferably 10 to 1500, and more preferably 20 to 1000. M represents hydrogen, or an alkali metal such as sodium or potassium. The preferred substituent for M is sodium ($Na^+$), potassium ($K^+$), lithium ($Li^+$), ammonium ($NH_4^+$), phosphate ($PR_4^+$ where R is alkyl or aryl) or phosphonate (C—$PO(OH)_2$ or C—$PO(OR)_2$ groups where R is alkyl, aryl).

The preferred R1, R2 and R3 groups are independently hydrogen, methyl, ethyl and propyl. Preferred acrylic acid monomer is one where R1, R2 and R3 are independently hydrogen, e.g. acrylic acid, or where R1 and R3 are hydrogen and R2 is methyl, e.g. methyl acrylic acid monomer.

The degree of polymerization, i.e. the value of n, is generally determined by the limit compatible with the solubility of the polymer or copolymer in water. The terminal or end groups of the polymer or copolymer are not critical and can be H, OH, $CH_3$ or a low molecular weight hydrocarbon.

Typically the anionic polyacrylic acid copolymers can include copolymers of, for example, acrylic acid or methacrylic acid and a polycarboxylic acid anhydride or acid such as succinic anhydride, succinic acid, maleic acid, maleic anhydride, citric acid and the like. A preferred polymer comprises a copolymer of polyacrylic acid and methacrylic acid. Suitable copolymers also include copolymers of alkylacrylate, methylacrylate, methylmethacrylate and/or ethylacrylates with acrylic acid and/or acrylamide as described above in the description of polyacrylamides.

The acrylic acid polymers and copolymers are anionic by including functional groups selected from the group consisting of carboxylate, sulfate, sulfonate, phosphate or phosphonate. The functional groups can dangle from an acrylic acid or methacrylic acid monomeric unit (in other words be part of a substituted acrylic acid or methacrylic acid monomeric unit). The functional groups can be part of an acrylic acid or methacrylic acid monomeric unit as in the case of carboxylate or be part of a non-acrylic acid, non-methacrylic acid comonomeric unit, for examples as a phosphate or phosphonate. The monomeric units may be naturally anionic or become anionic at an appropriate pH.

Acrylic acid polymers and copolymers can be made using procedures known in the art, see for example U.S. Pat. No. 4,203,858.

The amount of the polyacrylic acid polymer or copolymer stabilizer employed in compositions such as fracturing fluids or personal care products or cleaning products varies depending on the desired enhancement of viscosity varies and the other composition ingredients. Typically, however, suitable amounts of the polyacrylic acid polymer or copolymer stabilizing agents range from about 0.3 to 5% by weight, more typically 0.5 to 1.5 wt. % of the composition.

Acrylate Co-Polymer

The anionic polymer may be derived from at least one co-monomer and at least one polymerizable reactive alkoxylated acrylate monomer wherein the acrylate copolymer has functional groups selected from the group consisting of carboxylate, sulfate, sulfonate, phosphate or phosphonate. For the acrylate copolymer the functional group can be provided by a co-monomer in addition to the acrylate monomer or it can be provided by substitution onto the acrylate monomer.

The acrylate ion (C $H_2$=CHCOO$^-$) is the ion of acrylic acid. Acrylates are the salts and esters of acrylic acid.

The polyacrylic acid polymers and their salts that can be used comprise water soluble low molecular weight polymers having the formula XXa.

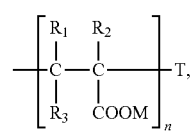

XXa wherein the R1, R2 and R3 can be the same or different and can be hydrogen, C1-C4 lower alkyl, or combinations thereof. The value of n is 5 to 2000, preferably 10 to 1500, and more preferably 20 to 1000. M represents hydrogen, or an alkali metal such as sodium or potassium. The preferred substituent for M is sodium ($Na^+$), potassium ($K^+$), lithium ($Li^+$), ammonium ($NH_{4+}$), phosphate ($PR_4^+$ where R is alkyl or aryl) or phosphonate (C—$PO(OH)_2$ or C—$PO(OR)_2$ groups where R is alkyl, aryl).

The preferred R1, R2 and R3 groups are independently hydrogen, methyl, ethyl and propyl. Preferred acrylic acid monomer is one where R1, R2 and R3 are independently hydrogen, e.g. acrylic acid, or where R1 and R3 are hydrogen and R2 is methyl, e.g. methyl acrylic acid monomer.

The degree of polymerization, i.e. the value of n, is generally determined by the limit compatible with the solubility of the polymer or copolymer in water. The terminal or end groups of the polymer or copolymer are not critical and can be H, OH, CH3 or a low molecular weight hydrocarbon.

"T" is another monomeric unit. Typical acrylate copolymers are copolymers of alkylacrylate, methylacrylate, methylmethacrylate and/or ethylacrylates with acrylic acid and/or acrylamide wherein the acrylate copolymer has functional groups selected from the group consisting of carboxylate, sulfate, sulfonate, phosphate or phosphonate.

The alkylacrylate acrylamide copolymers are discussed above in detail in the description of acrylamide copolymers.

Another anionic acrylate may have the structural formula XXIa or XXIb:

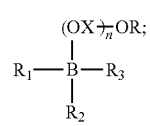

XXIa

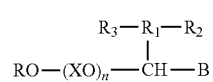

XXIb wherein B is a 5 or 6 membered cycloalkyl ring, or a single ring aromatic hydrocarbon having a 6 membered ring, R1, R2 and R3 are independently selected from the group consisting of XXIIa, b, c, d:

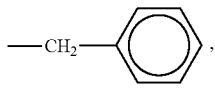
XXIIa

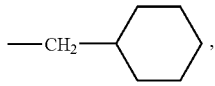
XXIIb

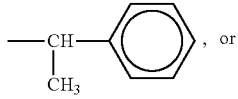
XXIIc

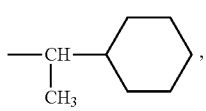
XXIId wherein, X is selected from the group consisting of $C_2H_4$, $C_3H_6$, and $C_4H_8$, wherein n is in the range of 1-100, wherein R is an ethylenically unsaturated group.

The anionic charge may be provided by the co-monomer being provided with a functional group selected from the group consisting of carboxylate, sulfate, sulfonate, phosphate or phosphonate. The at least one anionic polymer having a weight average molecular weight of 30,000 to 10,000,000 g/mol, for example, 30,000 g/mol to 500,000 g/mol, more typically 50,000 g/mol to 500,000 g/mol, and an anionic charge density of 0.1 to 20 milliequivalents/gram, typically 0.4 to 15 milliequivalents/gram, also typically 1 to 10 milliequivalents/gram, also typically 1 to 5 milliequivalents/ gram.

For example, a typical embodiment of monomeric unit is as shown in formula XXIII.

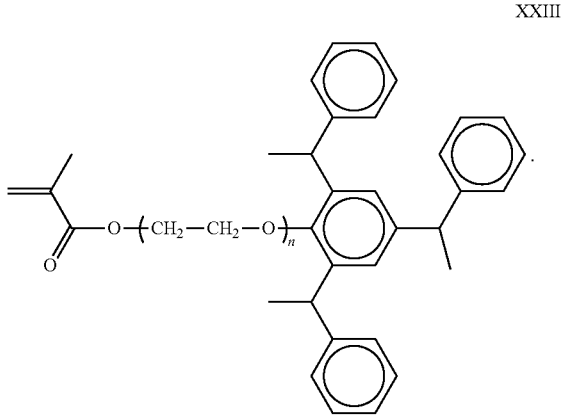
XXIII wherein n ranges from 5 to 50.

Hydrophobically Modified Alkali-Soluble Emulsion (HASE) Polymer

Another embodiment of an acrylate co-polymer as the polyantionic polymer is a HASE polymer. This HASE polymer comprises a chain of monomeric units. The polymer is a macromolecule having a relatively high molecular mass that comprises chains of multiple repetitions of the monomeric units, which are derived, actually or conceptually, from molecules of relatively low molecular mass and are connected to form a linear, branched, or network structure. The polymer typically has a linear or branched structure, more typically single strand linear or branched structure. In one embodiment, a polymer having a predominantly single strand linear or branched structure is lightly crosslinked to form a polymer network having a low density of crosslinks. As used herein the term "single strand" in regard to a polymer means monomeric units of the polymer are connected such that adjacent monomeric units are joined to each other through two atoms, one on each of the adjacent monomeric units.

Although this polymer is described as a HASE polymer it is not necessary to make a polymer of this structure by emulsion polymerization. The polymer may also be made by solution polymerization and comes within the invention whether made by emulsion polymerization or solution polymerization.

The HASE polymer is provided with its polyanionic charge by comprising functional groups selected from the group consisting of carboxylate, sulfate, sulfonate, phosphate or phosphonate.

The polymer may typically be regarded as having a "backbone", or main polymer chain, from which all branches and substituent groups of the polymer may be regarded as being pendant. Where two or more chains of the polymer could equally be considered to be the main chain of the polymer, that chain is selected as the main chain which leads to the simplest representation of the polymer molecule. The monomeric units of the polymer may be arranged in random, alternating, tapered, or block sequence along the polymer chain.

The HASE anionic polymer comprises:

one or more first monomeric units, each independently comprising at least one bicycloheptyl-polyether, bicycloheptenyl-polyether or branched ($C_5$-$C_{50}$)alkyl-polyether group per monomeric unit, wherein the bicycloheptyl-polyether or bicycloheptenyl-polyether group may optionally be substituted on one or more ring carbon atoms by one or two ($C_1$-$C_6$)alkyl groups per carbon atom, and optionally one or more second monomeric units, each independently comprising at least one pendant linear or branched ($C_5$-$C_{50}$)alkyl-polyether group per monomeric unit, provided that the first and second monomeric units cannot both comprise a branched ($C_5$-$C_{50}$)alkyl-polyether group;

there may also be third and fourth monomeric units.

In an embodiment, HASE polymers may be synthesized using methacrylic acid which contains carboxylic groups. At high pH, about 7, carboxylic groups have a negative charge.

In one embodiment, the polyanionic HASE polymer comprises:

one or more first monomeric units, each independently comprising at least one at least one bicycloheptyl-polyether or bicycloheptenyl-polyether group per monomeric unit, and one or more second monomeric units, each independently comprising at least one pendant linear or branched ($C_5$-$C_{50}$) alkyl-polyether group per monomeric unit, the polymer having a weight average molecular weight of greater than or equal to about 30,000 to 10,000,000 g/mol, typically about 30,000 to 500,000 g/mol, more typically 50,000 g/mol to 500,000 grams per mole.

In one embodiment, the polyanionic HASE polymer of the present invention comprises:

one or more first monomeric units, each independently comprising at least one branched ($C_5$-$C_{50}$)alkyl-polyether group per monomeric unit, and one or more second monomeric units, each independently comprising at least one pendant linear $(C_5-C_{50})$alkyl-polyether group per monomeric unit, the polymer having a weight average molecular weight of greater than or equal to about 30,000 to 10,000,000 g/mol, typically about 30,000 to 500,000 g/mol, more typically 50,000 g/mol to 500,000 grams per mole.

Typically the first and second specialty hydrophobic macro monomeric units (a)(b) of the polyanionic HASE POLYMER are attached to the backbone comprising the at least one polymerizable functional group per molecule of polymer.

Typically the HASE polymer comprises third acid monomeric units, each independently comprising at least one acid grouoop per monomeric unit, for example, a sulfate group, a sulfonic acid group, a phosphate group, a phosphonic acid group, a phosphoric acid group, or a carboxylic acid-functional substituent group, for example, Methacrylic Acid (MAA).

Figure 3:
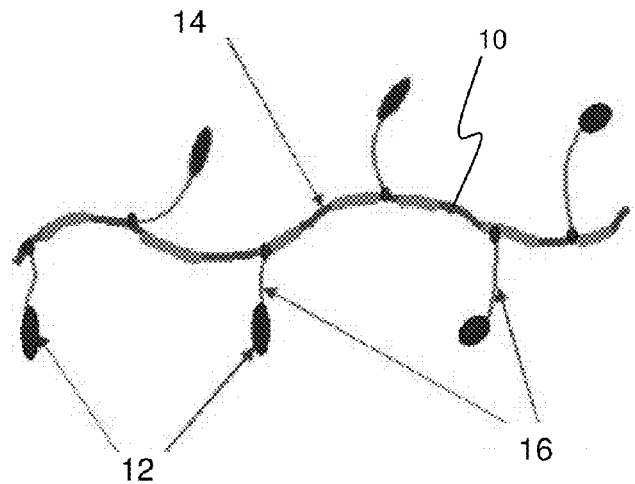
FIG. 3 shows an idealized diagram of the structure of HASE polymer.

Typically the HASE polymer comprises fourth non-ionic monomeric units, each independently comprising a nonionic substituent group, for example ethyl acrylate (EA). A monomeric unit of ethylene oxide (EO) and/or propylene oxide (PO) typically connects the hydrophobic macro groups to the backbone as side chains. The MAA hydrophilic segments provide solubility. The slightly insoluble EA segments enhance the thickening performance by promoting hydrophobic aggregations. The hydrophobic macro monomers are specialty monomers responsible for intra-/intermolecular associations. The poly(ethylene oxide) chain, usually 5-100 ethylene oxide units (typically 6-10 EO groups) and 0-5 propylene oxide units favor the intermolecular aggregation. FIG. 3 shows an idealized diagram of a typical HASE polymer 10 in which the hydrophobic macro groups 12 are the side chains linked to a backbone 14 by PEO Spacers 16, and the EA, MAA and hydrophobic macro groups are in the backbone 14.

First Monomeric Unit for HASE Polymer

In one embodiment, the first monomeric units each independently comprise, per monomeric unit, at least one branched $(C_5-C_{50})$alkyl or bicycloheptyl-polyether or bicycloheptenyl-polyether group according to structure (A.I):

$$—R^{14}—R^{13}—R^{12}—R^{11} \quad\quad (A.I)$$

In one embodiment, $R^{11}$ is bicyclo[d.e.f]heptyl or bicyclo[d.e.f]heptenyl, wherein d is 2, 3, or 4, e is 1 or 2, f is 0 or 1, and the sum of d+e+f=5, and wherein the bicyclo[d.e.f]heptyl or bicyclo[d.e.f]heptenyl may, optionally, be substituted on one or more of the ring carbon atoms by one or more $(C_1-C_6)$alkyl groups, $R^{12}$ is absent or is a bivalent linking group, $R^{13}$ is bivalent polyether group, and $R^{14}$ is absent or is a bivalent linking group.

Suitable bicycloheptyl- and bicycloheptenyl-moieties may be derived from, for example, terpenic compounds having core (non-substituted) 7 carbon atom bicyclic ring systems according to structures (A.II)-(A.V.b):

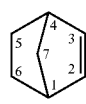

[2.2.1]

(A.II)

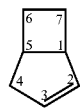

[3.2.0]

(A.III)

[3.1.1]

(A.IV.a)

[3.1.1.]

(A.IV.b)

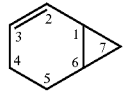

[4.1.0]

(A.V.a)

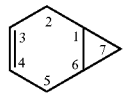

[4.1.0]

(A.V.b)

In one embodiment, $R^{11}$ is bicyclo[d.e.f]heptyl or bicyclo[d.e.f]heptenyl wherein d is 2, 3, or 4, e is 1 or 2, f is 0 or 1, and the sum of d+e+f=5, and which may, optionally, be substituted on one or more of the ring carbon atoms by one or more $(C_1-C_6)$alkyl groups.

More typically, $R^{11}$ is:

a bicyclo[2.2.1]heptyl or bicyclo[2.2.1]heptenyl group bonded to $R^2$, if present, or to $R^3$, if $R^2$ is not present, via its carbon atom at the 2-position or 3-position and is typically substituted on its carbon atom at the 7 position by one or two $(C_1-C_6)$alkyl radicals, more typically by two methyl radicals, or a bicyclo[3.1.1]heptyl or bicyclo[3.1.1]heptenyl group bonded to $R^2$, if present, or to $R^3$, if $R^2$ is not present, via its carbon atom at the 2-position or 3-position and is typically substituted on its carbon atom at the 6-position or 7-position by one or two $(C_1-C_6)$alkyl radicals, more typically by two methyl radicals.

In one embodiment, $R^{11}$ is branched $(C_5-C_{50})$ alkyl group, more typically a branched alkyl group according to structure (A.VI):

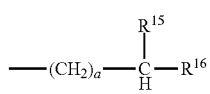

(A.VI)

wherein:

$R^{15}$ and $R^{16}$ are each independently $(C_1-C_{48})$alkyl, and a is an integer of from 0 to 40, provided that $R^{11}$, that is, $R^{15}$, $R^{16}$ and the $—(CH_2)_a—$ radical taken together, comprises a total of from about 5 to about 50, more typically about 12 to about 50, carbon atoms;

$R^{12}$ is absent or is a bivalent linking group,
$R^{13}$ is bivalent polyether group, and
$R^{14}$ is absent or is a bivalent linking group.

More typically, $R^{12}$ is O, a bivalent hydrocarbon group, even more typically a methylene group or chain of from 2 to 6 methylene units, or a bivalent alkyleneoxyl group, such as ethyleneoxy. In one embodiment, $R^{12}$ is according to structure (A.VII):

$$—(CH_2)_b—A— \quad (A.VII)$$

wherein A is O or absent, and b is an integer of from 1 to 6.

More typically, $R^{13}$ is a bivalent polyether group comprising a linear chain of from 2 to 100 units, each of which may independently be $(C_2-C_4)$oxyalkylene, more typically, $(C_2-C_3)$oxyalkylene. In one embodiment, $R^{13}$ is a bivalent polyether group comprising a chain of from 2 to 100 polymerized oxyethylene units and oxypropylene units, which may be arranged alternately, randomly, or in blocks. In one embodiment, $R^{13}$ is a bivalent polyether group comprising a block of polyoxyethylene units and a block of oxypropylene units, more typically, a block of polyoxyethylene units and a block of oxypropylene units, wherein the block of oxypropylene units is disposed between and links the block of oxyethylene units and the $R^{12}$ substituent, if present, or the $R^{11}$ substituent, if $R^{12}$ is not present.

In one embodiment, $R^{13}$ is according to structure (A.VIII):

$$—[(C_gH_{2g}O)_i—(C_hH_{2h}O)_j]_k— \quad (A.VIII)$$

wherein:
g and h are independently integers of from 2 to 5, more typically 2 or 3,
each i is independently an integer of from 1 to about 80, more typically from 1 to about 50,
each j is independently an integer of from 0 to about 80, more typically from 1 to about 50,
k is an integer of from 1 to about 50, provided that the product obtained by multiplying the integer k times the sum of i+j is from 2 to about 100.

If i≠0, j≠0, and g≠0, the respective —$(C_pH_{2p}O)$— and —$(C_qH_{2q}O)$-oxylakylene units may be arranged randomly, in blocks, or in alternating order.

In one embodiment,
g=2,
h=3,
i is an integer of from 1 to 50, more typically 10 to 40, and even more typically from 15 to about 30,
j is an integer of from 1 to 30, more typically from 2 to 20, and even more typically from about 2 to about 10, and
k=1.

In one embodiment, $R^{14}$ is O, —$(CH_2)_n$—O—, or is according to structure (A.IX):

$$—\overset{\overset{O}{\|}}{C}—A— \quad (A.IX)$$

wherein:
n is an integer of from 1 to 6,
A is O or $NR^{17}$, and
$R^{17}$ is H or $(C_1-C_4)$alkyl.

The first monomeric units may be made by known synthetic techniques, such as, for example, by grafting of one or more groups according to structure (I) onto a polymer backbone, such as a hydrocarbon polymer backbone, a polyester polymer backbone, or a polysaccharide polymer backbone, or by copolymerization, with, for example, the second monomer and third monomer described below, of at least one first monomer selected from monomers that comprise a reactive functional group and at least one group according to structure (A.I) per molecule.

In one embodiment, the first monomeric units are derived from at least one first monomer selected from monomers that comprise a reactive functional group and at least one group according to structure (A.I) per molecule.

In one embodiment, the reactive functional group of the first monomer is an ethylenically unsaturated group and the first monomer selected from ethylenically unsaturated monomers that comprise at least one site of ethylenic unsaturation, more typically, an α-, β-unsaturated carbonyl moiety, and least one group according to structure (A.I) per molecule.

In one embodiment, the first monomer comprises one or more compounds according to structure (A.X):

$$R^{18}—R^{14}—R^{13}—R^{12}—R^{11} \quad (A.X)$$

wherein:
$R^{11}$, $R^{12}$, $R^{13}$, and $R^{14}$ are each as described above, and
$R^{18}$ is a moiety having a site of ethylenic unsaturation.

In one embodiment, the compound according to structure (X) is an α-, β-unsaturated carbonyl compound.

In one embodiment, $R^{18}$ is according to structure (A.XI):

$$CH_2{=}\underset{R^{19}}{\overset{}{C}}— \quad (A.XI)$$

wherein $R^{19}$ is H or $(C_1-C_4)$alkyl.

In one embodiment, the first monomer selected from monomers according to structure (A.XII):

$$CH_2{=}\underset{R^{19}}{\overset{}{C}}—\overset{\overset{O}{\|}}{C}—O—[(C_gH_{2g}O)_i—(C_hH_{2h}O)_j]_k—(CH_2)_b—R^{11} \quad (A.XII)$$

wherein:
$R^{11}$ is bicyclo[d.e.f]heptyl or bicyclo[d.e.f]heptenyl wherein d is 2, 3, or 4, e is 1 or 2, f is 0 or 1, and the sum of d+e+f=5, and which may, optionally, be substituted on one or more of the ring carbon atoms by one or more $(C_1-C_6)$alkyl groups, and
$R^{19}$, b, g, h, i, j, and k are each as defined above.

In one embodiment, the first monomer comprises one or more compounds with a Nopol component according to structure (A.XIII):

$$CH_2{=}\underset{R^{19}}{\overset{}{C}}—\overset{\overset{O}{\|}}{C}—O—(C_2H_4O)_i—(C_3H_6O)_j—CH_2CH_2—\text{[nopol bicyclic group]} \quad (A.XIII)$$

wherein i, j, and $R^{19}$ are each as described above, and, more typically, i is an integer of from 10 to 40, and even more typically from 15 to about 30, or from about 20 to about 30, and j is an integer of from 1 to 20, and even more typically from about 2 to about 10. This chemistry is more tolerant to salts than others.

In another embodiment, the first monomer comprises one or more compounds according to structure (A.XIV):

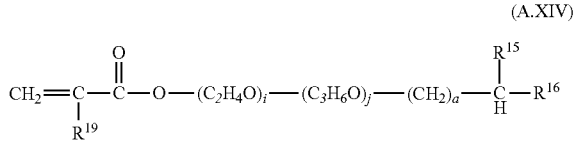

(A.XIV)

wherein a, i, j, and $R^{15}$, $R^{16}$, and $R^{19}$ are each as described above.

Suitable monomer may be made by known synthetic methods. For example, a bicycloheptenyl intermediate compound (A.XV), known as "Nopol":

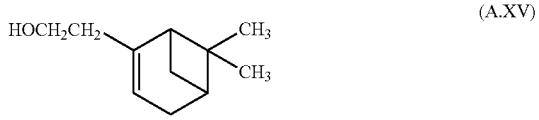

(A.XV)

is made by reacting β-pinene with formaldehyde, and a bicycloheptyl intermediate compound (A.XVI), known as "Arbanol":

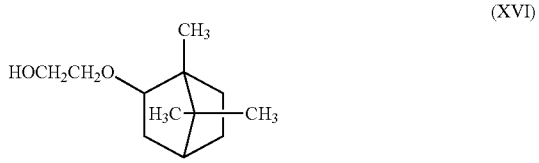

(XVI)

is made by isomerization of α-pinene to camphene and ethoxyhydroxylation of the camphene.

The bicycloheptyl- or bicycloheptenyl-intermediate may then be alkoxylated by reacting the bicycloheptyl- or bicycloheptenyl intermediate with one or more alkylene oxide compounds, such as ethylene oxide or propylene oxide, to form a bicycloheptyl-, or bicycloheptenyl-polyether intermediate. The alkoxylation may be conducted according to well known methods, typically at a temperature in the range of about 100° to about 250° C. and at a pressure in the range of from about 1 to about 4 bars, in the presence of a catalyst, such as a strong base, an aliphatic amine, or a Lewis acid, and an inert gas, such as nitrogen or argon.

The bicycloheptyl-, or bicycloheptenyl-polyether monomer may then be formed from the bicycloheptyl- or bicycloheptenyl-polyether intermediate by addition of a moiety containing an ethylenically unsaturated group to the bicycloheptyl- or bicycloheptenyl-polyether intermediate, by, for example, esterification, under suitable reaction conditions, of the bicycloheptyl- or bicycloheptenyl-polyether intermediate with, for example, methacrylic anhydride.

Alternatively, a monomer comprising a ethylenically unsaturated group, such as for example, a polyethylene glycol monomethacrylate, which may optionally be further alkoxylated, may be reacted with the bicycloheptyl- or bicycloheptenyl-intermediate to form the bicycloheptyl-, or bicycloheptenyl-polyether monomer.

Preferable HASE polymers have a POx and EOx alkoxylation on the Nopol components, for example x from 1 to 200, e.g., 1 to 30 or 5 to 30. In addition, an added crosslinker is preferably employed to even increase viscosity.

Second Monomeric Unit for HASE Polymer

In one embodiment, the second monomeric units each independently comprise, per monomeric unit, at least one group according to structure (A.XVII):

(A.XVII)

wherein:

$R^{21}$ is linear or branched $(C_5-C_{50})$alkyl, hydroxyalkyl, alkoxyalkyl, aryl, or aryalkyl, $R^{22}$ is a bivalent polyether group, $R^{23}$ is absent or is a bivalent linking group.

In one embodiment, $R^{21}$ is linear or branched $(C_5-C_{40})$ alkyl, more typically linear or branched $(C_{10}-C_{40})$alkyl, even more typically, linear or branched $(C_{16}-C_{40})$alkyl, and still more typically linear or branched $(C_{16}-C_{30})$alkyl. In one embodiment, $R^{21}$ is tridecyl, tetradecyl, pentadecyl, hexadecyl, heptadecyl, octadecyl, nonadecyl, eicosyl, heneicosyl, behenyl, tricosyl, tetracosyl, pentacosyl, hexacosyl, heptacosyl, octacosyl, nonacosyl, triacontyl, dotriacontyl, tritriacontyl, tetratriacontyl, pentatriacontyl, hexatriacontyl, heptatriacontyl, octatriacontyl, nonatriacontyl, or tetracontyl, more typically, hexadecyl, heptadecyl, octadecyl, nonadecyl, eicosyl, or behenyl.

In one embodiment $R^{21}$ is hydroxyalkyl, such as, for example, hydroxyhexadecyl, hydroxyoctadecyl, or hydroxyeicosyl, or alkoxyalkyl, such as for example, methoxyhexadecyl, methoxyoctadecyl, or methoxyeicosyl.

In embodiment $R^{21}$ is aryl, such as, for example, phenyl, methylphenyl, methoxyphenyl, dibutylphenyl, triisobutylphenyl, or tristyrylphenyl, or aralkyl, such as phenylmethyl, phenylethyl, or triphenylmethyl.

In one embodiment, the second monomeric units each independently comprise at least one group according to structure (A.XVII) above wherein $R^{21}$ is a linear $(C_5-C_{50})$alkyl group.

In one embodiment, the second monomeric units each independently comprise at least one group according to structure (A.XVII) above wherein $R^{21}$ is a branched $(C_5-C_{50})$alkyl group, more typically a branched $(C_5-C_{50})$alkyl group according to structure (A.VI) above.

In one embodiment, the second monomeric units comprise a mixture of second monomeric units that each independently comprise at least one group according to structure (A.XVII) above wherein $R^{21}$ is a linear $(C_5-C_{50})$alkyl group and second monomeric units that each independently comprise at least one group according to structure (A.XVII) above wherein $R^{21}$ is a branched $(C_5-C_{50})$alkyl group, more typically a branched $(C_5-C_{50})$alkyl group according to structure (A.VI) above.

In one embodiment, $R^{22}$ is a bivalent polyether group comprising a linear chain of from 2 to 100 units, each of which may independently be $(C_2-C_4)$oxyalkylene, more typically, $(C_2-C_3)$oxyalkylene. In one embodiment, $R^{22}$ is a bivalent polyether group comprising a chain of from 2 to 100 polymerized oxyethylene units.

In one embodiment, $R^{22}$ is according to structure (A.XVIII):

(A.XVIII)

wherein:

p and q are independently integers of from 2 to 5, more typically 2 or 3, each r is independently an integer of from 1 to about 80, more typically from 1 to about 50, each s is independently an integer of from 0 to about 80, more typically from 0 to about 50, t is an integer of from 1 to about 50, provided that the product obtained by multiplying the integer t times the sum of r+s is from 2 to about 100.

If r≠0, s≠0, and p≠q, the respective —($C_pH_{2p}O$)- and —($C_qH_{2q}O$)-oxylakylene units may be arranged randomly, in blocks, or in alternating order.

In one embodiment, p=2, q=3, r is an integer of from 1 to 50, more typically 5 to 45, and even more typically from 10 to about 40, s is an integer of from 1 to 30, more typically from 2 to 20, and even more typically from about 2 to about 10, and t=1

In another embodiment, p=2, r is an integer of from 1 to 50, more typically 5 to 45, and even more typically from 10 to about 40, s is 0, and t=1.

In one embodiment, $R^{23}$ is O, —$(CH_2)_n$—O— wherein n is an integer of from 1 to 6, or is according to structure (A.IX) above, wherein A is O or $NR^{17}$, and $R^{17}$ is H or ($C_1$-$C_4$)alkyl.

The second monomeric units may be made by known synthetic techniques, such as, for example, by grafting of one or more groups according to structure XVII onto a polymer backbone, such as a hydrocarbon polymer backbone, a polyester polymer backbone, or a polysaccharide polymer backbone, or by copolymerization, with, for example, the above-described first monomer and the third monomer described below, of at least one second monomer selected from monomers that comprise a reactive functional group and at least one group according to structure (A.XVII) per molecule and that are copolymerizable with the first monomer.

In one embodiment, the second monomeric units are derived from at least one second monomer that comprises a reactive functional group and at least one group according to structure (A.XVII) per molecule and that are copolymerizable with the first monomer.

In one embodiment, the reactive group of the second monomer is an ethylenically unsaturated group and the second monomer is an ethylenically unsaturated monomer comprises at least one site of ethylenic unsaturation, more typically, an α-, β-unsaturated carbonyl moiety, and at least one group according to structure (A.XVII) per molecule and that are copolymerizable with the first monomer.

In one embodiment, the second monomer comprises one or more compounds according to structure (A.XIX):

$$R^{24}—R^{23}—R^{22}—R^{21} \quad (A.XIX)$$

wherein:

$R^{21}$, $R^{22}$, and $R^{23}$ are each as described above, and $R^{24}$ is a moiety having a site of ethylenic unsaturation.

In one embodiment, the compound according to structure (A.XIX) is an α-, β-unsaturated carbonyl compound. In one embodiment, $R^{23}$ is according to structure (A.XI) above.

In one embodiment, the second monomer comprises one or more compounds according to structure (A.XX):

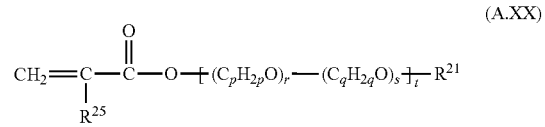

(A.XX)

wherein $R^{21}$ is linear or branched ($C_5$-$C_{50}$)alkyl, hydroxyalkyl, alkoxyalkyl, aryl, or aralkyl, $R^{25}$ is methyl or ethyl, and p, q, r, s, and t are each as described above.

In one embodiment, the second monomer comprises one or more compounds according to structure (A.XX) wherein $R^{21}$ is linear ($C_{16}$-$C_{22}$)alkyl.

In one embodiment, the second monomer comprises one or more compounds according to structure (A.XX) wherein $R^{21}$ is a branched ($C_5$-$C_{50}$)alkyl group, more typically a branched ($C_5$-$C_{50}$)alkyl group according to structure (A.VI) above.

In one embodiment, the second monomer comprises one or more compounds according to structure (A.XX) wherein p=2, s=0, and t=1.

In one embodiment, the second monomer comprises one or more compounds according to structure (A.XX) wherein $R^{21}$ is linear ($C_{16}$-$C_{22}$)alkyl, $R^{24}$ is methyl or ethyl, p=2, s=0, and t=1.

For example, a suitable second monomer is shown in Formula A.XXa.

$$CH_2{=}C(CH_3)—C(O)—(OC_2H_4)_{25}—O—R_{21} \quad A.XXa,$$

wherein $R^{21}$ is a branched ($C_5$-$C_{50}$)alkyl group, more typically a branched ($C_5$-$C_{50}$)alkyl group according to structure (A.VI) above.

Suitable ethylenically unsaturated second monomers include:

alkyl-polyether (meth)acrylates that comprise at least one linear or branched ($C_5$-$C_{40}$)alkyl-polyether group per molecule, such as hexyl polyalkoxylated (meth)acrylates, tridecyl polyalkoxylated (meth)acrylates, myristyl polyalkoxylated (meth)acrylates, cetyl polyalkoxylated (meth)acrylates, stearyl polyalkoxylated (methyl)acrylates, eicosyl polyalkoxylated (meth)acrylates, behenyl polyalkoxylated (meth) acrylates, melissyl polyalkoxylated (meth)acrylates, tristyrylphenoxyl polyalkoxylated (meth)acrylates, and mixtures thereof, alkyl-polyether (meth)acrylamides that comprise at least one ($C_5$-$C_{40}$)alkyl-polyether substituent group per molecule, such as hexyl polyalkoxylated (meth)acrylamides, tridecyl polyalkoxylated (meth) acrylamides, myristyl polyalkoxylated (meth) acrylamides, cetyl polyalkoxylated (meth)acrylamides, stearyl polyalkoxylated (methyl)acrylamides, eicosyl polyalkoxylated (meth) acrylamides, behenyl polyalkoxylated (meth) acrylamides, melissyl polyalkoxylated (meth) acrylamides and mixtures thereof.

alkyl-polyether vinyl esters, alkyl-polyether vinyl ethers, or alkyl-polyether vinyl amides that comprise at least one ($C_5$-$C_{40}$)alkyl-polyether substituent group per molecule such as vinyl stearate polyalkoxylate, myristyl polyalkoxylated vinyl ether, and mixtures thereof, as well as mixtures of any of the above alkyl-polyether acrylates, alkyl-polyether methacrylates, alkyl-polyether acrylamides, alkyl-polyether methacrylamides, alkyl-polyether vinyl esters, alkyl-polyether vinyl ethers, and/or alkyl-polyether vinyl amides.

In one embodiment, the second monomer comprises one or more alkyl-polyalkoxylated (meth)acrylates that comprise one linear or branched ($C_5$-$C_{40}$)alkyl-polyethoxylated group, more typically ($C_{10}$-$C_{22}$)alkyl-polyethoxylated group per molecule, such as decyl-polyethoxylated (meth)acrylates, tridecyl-polyethoxylated (meth)acrylates, myristyl-polyethoxylated (meth)acrylates, cetyl-polyethoxylated (meth)acrylates, stearyl-polyethoxylated (methyl)acrylates, eicosyl-polyethoxylated (meth)acrylates, behenyl-polyethoxylated (meth)acrylates, even more typically decyl-polyethoxylated methacrylates, tridecyl-polyethoxylated methacrylates, myristyl-polyethoxylated methacrylates, cetyl-polyethoxylated methacrylates, stearyl-polyethoxylated methylacrylates, eicosyl-polyethoxylated methacrylates, behenyl-polyethoxylated methacrylates, and mixtures thereof.

Third Monomeric Unit for HASE Polymer

In one embodiment, the anionic polymer employed in the present invention further comprises third monomeric units, each independently comprising at least one acid group per monomeric unit. The acid group makes the HASE polymer anionic. HASE polymers are synthesized using methacrylic acid and such monomer contains carboxylic groups which at high pH, e.g., about 7 or more, form negative charges.

In one embodiment, the third monomeric units each independently comprise, per monomeric unit, at least one group according to structure (A.XXI):

$$—R^{32}—R^{31} \qquad \text{(A.XXI)}$$

wherein
$R^{31}$ is a moiety that comprises at least one carboxylic acid, sulfonic acid, phosphonic acid, or phosphoric acid group, and
$R^{32}$ is absent or is a bivalent linking group.

In one embodiment, $R^{32}$ is O, —$(CH_2)_n$—O—, or is according to structure (IX) above, wherein n is an integer of from 1 to 6, A is O or $NR^{17}$, and $R^{17}$ is H or ($C_1$-$C_4$)alkyl.

In one embodiment, the third monomeric units each independently comprise one or two carboxy groups per monomeric unit and may, if the third monomeric unit comprises a single carboxy group, further comprise an ester group according to —$CH_2COOR^{33}$, wherein $R^{33}$ is alkyl, more typically, ($C_1$-$C_6$)alkyl.

The third monomeric units may be made by known synthetic techniques, such as, for example, by grafting of one or more groups according to structure (XXI) onto a polymer backbone, such as a hydrocarbon polymer backbone, a polyester polymer backbone, or a polysaccharide polymer backbone, or by polymerization, with, for example, the above described first and second monomers, of at least one third monomer selected from monomers that comprise a reactive functional group and at least one group according to structure (A.XXI) per molecule, and that are copolymerizable with the first and second monomers.

In one embodiment, the third monomeric units are derived from at least one third monomer that comprises a reactive functional group and at least group according to structure (A.XXI) per molecule and is copolymerizable with the first and second monomers.

In one embodiment, the reactive functional group of the third monomer is an ethylenically unsaturated group and the third monomer is an ethylenically unsaturated monomer that comprises at least one site of ethylenic unsaturation, more typically, an α-, β-unsaturated carbonyl moiety, and at least one group according to structure (A.XXI) per molecule and is copolymerizable with the first and second monomers.

In one embodiment the third monomer comprises one or more ethylenically unsaturated monocarboxylic acid monomers according to structure (A.XXII):

$$R^{34}—R^{32}—R^{31} \qquad \text{(A.XXII)}$$

wherein:
$R^{31}$ and $R^{32}$ are each as described above, and
$R^{34}$ is a moiety having a site of ethylenic unsaturation.

In one embodiment, the compound according to structure (XXII) is an α-, β-unsaturated carbonyl compound. In one embodiment, $R^{34}$ is according to structure (A.XI) above.

Suitable third monomers include, for example, ethylenically unsaturated carboxylic acid monomers, such as acrylic acid and methacrylic acid, ethylenically unsaturated dicarboxylic acid monomers, such ac maleic acid and fumaric acid, ethylenically unsaturated alkyl monoesters of dicarboxylic acid monomers, such as butyl methyl maleate, ethylenically unsaturated sulphonic acid monomers, such as vinyl sulfonic acid 2-acrylamido-2-methylpropane sulfonic acid, and styrene sulfonic acid, and ethylenically unsaturated phosphonic acid monomers, such as vinyl phosphonic acid and allyl phosphonic acid, salts of any thereof, and mixtures of any thereof. Alternatively, corresponding ethylenically unsaturated anhydride or acid chloride monomers, such as maleic anhydride, may be used and subsequently hydrolyzed to give a pendant moiety having two acid groups.

In one embodiment, the polymer of the present invention comprises third monomeric units derived from one or more third monomers selected from acrylic acid, methacrylic acid, and mixtures thereof. Methacrylic acid having the following formula A.XXIIa:

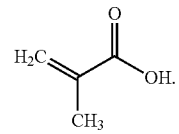

A.XXIIa

Fourth Monomeric Unit for HASE Polymer

In one embodiment, the polymer of the present invention further comprises one or more fourth monomeric units that differ from the first, second and third monomeric units. The fourth monomer could be non-ionic or ionic.

In one embodiment, the fourth monomeric units each independently comprise, per monomeric unit, at least one group according to structure (A.XXIII):

$$—R^{42}—R^{41} \qquad \text{(A.XXIII)}$$

wherein
$R^{41}$ is alkyl, hydroxyalkyl, alkoxyalkyl, cycloalkyl, aryl, aralkyl, or aryloxy, and
$R^{42}$ is absent or is a bivalent linking group.

In one embodiment, $R^{41}$ is ($C_1$-$C_{22}$)alkyl, ($C_1$-$C_{22}$)hydroxyalkyl, ($C_2$-$C_{22}$)alkoxyalkyl, ($C_6$-$C_{24}$)cycloalkyl, ($C_6$-$C_{40}$)aryl, or ($C_7$-$C_{40}$)aralkyl, more typically ($C_2$-$C_{12}$)alkyl.

In one embodiment, $R^{41}$ is ($C_1$-$C_{22}$) alkyl, more typically, ($C_1$-$C_{12}$) alkyl.

In one embodiment, $R^{42}$ is O, —$(CH_2)_n$—O—, wherein n is an integer of from 1 to 6, or is according to structure (A.IX) above, wherein A is O or $NR^{17}$, and $R^{17}$ is H or ($C_1$-$C_4$)alkyl.

The fourth monomeric units may be made by known synthetic techniques, such as, for example, by grafting of one or more groups according to structure (A.XXIII) onto a polymer backbone, such as a hydrocarbon polymer backbone, a polyester polymer backbone, or a polysaccharide polymer backbone, or by polymerization, with, for example, the above described first second, and third monomers, of at least one fourth monomer selected from monomers that comprise a reactive functional group and at least one group according to structure (A.XXIII) per molecule and that are copolymerizable with the first, second, and third monomers. Alternatively, the fourth monomeric units may simply be non-grafted portions of a polymer backbone, other portions of which have been grafted with groups according to structures (A.I), (A.XVII), and (A.XXI).

In one embodiment, the fourth monomeric units are derived from a fourth monomer that comprises a reactive functional group and a group according to structure (A.XXIII), and is copolymerizable with the first, second and third monomers.

In one embodiment, the reactive functional group of the fourth monomer is an ethylenically unsaturated group and the fourth monomer is an ethylenically unsaturated monomer comprising at least one site of ethylenic unsaturation, more typically, an α-, β-unsaturated carbonyl moiety and at least one group according to structure (A.XXIII) per molecule.

In one embodiment, the fourth monomer comprises one or more compounds according to structure (A.XXIV):

$$R^{43}-R^{42}-R^{41} \quad (A.XXIV)$$

wherein:
$R^{41}$ and $R^{42}$ are each as described above, and
$R^{43}$ is a moiety having a site of ethylenic unsaturation.

In one embodiment, the compound according to structure (A.XXIV) is an α-, β-unsaturated carbonyl compound. In one embodiment, $R^{43}$ is according to structure (A.XI) above.

Suitable fourth monomers include unsaturated monomers at least one group according to structure A.XXIII per molecule, including (meth)acrylic esters such as: methyl (meth)acrylate, ethyl (meth)acrylate, butyl (meth)acrylate, isobutyl (meth)acrylate, cyclohexyl(meth)acrylate, 2-ethylhexyl (meth)acrylate, isodecyl(meth)acrylate, lauryl(meth)acrylate isobornyl(meth)acrylate, benzyl(meth)acrylate, hydroxyethyl(meth)acrylate, hydroxypropyl(meth)acrylate, methoxyethyl(meth)acrylate, ethoxyethyl(meth)acrylate, phenoxyethyl(meth)acrylate, tetrahydrofurfuryl(meth)acrylate, glycidyl(meth)acrylate, dimethylaminoethyl(meth)acrylate, diethylaminoethyl(meth)acrylate, tert-butylaminoethyl (meth)acrylate, and acetoxyethyl(meth)acrylate, (meth)acrylamides such as, (meth)acrylamide, N-methylol (meth)acrylamide, N-butoxyethyl(meth)acrylamide, N,N-dimethyl (meth)acrylamide, N-isopropyl(meth)acrylamide, N-tert-butyl(meth)acrylamide, N-tert-octyl(meth)acrylamide, and diacetone(meth)acrylamide, vinyl esters such as vinyl acetate, vinyl propionate, vinyl 2-ethylhexanoate, N-vinylamides such as: N-vinylpyrrolidione, N-vinylcaprolactam, N-vinylformamide, and N-vinylacetamide, and vinyl ethers such as, methyl vinyl ether, ethyl vinyl ether, butyl vinyl ether, and hydroxybutyl vinyl ether, and ethylenically unsaturated aryl compounds, such as styrene.

In one embodiment, the polymer of the present invention is crosslinked. A crosslinked polymer can be made by, for example, reacting a mixture of first, second, and third monomers that also includes at least one fourth monomer having more than one reactive functional group, such as for example, more than one site of ethylenic unsaturation per molecule, that are copolymerizable with the other monomers of mixture In one embodiment, the fourth monomer comprises least one monomeric compound having more than one (meth)acrylic group per molecule, such as, for example, allyl methacrylate, ethylene glycol dimethacrylate, butylene glycol dimethacrylate, diallyl pentaerythritol, methylenebisacrylamide, pentaerythritol di-, tri- and tetra-acrylates, divinyl benzene, polyethylene glycol diacrylates, bisphenol A diacrylates, butanediol dimethacrylate, 2,2-dimethylpropanediol dimethacrylate, ethylene glycol dimethacrylate, phenylene diacrylate, or a mixture thereof. Ethyl acrylate having the formula A.XXIVa:

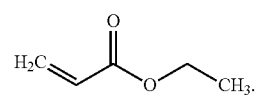

A.XXIVa

Ethylene glycol dimethyl acrylate having the following formula A.XXIVb.

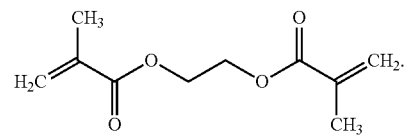

A.XXIVb

In one embodiment, the polymer of the present invention comprises fourth monomeric units derived from one or more $(C_1-C_{22})$alkyl (meth)acrylic esters, more typically $(C_1-C_{12})$ alkyl(meth)acrylic esters, such as ethyl acrylate, butyl methacrylate, or ethylhexyl acrylate.

Particular Monomeric Unit Combinations for HASE Polymer

In one embodiment, the polymer of the present invention comprises:
one or more first monomeric units,
one or more second monomeric units,
one or more third monomeric units, and
one or more fourth monomeric units,
each as described above.

In one embodiment of the polymer of the present invention:
the first monomeric units each independently comprise at least one bicycloheptyl-polyether, bicycloheptenyl-polyether or branched $(C_5-C_{50})$alkyl-polyether group per monomeric unit, wherein the bicycloheptyl-polyether or bicycloheptenyl-polyether group may, optionally, be substituted on one or more ring carbon atoms by one or two $(C_1-C_6)$alkyl groups per carbon atom,
the second monomeric units each independently comprise at least one pendant linear or branched $(C_5-C_{50})$alkyl-polyether group per monomeric unit, provided that the first and second monomeric units cannot both comprise a branched $(C_5-C_{50})$alkyl-polyether group,
the third monomeric units each independently comprise at least one carboxylic acid, sulfonic acid, phosphonic acid or phosphoric acid group per molecule, and
the fourth monomeric units each independently comprise at least one alkyl, hydroxyalkyl, alkoxyalkyl, cycloalkyl, aryl, aralkyl, or aryloxy group per monomeric unit.

A typical phosphonic acid group would be as in Formula A.XXV:

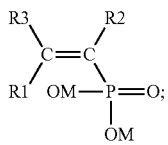

A.XXV wherein the R1, R2 and R3 can be the same or different and can be hydrogen, C1-C4 lower alkyl, or combinations thereof. The value of n is 5 to 2000, preferably 10 to 1500, and more preferably 20 to 1000. R2 can also be —P(O$_3$M$_2$). M represents hydrogen, or an alkali metal such as sodium or potassium. The preferred substituent for M is sodium (Na$^+$), potassium (K$^+$), lithium (Li$^+$), ammonium (NH4$^+$), phosphate (PR$_4^+$ where R is alkyl or aryl) or phosphonate (C—PO(OH)$_2$ or C—PO(OR)$_2$ groups where R is alkyl, aryl).

In one embodiment:
the first monomeric units each independently comprise at least one bicycloheptyl-polyether or bicycloheptenyl-polyether group, which may, optionally, be substituted on one or more ring carbon atoms by one or two (C$_1$-C$_6$)alkyl groups per carbon atom, per monomeric unit, the second monomeric units, each independently comprise at least one pendant linear or branched (C$_5$-C$_{50}$)alkyl-polyether group per monomeric unit, the third monomeric units each independently comprise at least one carboxylic acid, sulfonic acid, or phosphoric acid, more typically carboxylic acid, group per molecule, and the fourth monomeric units each independently comprise at least one alkyl, more typically (C$_1$-C$_{22}$)alkyl, group per monomeric unit.

In one embodiment, the polymer of the present invention comprises, based on 100 monomeric units, from about 0.01, more typically from about 0.05, and even more typically from about 0.10 of the first monomeric units, to about 10, more typically to about 5, and even more typically to about 2, of the first monomeric units, from about 0.01, more typically from about 0.05, and even more typically from about 0.10 of the second monomeric units, to about 10, more typically to about 5, and even more typically to about 2, of the second monomeric units, and from about 25, more typically from about 30, and even more typically from about 35 of the third monomeric units, to about 70, more typically to about 65, and even more typically to about 60, of the third monomeric units, from about 30, more typically from about 40, and even more typically from about 45 of the fourth monomeric units, to about 75, more typically to about 70, and even more typically to about 65 of the fourth monomeric units.

In one embodiment, the polymer of the present invention comprises, based on 100 pbw of the polymer, from about 0.1, more typically from about 0.5, and even more typically from about 1.0 pbw of the first monomeric units, to about 20, more typically to about 15, and even more typically to about 10, pbw of the first monomeric units, from about 0.1, more typically from about 0.5, and even more typically from about 1.0, pbw of the second monomeric units, to about 20, more typically to about 15, and even more typically to about 10, pbw of the second monomeric units, and from about 20, more typically from about 25, and even more typically from about 30, pbw of the third monomeric units, to about 60, more typically to about 55, and even more typically to about 60, pbw of the third monomeric units, and from about 25, more typically from about 35, and even more typically from about 40, pbw of the fourth monomeric units, to about 70, more typically to about 65, and even more typically to about 60, pbw of the fourth monomeric units.

In one embodiment, the polymer of the present invention comprises from about 0.4 to about 5, more typically from about 0.6 to about 4, and even more typically from about 0.8 to about 2 of the first monomeric units per each of the second monomeric units.

Particular Monomer Mixtures for HASE Polymer

In one embodiment, the anionic polymer is the product of copolymerization of a mixture of monomers, comprising:
one or more first monomers,
one or more second monomers,
one or more third monomers, and
one or more fourth monomers,
each as described above.

In particular for this embodiment, the anionic polymer is the product of copolymerization of a mixture of monomers, comprising:

one or more first monomers, each independently selected from monomers that comprise a reactive functional group and at least one bicycloheptyl-polyether, bicycloheptenyl-polyether, or branched (C$_5$-C$_{50}$)alkyl-polyether group per molecule, wherein the bicycloheptyl-polyether or bicycloheptenyl-polyether group may optionally be substituted on one or more ring carbon atoms by one or two (C$_1$-C$_6$)alkyl groups per carbon atom, and one or more second monomers, each independently selected from monomers that comprise a reactive functional group and at least one pendant straight or branched (C$_5$-C$_{50}$) alkyl-polyether group per molecule and that are copolymerizable with the first monomer, provided that the first and second monomers cannot both comprise a branched (C$_5$-C$_{50}$) alkyl-polyether group;

at least one third monomer providing at least one polymerizable acid functional group per molecule of polymer;

the polymer having a weight average molecular weight of greater than or equal to about 30,000 grams per mole.

In one embodiment:
the one or more first monomers are each independently selected from monomers that comprise a reactive functional group and at least one bicycloheptyl-polyether, bicycloheptenyl-polyether, or branched (C$_5$-C$_{50}$)alkyl-polyether group per molecule, wherein the bicycloheptyl-polyether or bicycloheptenyl-polyether group may optionally be substituted on one or more ring carbon atoms by one or two (C$_1$-C$_6$)alkyl groups per carbon atom, the one or more second monomers are each independently selected from monomers that comprise a reactive functional group and at least one pendant straight or branched (C$_5$-C$_{50}$) alkyl-polyether group per molecule and that are copolymerizable with the first monomer, provided that the first and second monomer cannot both comprise a branched (C$_5$-C$_{50}$) alkyl-polyether group, the one or more third monomers are each independently selected from monomers that comprise a reactive functional group and at least one carboxylic acid, sulfonic acid, or phosphoric acid group per molecule and that are copolymerizable with the first and second monomers, and the one or more fourth monomers are each independently selected from monomers that comprise a reactive functional group and at least one alkyl, hydroxyalkyl, alkoxyalkyl, cycloalkyl, aryl, aralkyl, or aryloxy group per monomeric unit and that are copolymerizable with the first, second and third monomers.

In one embodiment, the anionic polymer is the product of copolymerization of a mixture of monomers, comprising:

one or more first monomers, each independently selected from monomers that comprise a reactive functional group and at least one bicycloheptyl-polyether, bicycloheptenyl-polyether, or branched ($C_5$-$C_{50}$)alkyl-polyether group per molecule, wherein the bicycloheptyl-polyether or bicycloheptenyl-polyether group may optionally be substituted on one or more ring carbon atoms by one or two ($C_1$-$C_6$)alkyl groups per carbon atom, and one or more second monomers, each independently selected from monomers that comprise a reactive functional group and at least one pendant straight or branched ($C_5$-$C_{50}$) alkyl-polyether group per molecule and that are copolymerizable with the first monomer, provided that the first and second monomers cannot both comprise a branched ($C_5$-$C_{50}$) alkyl-polyether group;

at least one third monomer providing at least one polymerizable functional group per molecule of polymer;

the polymer having a weight average molecular weight of greater than or equal to about 30,000 grams per mole.

In one embodiment:

the one or more first monomers are each independently selected from monomers that comprise a reactive functional group, more typically an ethylenically unsaturated group, and at least one bicycloheptyl-polyether or bicycloheptenyl-polyether group, which may optionally be substituted on one or more ring carbon atoms by one or two ($C_1$-$C_6$)alkyl groups per carbon atom per molecule, per molecule, the one or more second monomers are each independently selected from monomers that comprise a reactive functional group, more typically an ethylenically unsaturated group, and at least one pendant straight or branched ($C_5$-$C_{50}$)alkyl-polyether group per molecule and that are copolymerizable with the first monomer, the one or more third monomers are each independently selected from monomers that comprise a reactive functional group, more typically an ethylenically unsaturated group, and at least one carboxylic acid, sulfonic acid, or phosphoric acid, more typically, carboxylic acid, group per molecule and that are that are copolymerizable with the first and second monomers, and the one or more fourth monomers are each independently selected from monomers that comprise a reactive functional group, more typically an ethylenically unsaturated group, and at least one alkyl, more typically ($C_1$-$C_{22}$)alkyl, group per molecule unit and that are copolymerizable with the first, second and third monomers.

In one embodiment, the polymer of the present invention is the product of polymerization of a mixture of monomers comprising, based on the molar amount of the monomers:

from about 0.01 mole %, more typically from about 0.05 mole %, and even more typically from about 0.10 mole % of the one or more first monomers, to about 10 mole %, more typically to about 5 mole %, and even more typically to about 2 mole % of the one or more first monomers, from about 0.01 mole %, more typically from about 0.05%, and even more typically from about 0.10 mole %, to about 10 mole %, more typically to about 5 mole %, and even more typically to about 2 mole %, of the one or more second monomers, from about 25 mole %, more typically from about 30 mole %, and even more typically from about 35 mole % of the third monomers to about 70 mole %, more typically to about 65 mole % and even more typically to about 60 mole % of the one or more third monomers, and from about 30, more typically from about 40, and even more typically from about 45, mole % of the fourth monomers, to about 75, more typically to about 70, and even more typically to about 65, mole % of the one or more fourth monomers.

In one embodiment, the polymer of the present invention is the product of polymerization of a mixture of monomers comprising, based on the 100 pbw of the total amount of the monomers:

from about 0.1, more typically from about 0.5, and even more typically from about 1.0 pbw of the first monomers, to about 20, more typically to about 15, and even more typically to about 10, pbw of the one or more first monomers, from about 0.1, more typically from about 0.5, and even more typically from about 1.0, pbw of the second monomers, to about 20, more typically to about 15, and even more typically to about 10, pbw of the one or more second monomers, and from about 20, more typically from about 25, and even more typically from about 30, pbw of the third monomers, to about 60, more typically to about 55, and even more typically to about 50, pbw of the one or more third monomers, and from about 25, more typically from about 35, and even more typically from about 40, pbw of the third monomers, to about 70, more typically to about 65, and even more typically to about 60, pbw of the one or more fourth monomers.

In one embodiment, the polymer comprises the product of polymerization of a mixture of monomers comprising, based on the molar amount of monomers, from about 0.4 to about 5, more typically, from about 0.6 to about 4, and even more typically from about 0.8 to about 2 moles of the one or more first monomers per each mole of the one or more second monomers.

The polyanionic HASE polymer of the present invention can be conveniently prepared from the above-described monomers by known aqueous emulsion polymerization techniques using free-radical initiators, typically in an amount from 0.01 percent to 3 percent, based on the weight of the polymers.

In one embodiment, the polymerization is conducted at a pH of about 5.0 or less. Polymerization at an acid pH of about 5.0 or less permits direct preparation of an aqueous colloidal dispersion having relatively high solids content without the problem of excessive viscosity.

In one embodiment, the polymerization is conducted in the presence of one or more free-radical initiators selected from peroxygen compounds. Useful peroxygen compounds include inorganic persulfate compounds such as ammonium persulfate, potassium persulfate, sodium persulfate, peroxides such as hydrogen peroxide, organic hydroperoxides, for example, cumene hydroperoxide, and t-butyl hydroperoxide, organic peroxides, for example, benzoyl peroxide, acetyl peroxide, lauroyl peroxide, peracetic acid, and perbenzoic acid (sometimes activated by a water-soluble reducing agent such as ferrous compound or sodium bisulfite), and other free-radical producing materials or techniques such as 2,2'-azobisisobutyronitrile and high energy radiation sources.

In one embodiment, the polymerization is conducted in the presence of one or more emulsifiers. Useful emulsifiers include anionic surfactants, nonionic surfactants, amphoteric surfactants, and zwitterionic surfactants. In one embodiment, the emulsion polymerization is conducted in the presence of one or more anionic surfactants. Examples of anionic emulsifiers are the alkali metal alkyl aryl sulfonates, the alkali metal alkyl sulfates and the sulfonated alkyl esters. Specific examples of these well-known emulsifiers are sodium dodecyl benzene sulfonate, sodium dodecyl butylnaphthalene sulfonate, sodium lauryl sulfate, disodium dodecyl diphenyl ether disulfonate, disodium n-octadecyl sulfosuccinamate and sodium dioctyl sulfosuccinate. Known nonionic emulsifiers include, for example, fatty alcohols, alkoxylated fatty alcohols, and alkylpolyglucosides.

The emulsion polymerization may, optionally, be conducted in the presence, in an amount up to about 10 parts per 100 parts of polymerizable monomers, of one or more chain transfer agents. Representative chain transfer agents are carbon tetrachloride, bromoform, bromotrichloromethane, and long-chain alkyl mercaptans and thioesters, such as n-dodecyl mercaptan, t-dodecyl mercaptan, octyl mercaptan, tetradecyl mercaptan, hexadecyl mercaptan, butyl thioglycolate, isooctyl thioglycolate, and dodecyl thioglycolate.

Optionally, other ingredients well known in the emulsion polymerization art may be included, such as chelating agents, buffering agents, inorganic salts and pH adjusting agents.

In one embodiment, the polymerization is carried out at a temperature between about 60° C. and 90° C., but higher or lower temperatures may be used. The polymerization can be conducted batchwise, stepwise, or continuously with batch and/or continuous addition of the monomers, in a conventional manner.

The monomers can be copolymerized in such proportions, and the resulting emulsion polymers can be physically blended, to give products with the desired balance of properties for specific applications. For example, for analogous polymers of a given molecular weight, increasing the amount of first monomer tends to increase the yield strength exhibited by the polymer, increasing the relative amount of second monomer tends to increase the viscosity of the polymer. One or more fourth monomers may be added to adjust the properties of the polymer. For example, the addition of styrene as a fourth monomer tends to increase to a higher pH the adjustment required to dissolve the emulsion in an aqueous coating composition.

These polymeric products prepared by emulsion polymerization at an acid pH are in the form of stable aqueous colloidal dispersions containing the polymer dispersed as discrete particles having average particle diameters of typically about 400 to about 3000 Å and preferably about 600 to about 1750 Å, as measured by light scattering. Dispersions containing polymer particles smaller than about 400 Å are difficult to stabilize, while particles larger than about 3000 Å reduce the ease of dispersion in the aqueous products to be thickened.

In one embodiment, the polymer composition is in the form of an aqueous polymer dispersion, typically having a solids content including the polymer and any surfactants that may be present and based on the total weight of the polymer dispersion, of up to about 60 wt % and, more typically about 20 to about 50 wt %.

Alternatively, these polymers for use in the present invention can be made using known solution polymerization techniques, wherein the reactant monomers and initiator are dissolved in an appropriate solvent such as toluene, xylene, tetrahydrofuran, or mixtures thereof. Polymerization can be accomplished in the time and at the temperature necessary, e.g., 60° C. to 80° C. and about 2 to 24 hours. The polymer product can be isolated through normal separation techniques, including solvent stripping.

In one embodiment, these polymers for use in the present invention exhibit a weight average molecular weight, as determined by gel permeation chromatography and light scattering of a solution of the polymer in tetrahydrofuran and compared to a polystyrene standard, of greater than or equal to 30,000 grams per mole ("g/mole"). In one embodiment, the polymer of the present invention exhibits a weight average molecular weight of from 30,000 to 10,000,000 g/mole, more typically to about 500,000 g/mole, and even more typically from about 150,000 g/mole to about 1,500,000 g/mole, for example about 1,000,000 g/mol or about 800,000 g/mole.

In one embodiment, these polymers for use in the present invention are in the form of an aqueous colloidal polymer dispersion. When the polymer composition is in the form of an aqueous colloidal polymer dispersion, the composition is maintained at a pH of about 5 or less to maintain stability. More typically, the aqueous colloidal polymer dispersion composition has a pH of about 2 to about 3. When thickening of the composition is desired, the pH of the composition can be increased to a value above about 5 by addition of a base to solubilize the polymer.

These polyanionic HASE polymer-containing compositions for use in the present invention are pH-responsive. At the lower pH levels at which the emulsion polymerization takes place, i.e., pH levels of 5 or less, the composition is relatively thin or non-viscous. When the pH of the polymer dispersion is neutralized or adjusted by addition of a base to a pH of about 5.5 or more, preferably about 6 to about 11, the composition thickens substantially. The composition turns from semi-opaque or opaque to translucent or transparent as viscosity increases. Viscosity increases as polymer dissolves partially or completely in the aqueous phase of the composition. Neutralization can occur in situ when the emulsion polymer is blended with the base and added to the aqueous phase. Or, if desired for a given application, neutralization can be carried out when blending with an aqueous product. Useful bases include, but are not limited to, ammonia, an amine, sodium hydroxide, potassium carbonate or the like.

For example, the polyanionic HASE polymer having a polymer backbone of MAA and EA is pH-sensitive. Typically the copolymer is a latex at pH=2.3. When neutralized with a suitable base to a pH above about 5.5, the carboxyl groups on the methacrylic acid ionize to carboxylate ions. The charge on the polymer induces a conformational change, and the white latex becomes water-soluble, thus increasing the hydrodynamic volume of the polymer. When the HASE polymers swell, the pendant hydrophobic groups are free to build associations with one another and with other hydrophobes available in the formulation, such as surfactants, particulates, emulsion droplets and dyes. This phenomenon creates a network structure that results in a significant viscosity build.

HASE Polymer Blends

In a second aspect, the present invention is directed to a blend of a first anionic polymer comprising one or more first monomeric units, each independently comprising at least one bicycloheptyl-polyether, bicycloheptenyl-polyether or branched ($C_5$-$C_{50}$)alkyl-polyether group per monomeric unit, wherein the bicycloheptyl-polyether or bicycloheptenyl-polyether group may optionally be substituted on one or more ring carbon atoms by one or two ($C_1$-$C_6$)alkyl groups per carbon atom, having a weight average molecular weight of greater than or equal to about 30,000 grams per mole, and a second anionic polymer comprising one or more second monomeric units, each independently comprising at least one pendant linear or branched ($C_5$-$C_{50}$)alkyl-polyether group per monomeric unit, provided that the first and second monomeric units cannot both comprise a branched ($C_5$-$C_{50}$)alkyl-polyether group, having a weight average molecular weight of greater than or equal to about 30,000 grams per mole, wherein the first and second polymers each further comprise at least one polymerizable acid functional group per molecule of polymer, and the first and second monomeric units cannot both comprise a branched $(C_5-C_{50})$alkyl-polyether group.

The first monomeric units and second monomeric units for the blend of polymers may be further defined as described above for the copolymer containing both the first monomeric units and second monomeric units. Furthermore, the first polymer may contain the above-described first monomeric units, third monomeric units and fourth monomeric units. The second polymer may contain the above-described second monomeric units, third monomeric units and fourth monomeric units.

For example, a blend could include a first anionic polymer and a second anionic polymer.

The first anionic polymer comprises, based on 100 pbw of the polymer, from about 0.1, more typically from about 0.5, and even more typically from about 1.0 pbw of the first monomeric units, to about 20, more typically to about 15, and even more typically to about 10, pbw of the first monomeric units, from about 20, more typically from about 25, and even more typically from about 30, pbw of the third monomeric units, to about 60, more typically to about 55, and even more typically to about 60, pbw of the third monomeric units, and from about 25, more typically from about 35, and even more typically from about 40, pbw of the fourth monomeric units, to about 70, more typically to about 65, and even more typically to about 60, pbw of the fourth monomeric units.

The second anionic polymer comprises, based on 100 pbw of the polymer, optionally from about 0.1, more typically from about 0.5, and even more typically from about 1.0 pbw of the first monomeric units, to about 20, more typically to about 15, and even more typically to about 10, pbw of the first monomeric units, from about 0.1, more typically from about 0.5, and even more typically from about 1.0, pbw of the second monomeric units, to about 20, more typically to about 15, and even more typically to about 10, pbw of the second monomeric units, and from about 20, more typically from about 25, and even more typically from about 30, pbw of the third monomeric units including acid functional groups, to about 60, more typically to about 55, and even more typically to about 60, pbw of the third monomeric units, and from about 25, more typically from about 35, and even more typically from about 40, pbw of the fourth monomeric units, to about 70, more typically to about 65, and even more typically to about 60, pbw of the fourth monomeric units.

Liquid Carrier

In one embodiment, the composition of the present invention comprises the selected cationic polymer, the anionic polymer, for example a HASE polymer, and a liquid carrier.

In one embodiment, the liquid carrier is an aqueous carrier comprising water and the treatment solution is in the form of a solution, emulsion, or dispersion of the material and additives. In one embodiment, the liquid carrier comprises water and a water miscible organic liquid. Suitable water miscible organic liquids include saturated or unsaturated monohydric alcohols and polyhydric alcohols, such as, for example, methanol, ethanol, isopropanol, cetyl alcohol, benzyl alcohol, oleyl alcohol, 2-butoxyethanol, and ethylene glycol, as well as alkylether diols, such as, for example, ethylene glycol monoethyl ether, propylene glycol monoethyl ether and diethylene glycol monomethyl ether.

As used herein, terms "aqueous medium" and "aqueous media" are used herein to refer to any liquid medium of which water is a major component. Thus, the term includes water per se as well as aqueous solutions and dispersions.

Compositions

Preferred combinations of anionic polymer and cationic polymer are as listed in TABLE 2A and typical Anionic Charge Densities of the anionic polymers are listed in TABLE 2B. Typical Cationic Charge Densities of the cationic polymers are listed in TABLE 3. The HASE polymer labels correspond to those they are given in the Examples of this specification

TABLE 2A

| Polyanionic | Polycationic |
|---|---|
| HASE polymer G | JAGUAR C-1000 (Cationic guar) |
|  | POLYCARE 400 (PQ 10) |
|  | CELQUAT H-100 (PQ-4) |
|  | DV7578 (depoplymerized cationic guar) |
|  | JAGUAR C-1000 + sodium thiosulfate |
| HASE polymer I | JAGUAR C-1000 (Cationic guar) |
| HASE polymer J | JAGUAR C-1000 (Cationic guar) |
| HASE polymer K | JAGUAR C-1000 (Cationic guar) |
| CARBOPOL AQUA SF-1 | JAGUAR C-1000 (Cationic guar) |
| Polyacrylamide | JAGUAR C-1000 (Cationic guar) |
| Polyacrylic acid | JAGUAR C-1000 (Cationic guar) |
| Hydrolyzed polyacrylamide |  |
| RHODIA copolymer AM/AA/AMPS | Copolymer of acrylamide, acrylic acid and acrylamidomethylpropane sulfonic) |

TABLE 2B

| Polyanionic | backbone | anionic/ anionizable grafts | Mol. Wt. (anionic monomeric unit 1) g/mole | number of charges per anionic monomer unit | [monomeric unit 1] wt % | charge density (millieq per gram) |
|---|---|---|---|---|---|---|
| HASE polymer A | synthetic | methacrylic acid units | 86 | 1 | 15.8 | 1.84 |
| HASE polymer B | synthetic | methacrylic acid units | 86 | 1 | 15.8 | 1.84 |
| HASE polymer C | synthetic | methacrylic acid units | 86 | 1 | 15.8 | 1.84 |
| HASE polymer D | synthetic | methacrylic acid units | 86 | 1 | 15.8 | 1.84 |
| LUBRIZOL CARBOPOL AQUA SF1 | synthetic | acrylic acid units | 72 | 1 | 15.8*** | 2.19 |
| Polyacrylamide | synthetic | acrylic acid units | 72 | 1 | 71 | 9.86 |

TABLE 2B-continued

| Polyanionic | backbone | anionic/anionizable grafts | Mol. Wt. (anionic monomeric unit 1) g/mole | number of charges per anionic monomer unit | [monomeric unit 1] wt % | charge density (millieq per gram) |
|---|---|---|---|---|---|---|
| Polyacrylic acid | synthetic | acrylic acid units | 72 | 1 | 71 | 9.86 |
| Hydrolyzed polyacrylamide | synthetic | acrylic acid units | 72 | 1 | 10 | 1.39 |
| RHODIA copolymer AM/AA/AMPS | synthetic | acrylic acid units + sulfonates | 110* | 1 | 46 | 2.36** |

*copolymer AM/AA/AMPS thickener is a mixture of Acrylic Acid (AA), 2-acrylamido-2-methylpropane sulfonate (AMPS) and Acrylamide (Am) having a MWavg of 3-6 million.
**copolymer AM/AA/AMPS thickener has a charge density of 2.36 millieq/g when none of the acrylamide units are hydrolyzed and 9.97 millieq/g if all the Am units are hydrolyzed during the use (high T, basic pH).
***estimate

TABLE 3

| cationic | backbone | cationic/cationizable grafts | CCD (millieq/g) | Mw (g/mole) |
|---|---|---|---|---|
| PQ 10 (POLYCARE 400) | hydroxyethyl cellulose | hydroxypropyl trimethylammonium chloride | 1.21-1.57 | 0.4-0.8 million |
| JAGUAR C17 | guar | hydroxypropyl trimethylammonium chloride | 0.91-1.04 | 2.5-3.0 million |
| PQ4 (CELQUAT H100) | hydroxyethyl cellulose | homopoly(diallyl dimethyl ammonium chloride) | 0.71 | 1.4 million |
| JAGUAR C13 JAGUAR C14 | guar | hydroxypropyl trimethylammonium chloride | 0.56-0.72 | 2.5-3.0 million |
| JAGUAR EXCEL | guar | hydroxypropyl trimethylammonium chloride | 0.56-0.72 | 1.5-2.0 million |
| JAGUAR C500 | guar | hydroxypropyl trimethylammonium chloride | 0.56-0.72 | 0.35-0.65 million |
| JAGUAR C1000 | guar | hydroxypropyl trimethylammonium chloride | 0.51-0.56 | 0.5-1.0 million |
| JAGUAR C162 | hydroxypropyl guar | hydroxypropyl trimethylammonium chloride | 0.47-0.60 | 1.5-2.0 million |

The cationic natural polymers used were the following: JAGUAR C-1000 guar gum (cationic guar hydroxypropyl trimonium chloride), and POLYCARE 400 (PQ-10). The term PQ-10 means polyquaternium-10 polymers which are quaternized hydroxyethylcellulose.

CARBOPOL AQUA SF-1 polymer is an Alkali-Swellable acrylic Emulsion (ASE) polymer. As supplied, the majority of the polymer's carboxyl functionality is in the protonated form; the polymer molecules are coiled and bring relatively little suspension and viscosity to the liquid. Upon neutralization, the molecules ionize and expand due to the charge repulsion of the anionic carboxylate. Thus they provide suspending and thickening properties to the aqueous system in which they reside. This mechanism is known as "hydrodynamic thickening". In this theory, it is the physical packing of polymer molecules that is responsible for the development of suspending ability and viscosity. Thus this "space-filling" mechanism is distinctly different from the associative thickening mechanism attributed to HASE polymers.

Typical anionic polymers range in wt. average molecular weight from 30,000 to 5,000,000, typically 45,000 to 800,000 or 1,000,000 to 2,000,000 g/mol.

The polymer of the present invention is particularly useful as a thickener for a wide variety of water-based compositions. Such compositions include brine, slurries, and colloidal dispersions of water-insoluble inorganic and organic materials, such as natural rubber, synthetic or artificial latexes. The emulsion polymers of the invention are especially useful in areas requiring thickening at neutral pHs, such as in personal care compositions or consumer care compositions, for example, sanitizers or detergents, or industrial cleaners.

The polymers of the invention are also especially useful in areas requiring thickening at neutral pHs, such as in oilfield fracturing compositions comprising, for example, proppant; or for injecting gravel packing, or surfactant flooding for enhanced oil recovery; or acidizing with acid, such as HCl.

In one embodiment, the aqueous composition of the present invention exhibits viscoelastic properties at neutral to alkaline pH values, typically at pH values greater than or equal to about 5, more typically greater than or equal to about 5.5, even more typically of from about 6 to about 9.

In one embodiment, an aqueous composition of the present invention exhibits non-Newtonian "shear thinning" viscosity, that is, a viscosity that, within a given range of shear stress, decreases with increasing shear stress.

Yield Strength

In one embodiment, an aqueous composition of the present invention exhibits "yield strength", that is, a minimum shear stress required to initiate flow of the composition, and exhibits shear thinning behavior over some range of shear stress above the yield strength. In one embodiment, the composition of the present invention containing a cationic polymer and anionic polymer is not crosslinked and provides yield strength of greater than 0 Pa, even in the absence of any cross-linking of the polymers of the composition. Thus, in one embodiment of the composition, the composition of the present invention imparts a yield strength to the composition that is greater than 0 Pa, more typically of from about 0.01 Pa, and even more typically from about 0.1 to about 10 Pa, and even more typically about 6 or 4 Pa, and even more typically about 2 Pa. A non-zero yield strength is useful for suspending water insoluble particles in the composition.

In one embodiment of the composition wherein the composition has a pH of greater than or equal to 6.5, the polymer of the present invention provides thickening properties and imparts a non-zero yield strength in the presence of surfactant without imparting an optically turbid appearance to the composition, thus allowing formulation of optically clear compositions having a non-zero yield strength.

In one embodiment of the composition, typically wherein the composition has a pH of greater than or equal to about 6.5, the polymer of the present invention provides thickening properties and imparts a non-zero yield strength in the presence of surfactants and/or non-surfactant salts and the composition clear, transparent visual appearance, for example, a transmittance at 600 nm of greater than 95%.

In one embodiment of the composition, typically wherein the composition has a pH of less than about 6.5, the polymer of the present invention provides thickening properties and imparts a non-zero yield strength in the presence of surfactants and/or non-surfactant salts, and imparts an opaque visual appearance to the composition. Also, a higher yield strength can typically be obtained with given polymer content at a pH of less than 6, compared to a composition having a pH of greater than or equal to 6.5.

Embodiments of Compositions Employing the Composition of the Present Invention

The polymer compositions of the present invention may be added to aqueous product systems at a wide range of amounts depending on the desired system properties and end use applications. The polymer may typically be added at any stage or at multiple stages of the preparation of an aqueous product composition, such as, by addition to water before addition of other ingredients, by addition to the composition among other added ingredients, or by addition after addition of any other ingredients, as the final ingredient in a series of additions and/or as a post-addition to the composition, such as, for example, as a post-addition to adjust the rheological properties of the composition.

In one embodiment of the composition the polymer of the present invention provides high foam volume. In an embodiment of the composition that comprises a cationic polymer, the polymer of the present invention provides high foam volume and reduces drainage, resulting in a wet, creamy, shiny, white foam.

In embodiments employing HASE polymers, the composition forming the subject matter of the invention can comprise, depending on its application, from 0.001 to 10% of its weight of at least one of the selected HASE polymers.

The pH of the composition or the pH of use of the composition according to the invention can vary, depending on the application. The pH of the compositions can be in the range of from about 2 to about 12, preferably from about 4 to about 10 and most preferably from about 5 to about 8. Typically the pH is greater than or equal to 7. The pH can be adjusted using a buffer such as, but not limited to, citric acid.

In embodiments employing HASE polymers, the composition can be employed in an amount such that, after optional rinsing and after drying, the amount of the one or more selected HASE polymers deposited on the surface is typically from 0.0001 to 10 mg/m$^2$, for example, 0.001 to 5 mg/m$^2$, of surface treated.

Surfactants

Some fluids according to the invention may also include a surfactant.

The polymer of the present invention of the present invention is suitable in the preparation of hydraulic fracturing fluids, enhanced oil recovery compositions, latex paints, personal care products (cosmetics, toiletries, health and beauty aids, cosmeceuticals) and topical health care products to which an effective amount of the associative polymer can be incorporated for achieving a beneficial or desirable, physical or chemical, effect therein during storage and/or usage. For example, personal or topical care products could be any of, without limitation, hair care products, such as shampoos (including combination shampoos, such as "two-in-one" conditioning shampoos), post-shampoo rinses, setting and style maintenance agents including setting aids, such as gels and sprays, grooming aids, such as pomades, conditioners, perms, relaxers, hair smoothing products, and the like. For example, personal or topical care products could be any of, without limitation, skin care products (facial, body, hands, scalp and feet), such as creams, lotions, conditioners, and cleansing products, anti-acne products, anti-aging products (exfoliant, keratolytic, anticellulite, antiwrinkle, and the like), skin protectants such as sunscreens, sunblock, barrier creams, oils, silicones, and the like. For example, personal or topical care products could be any of, without limitation, skin color products (whiteners, lighteners, sunless tanning accelerators, and the like), hair colorants (hair dyes, hair color rinses, highlighters, bleaches and the like), pigmented skin colorants (face and body makeups, foundation creams, mascara, rouge, lip products, and the like), bath and shower products (body cleansers, body wash, shower gel, liquid soap, soap bars, syndet bars, conditioning liquid bath oil, bubble bath, bath powders, and the like), nail care products (polishes, polish removers, strengtheners, lengtheners, hardeners, cuticle removers, softeners, and the like), and any aqueous acidic to basic composition.

In one embodiment, the present invention is directed to a personal care composition comprising water, one or more surfactants, and a polymer of the present invention.

In one embodiment, the personal care composition comprises, based on 100 parts by weight ("pbw") of the personal care composition, from about 10 to about 80 pbw, more typically from about 20 to about 70 pbw, water, from about 1 to about 50 pbw of one or more surfactants, and from about 0.05 to about 10 pbw, more typically from about 0.1 to about 5 pbw, of the polymer of the present invention.

Suitable surfactants for including in compositions of the present invention include anionic surfactants, cationic surfactants, amphoteric surfactants, zwitterionic surfactants, nonionic surfactants, and mixtures thereof.

Typically the surfactant acts as a surface active agent and may function as an emulsifier, dispersant, oil-wetter, water-wetter, foamer and defoamer. For example, when the surfactant is used as a foamer, any surfactant for which its ability to aid the dispersion and/or stabilization of any gas component incorporated with the base fluid to form a foamed or energized fluid may be used. Viscoelastic surfactants, such as those described in U.S. Pat. No. 6,703,352 (Dahayanake, et al.) and U.S. Pat. No. 6,482,866 (Dahayanake, et al.), both incorporated herein by reference, may also be suitable for use in fluids of the invention, provided that substantial micelle formation is avoided that may impact the overall characteristics of the gelled fluid.

Anionic Surfactant

In some embodiments of the invention, the surfactant is an ionic surfactant. Examples of suitable ionic surfactants include, but are not limited to, anionic surfactants such as alkyl carboxylates, alkyl ether carboxylates, alkyl sulfates, alkyl ether sulfates, alkyl sulfonates, alpha-olefin sulfonates, alkyl phosphates and alkyl ether phosphates.

Anionic surfactants are generally known. Suitable anionic surfactants include, for example, alkylbenzene sulfonates, alpha olefin sulfonates, paraffin sulfonates, alkyl ester sulfonates, alkyl sulfates, alkyl alkoxy sulfates, alkyl sulfonates, alkyl alkoxy carboxylates, alkyl alkoxylated sulfates, monoalkyl phosphates, and dialkyl phosphates, alkyl lactylates, isethionate taurate surfactants, sarcosinate surfactants and salts thereof, as well as mixtures of such compounds, wherein the cationic counterion of an anionic surfactant in salt form is typically selected from sodium, potassium, lithium, calcium, magnesium, ammonium, $(C_1-C_6)$alkyl ammonium cations.

Anionic surfactants also include, for example, alkylbenzene sulfonates, alpha olefin sulfonates, paraffin sulfonates, alkyl ester sulfonates, alkyl sulfates, alkyl alkoxy sulfates, alkyl sulfonates, alkyl alkoxy carboxylates, alkyl alkoxylated sulfates, monoalkyl phosphates, and dialkyl phosphates, alkyl lactylates, isethionate taurate surfactants sarcosinate surfactants and salts thereof, as well as mixtures of such compounds, wherein the cationic counterion of an anionic surfactant in salt form is typically selected from sodium, potassium, lithium, calcium, magnesium, ammonium, $(C_1-C_6)$alkyl ammonium cations.

Specific examples of suitable anionic surfactant include ammonium lauryl sulfate, ammonium laureth sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium trideceth sulfate, sodium tridecyl sulfate, ammonium trideceth sulfate, ammonium tridecyl sulfate, disodium laureth sulfosuccinate, sodium monoalkyl phosphate, sodium dialkyl phosphate, ammonium cocoyl sulfate, sodium cocoyl sulfate, potassium cocoyl sulfate, monoethanolamine cocoyl sulfate, sodium tridecyl benzene sulfonate, and sodium dodecyl benzene sulfonate, sodium lauroyl isethionate, potassium methyl myristyl taurate, ammonium oleoyl sarconsinate and mixture thereof.

Suitable anionic surfactants include, for example, one or more branched and/or linear organosulfate surfactants. In one embodiment, the anionic surfactant comprises one or more anionic organosulfate surfactants according to structure (1):

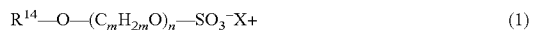

wherein $R^{14}$ is $(C_8-C_{18})$alkyl or $(C_8-C_{18})$alkenyl, more typically $(C_{10}-C14)$alkyl, m is 2, 3, or 4, n is an integer of from 1 to about 7, more typically from 1 to 8, even more typically from 1 to 6, $X^+$ is a cation.

In one embodiment, $R^{14}$ is a branched $(C_8-C_{18})$alkyl group or a $(C_8-C_{18})$alkenyl group, more typically a branched $(C_{10}-C_{16})$alkyl group, such as tridecyl. Suitable branched alkyl groups include methyldecyl groups, methylundecyl groups, methyldodecyl groups, ethyldecyl groups, ethylundecyl groups, and ethyldodecyl groups, such as for example, 1-methyldecyl, 1-methylundecyl, 1-methyldodecyl, 1-ethyldecyl, 1-ethylundecyl, and 1-ethyldodecyl.

In one embodiment, m is 2 or 3, more typically 2.

In one embodiment, n is 1, 2, 3, or 4. As used herein, modifying an alkyl or alkenyl group with the suffix "eth" generally indicates the addition of one or more ethylene oxide units, for example, trideceth refers to an ethoxylated tridecyl group, and the suffix "-n", wherein n is an integer, indicates the number of such ethylene oxide units per group, for example "trideceth-3" indicates an ethoxylated tridecyl group with 3 ethylene oxide units per tridecyl group.

Typical branched anionic surfactants include, for example, sodium trideceth sulfate, sodium tridecyl sulfate, ammonium trideceth sulfate, and ammonium tridecyl sulfate, magnesium trideceth sulfates, monoethanolamine trideceth sulfate, diethanolamine trideceth sulfates, and triethanolamine trideceth sulfate.

In one embodiment, the anionic organosulfate surfactant comprises one or more branched alkylether sulfate selected from sodium trideceth-1 sulfate, potassium trideceth-1 sulfate, and ammonium trideceth-1 sulfate, sodium trideceth-2 sulfate, potassium trideceth-2 sulfate, and ammonium trideceth-2 sulfate, sodium trideceth-3 sulfate, potassium trideceth-3 sulfate, and ammonium trideceth-3 sulfate, sodium trideceth-4 sulfate, potassium trideceth-4 sulfate, and ammonium trideceth-4 sulfate.

Typical linear anionic surfactants include, for example, one or more linear C10-C22 alkyl, ammonium or alkali metal ether sulfates, for example, ammonium lauryl sulfate, ammonium laureth sulfate, triethanolamine laureth sulfate, monoethanolamine lauryl sulfate, monoethanolamine laureth sulfate, diethanolamine lauryl sulfate, diethanolamine laureth sulfate, magnesium laureth sulfate, lauric monoglyceride sodium sulfate, sodium lauryl sulfate, sodium laureth sulfate, potassium lauryl sulfate, and potassium laureth sulfate.

In one embodiment, the anionic surfactant comprises disodium laureth sulfosuccinate, sodium monoalkyl phosphate, sodium dialkyl phosphate, ammonium cocoyl sulfate, sodium cocoyl sulfate, potassium cocoyl sulfate, monoethanolamine cocoyl sulfate, sodium tridecyl benzene sulfonate, and sodium dodecyl benzene sulfonate, sodium oleth sulfate, potassium oleth sulfate, magnesium oleth sulfate, ammonium oleth sulfate, monoethanolamine oleth sulfate, diethanolamine oleth sulfate, triethanolamine oleth sulfate, or a mixture thereof.

In one embodiment, the anionic surfactant comprises one or more anionic surfactant selected from isethionate surfactant compounds, taurate surfactant compounds, and sarcosinate surfactant compounds, according to structure (2):

wherein:

$R^1$ is alkyl, alkenyl, aryl, or aralkyl, $R^2$ is alkylene, which may optionally be substituted on one or more of such methylene units with alkyl, alkoxyl, alkenyl, aryl, aralkyl, alkaryl, or heterocyclyl, and which may optionally be interrupted at one or more positions by an oxygen atom, X is O or $NR^3$, NR³ is H or alkyl,
Y⁻ is $SO_3^-$ or $CO_2^-$, and
M⁺ is a cation.

In one embodiment, R² is methylene, or dimethylene.

In one embodiment, R² is alkyleneoxyalkylene or alkylene poly(oxyalkylene) comprising from 2 to about 50 oxyalkylene units, more typically methylenepoly(oxyethylene), dimethylenepoly(oxyethylene), methylenepoly(oxypropylene), or dimethylenepoly(oxypropylene).

In one embodiment, M⁺ is sodium, potassium, lithium, calcium, magnesium, ammonium cation, or an ammonium cation, such as, for example, an isopropylammonium, monoethanolammonium, diethanolammonium, or triethanolammonium cation. More typically, M+ is a sodium cation.

Suitable isethionate surfactants are esters of isethionic acid and salts thereof. In one embodiment, the second anionic surfactant comprises one or more isethionate surfactant compounds according to structure (2):

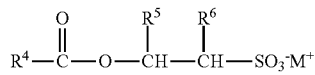

(3)

wherein:
R⁴ is alkyl, alkenyl, aryl, or aralkyl,
R⁵ and R⁶ are each independently H or alkyl, and
M⁺ is a cation.

In one embodiment, the anionic surfactant comprises one or more N-acyl isethionate surfactant compounds according to structure (3), wherein R⁴ is $(C_8-C_{22})$alkyl and R⁵ and R⁶ are each independently H or $(C_1-C_4)$alkyl, more typically H or methyl.

In one embodiment, the anionic surfactant comprises one or more N-acyl isethionate surfactant compounds according to structure (3), wherein R⁴ is $(C_8-C_{22})$alkyl and R⁵ and R⁶ are each independently H or $(C_1-C_4)$alkyl, more typically H or methyl, and M+ is a sodium, potassium, or ammonium cation.

Suitable isethionate surfactant compounds according to structure (3) include, for example, sodium lauroyl isethionate, sodium lauroyl isethionate, sodium myristoyl isethionate, sodium cocoyl isethionate, sodium oleoyl isethionate, and ammonium oleoyl isethionate.

Suitable taurate surfactants are amides of methyl taurine and salts thereof. In one embodiment, the second anionic surfactant comprises one or more taurate surfactant compounds according to structure (4):

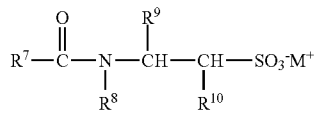

(4)

wherein:
R⁷ is alkyl, alkenyl, aryl, or aralkyl
R⁸ is H or alkyl,
R⁹ and R¹⁹ are each independently H or alkyl, and
M⁺ is a cation.

In one embodiment, the second anionic surfactant comprises one or more N-acyl taurate surfactant compounds according to structure (3), wherein R⁷ is $(C_8-C_{22})$alkyl, R⁸ is H or $(C_1-C_4)$alkyl, more typically H or methyl, and R⁹ and R¹⁰ are each independently H or $(C_1-C_4)$alkyl, more typically H or methyl.

In one embodiment, the second anionic surfactant comprises one or more N-acyl taurate surfactant compounds according to structure (4), wherein R⁷ is $(C_8-C_{22})$alkyl, R⁸ is H or $(C_1-C_4)$alkyl, more typically H or methyl, and R⁹ and R¹⁰ are each independently H or $(C_1-C_4)$alkyl, more typically H or methyl, and M+ is a sodium, potassium, or ammonium cation.

Suitable taurate surfactant compounds according to structure (4) include, for example, sodium methyl lauroyl taurate, sodium methyl myristoyl taurate, potassium methyl myristoyl taurate, sodium methyl cocoyl taurate, sodium methyl oleoyl taurate, calcium methyl lauroyl taurate, potassium methyl lauroyl taurate, and ammonium methyl lauroyl taurate.

Suitable sarcosinate surfactants are amides of sarcosine and salts thereof. In one embodiment, the first anionic surfactant comprises one or more sarcosinate surfactant compounds according to structure (5):

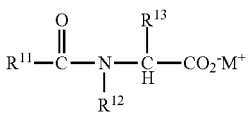

(5)

wherein:
R¹¹ is alkyl, alkenyl, aryl, or aralkyl, and
R¹² is H or alkyl,
R¹³ is H, alkyl, and
M⁺ is a cation.

In one embodiment, the anionic surfactant comprises one or more sarcosinate surfactant compounds according to structure (5), wherein R¹¹ is $(C_8-C_{22})$alkyl, and R¹² and R¹³ are each independently H or $(C_1-C_4)$alkyl, more typically H or methyl.

In one embodiment, the anionic surfactant comprises one or more sarcosinate surfactant compounds according to structure (5), wherein R¹¹ is $(C_8-C_{22})$alkyl, R¹² and R¹³ are each independently H or $(C_1-C_4)$alkyl, more typically H or methyl, and M+ is a sodium, potassium or ammonium cation.

Suitable sarcosinate surfactant compounds according to structure (5) include, for example, sodium lauroyl sarconsinate, sodium myristoyl sarconsinate, potassium myristoyl sarconsinate, sodium cocoyl sarconsinate, sodium oleoyl sarconsinate, triethanolamine lauroyl sarconsinate, and ammonium oleoyl sarconsinate.

The cationic counterion of any anionic surfactant in salt form is typically a sodium cation but may alternatively be a potassium, lithium, calcium, magnesium, ammonium cation, or an alkyl ammonium anion having up to 6 aliphatic carbon atoms, such as anisopropylammonium, monoethanolammonium, diethanolammonium, or triethanolammonium cation. Ammonium and ethanolammonium salts are generally more soluble than the sodium salts. Mixtures of the above cations are suitable as well.

Cationic Surfactants

Examples of suitable ionic surfactants also include, but are not limited to, cationic surfactants such as alkyl amines, alkyl diamines, alkyl ether amines, alkyl quaternary ammonium, dialkyl quaternary ammonium and ester quaternary ammonium compounds.

Cationic surfactants are generally known and include for example, mono-cationic surfactants according to formula (A.XXV):

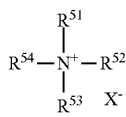

(A.XXV)

wherein:

$R^{51}$, $R^{52}$, $R^{53}$, and $R^{54}$ are each independently H or an organic group, provided that at least one of $R^{51}$, $R^{52}$, $R^{53}$, and $R^{54}$ is not hydrogen, and $X^-$ is an anion, more, chloride, bromide, methosulfate, ethosulfate, lactate, saccharinate, acetate or phosphate anion.

If one to three of $R^{51}$, $R^{52}$, $R^{53}$, and $R^{54}$ of the compound of structure XXV are each H, then the compound according to structure A.XXV is an amine salt. Suitable amine slat type cationic surfactants include polyethoxylated (2) oleyl/stearyl amine, ethoxylated tallow amine, cocoalkylamine, oleylamine, and tallow alkyl amine.

If $R^{51}$, $R^{52}$, $R^{53}$, and $R^{54}$ of the compound of structure A.XXV are each independently an organic group, then the compound of structure A.XXV is a quaternary ammonium compound. In one embodiment, $R^{51}$, $R^{52}$, $R^{53}$, and $R^{54}$ are each independent ($C_8$-$C_{24}$) branched or linear hydrocarbon groups which may comprise additional functionality such as, for example, fatty acids or derivatives thereof, including esters of fatty acids and fatty acids with alkoxylated groups, alkyl amido groups, aromatic rings, heterocyclic rings, phosphate groups, epoxy groups, and hydroxyl groups. The nitrogen atom may also be part of a heterocyclic or aromatic ring system, e.g., cataphyll morpholinium ethosulfate or steapyrium chloride.

Examples of suitable quaternary ammonium compounds of the monoalkyl amine derivative type include: cetyl trimethyl ammonium bromide (also known as CETAB or cetrimonium bromide), cetyl trimethyl ammonium chloride (also known as cetrimonium chloride), myristyl trimethyl ammonium bromide (also known as myrtrimonium bromide or Quaternium-13), stearyl dimethyl benzyl ammonium chloride (also known as stearalkonium chloride), oleyl dimethyl benzyl ammonium chloride, (also known as olealkonium chloride), lauryl/myristryl trimethyl ammonium methosulfate (also known as cocotrimonium methosulfate), cetyl dimethyl (2)hydroxyethyl ammonium dihydrogen phosphate (also known as hydroxyethyl cetyldimonium phosphate), cocotrimonium chloride, distearyldimonium chloride, wheat germ-amidopropalkonium chloride, stearyl octyldimonium methosulfate, isostearaminopropalkonium chloride, dihydroxypropyl PEG-5 linoleaminium chloride, PEG-2 stearmonium chloride, Quaternium 18, Quaternium 80, Quaternium 82, Quaternium 84, behentrimonium chloride, dicetyl dimonium chloride, behentrimonium methosulfate, tallow trimonium chloride and behenamidopropyl ethyl dimonium ethosulfate. Mixtures may also be used in the present invention.

Quaternary ammonium compounds of the dialkyl amine derivative type include, for example, distearyldimonium chloride, dicetyl dimonium chloride, stearyl octyldimonium methosulfate, dihydrogenated palmoylethyl hydroxyethylmonium methosulfate, dipalmitoylethyl hydroxyethylmonium methosulfate, dioleoylethyl hydroxyethylmonium methosulfate, hydroxypropyl bissstearyldimonium chloride, and mixtures thereof.

Quaternary ammonium compounds of the imidazoline derivative type include, for example, isostearyl benzylimidonium chloride, cocoyl benzyl hydroxyethyl imidazolinium chloride, cocoyl hydroxyethylimidazolinium PG-chloride phosphate, Quaternium 32, and stearyl hydroxyethylimidonium chloride, and mixtures thereof.

Typical cationic surfactants comprise dialkyl derivatives such as dicetyl dimonium chloride and distearyldimonium chloride, branched and/or unsaturated cationic surfactants such as isostearylaminopropalkonium chloride or olealkonium chloride, long chain cationic surfactants such as stearalkonium chloride and behentrimonium chloride, as well as mixtures thereof.

Suitable anionic counterions for the cationic surfactant include, for example, chloride, bromide, methosulfate, ethosulfate, lactate, saccharinate, acetate and phosphate anions.

Amphoteric Surfactants and Zwitterionic Surfactants

Examples of suitable ionic surfactants also include, but are not limited to, surfactants that are usually regarded as zwitterionic surfactants and in some cases as amphoteric surfactants such as alkyl betaines, alkyl amido betaines, alkyl imidazolines, alkyl amine oxides and alkyl quaternary ammonium carboxylates. The amphoteric surfactant is a class of surfactant that has both a positively charged moiety and a negatively charged moiety over a certain pH range (e.g. typically slightly acidic), only a negatively charged moiety over a certain pH range (e.g. typically slightly alkaline) and only a positively charged moiety at a different pH range (e.g. typically moderately acidic), while a zwitterionic surfactant has a permanent, positively charged moiety in the molecule regardless of pH and a negatively charged moiety at alkaline pH.

Amphoteric Surfactant

Amphoteric surfactants are generally known. Suitable amphoteric surfactants include the alkali metal, alkaline earth metal, ammonium or substituted ammonium salts of alkyl amphodipropionates, alkyl amphodiacetates, alkyl amphoglycinates, and alkyl amphopropionates, as well as alkyl iminopropionates, alkyl iminodipropionates, and alkyl amphopropylsulfonates. Typical amphoteric surfactants are fatty acid amides.

Other examples of such amphoteric surfactants include for example, cocoamphoacetate cocoamphopropionate, cocoamphodiacetate, lauroamphoacetate, lauroamphodiacetate, lauroamphodipropionate, lauroamphodiacetate, cocoamphopropylsulfonate, caproamphodiacetate, caproamphoacetate, caproamphodipropionate, and stearoamphoacetate. Specific examples of suitable amphoteric surfactant include sodium lauroamphoacetate, sodium lauroamphopropionate, disodium lauroamphodiacetate, sodium cocoamphoacetate, disodium cocoamphodiacetate, or a mixture thereof.

Typical suitable amphoteric surfactants include the alkali metal, alkaline earth metal, ammonium or substituted ammonium salts of alkyl amphodipropionates, alkyl amphodiacetates, alkyl amphoglycinates and alkyl amphopropionates, alkyl amphocarboxy glycinates and alkyl amphocarboxypropionates, wherein alkyl represents an alkyl group having 6 to 20 carbon atoms. Other typical amphoteric surfactants include alkyl iminopropionates, alkyl iminodipropionates and alkyl amphopropylsulfonates having between 12 and 18 carbon atoms; alkyl betaines and amidopropyl betaines and alkyl sultaines and alkylamidopropylhydroxy sultaines wherein alkyl represents an alkyl group having 6 to 20 carbon atoms.

The term "amphoteric surfactant" as utilized herein encompasses one or more amphoteric surfactants such as mixtures of amphoteric surfactants.

Particularly useful amphoteric surfactants include both mono and dicarboxylates such as those of the formulae 7 and 8:

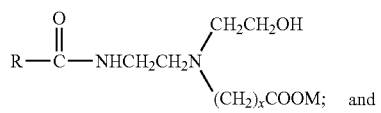

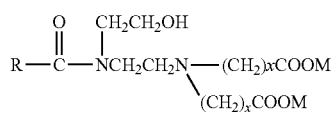

wherein R is an alkyl group of 6-20 carbon atoms, x is 1 or 2 and M is hydrogen or sodium. Mixtures of the above structures are particularly preferred.

A preferred amphoteric surfactant for use is cocoamphoacetate. It can be present from 0% to 10% based on the total weight of the concentrate. Preferably, cocoamphoacetate will comprise from about 1% to about 7% and most preferably from about 2% to about 4% of the concentrate.

In one embodiment, the amphoteric/zwitterionic surfactant comprises derivatives of aliphatic secondary and tertiary amines in which the aliphatic radical is straight chain or branched and wherein one of the aliphatic substituents contains from about 8 to about 18 carbon atoms and one contains an anionic water-solubilizing group, as well as mixtures thereof.

In one embodiment, the composition of the present invention is substantially free of amphoteric surfactants.

Zwitterionic Surfactant

Zwitterionic surfactants are generally known and include betaine surfactants and sultaine surfactants, such as for example decyl dimethyl betaine, undecyl dimethyl betaine, dodecyl dimethyl betaine, tridecyl dimethyl betaine, tetradecyl dimethyl betaine, coco dimethyl betaine, hexadecyl dimethyl betaine, heptadecyl dimethyl betaine, octadecyl dimethyl betaine, dodecylamidopropyl dimethyl betaine, cocoamidopropyl dimethyl betaine, oleylamidopropyl betaine, lauryl dihydroxypropyl glycinate, lauryl di(hydroxypoly(ethoxy)) glycinate, lauryl bis-(2-hydroxy-ethyl)carboxy methyl betaine, stearyl bis-(2-hydroxy-propyl)carboxymethyl betaine, cocodimethyl sulfopropyl betaine, stearyldimethyl sulfopropyl betaine, lauryl dimethyl sulfoethyl betaine, lauryl bis-(2-hydroxy-ethyl)sulfopropyl betaine, and mixtures thereof.

Suitable betaine surfactants also include cocodimethyl carboxymethyl betaine, lauryl dimethyl carboxymethyl betaine, lauryl dimethyl alpha-carboxyethyl betaine, cetyl dimethyl carboxymethyl betaine, oleyl dimethyl gamma-carboxypropyl betaine, and lauryl bis-(2-hydroxy-propyl)alpha-carboxyethyl betaine, amidopropyl betaines.

Suitable zwitterionic alkyl sultaine surfactants include alkylamidopropylhydroxy sultaines and fatty amine surfactants.

In one embodiment, the aqueous composition of the present invention is substantially free of zwitterionic surfactants.

Zwitterionic surfactants are generally known and include betaine surfactants and sultaine surfactants, such as for example decyl dimethyl betaine, undecyl dimethyl betaine, dodecyl dimethyl betaine, tridecyl dimethyl betaine, tetradecyl dimethyl betaine, coco dimethyl betaine, hexadecyl dimethyl betaine, heptadecyl dimethyl betaine, octadecyl dimethyl betaine, dodecylamidopropyl dimethyl betaine, cocoamidopropyl dimethyl betaine, oleylamidopropyl betaine, lauryl dihydroxypropyl glycinate, lauryl di(hydroxypoly(ethoxy)) glycinate, lauryl bis-(2-hydroxy-ethyl)carboxy methyl betaine, stearyl bis-(2-hydroxy-propyl)carboxymethyl betaine, cocodimethyl sulfopropyl betaine, stearyldimethyl sulfopropyl betaine, lauryl dimethyl sulfoethyl betaine, lauryl bis-(2-hydroxy-ethyl)sulfopropyl betaine, and mixtures thereof.

Amine Functional Surfactant

In some embodiments of the invention, the surfactant is a cationic, zwitterionic or amphoteric surfactant containing an amine group or a quaternary ammonium group in its chemical structure ("amine functional surfactant"). A particularly useful surfactant is the amphoteric alkyl amine contained in the surfactant solution AQUAT $94^4$® (available from Baker Petrolite of 12645 W. Airport Blvd, Sugar Land, Tex. 77478 USA).

Blends

In other embodiments of the invention, the surfactant is a blend of two or more of the surfactants described above, or a blend of any of the surfactant or surfactants described above with one or more nonionic surfactants.

Nonionic Surfactants

Examples of suitable nonionic surfactants include, but are not limited to, alkyl alcohol ethoxylates, alkyl phenol ethoxylates, alkyl acid ethoxylates, alkyl amine ethoxylates, sorbitan alkanoates and ethoxylated sorbitan alkanoates.

Nonionic surfactants are generally known and include, for example, alkanolamides, which may optionally be alkoxylated, amine oxides, fatty alcohols, which may optionally be alkoxylated, alkoxylated alkyl phenols, fatty acids, fatty acid esters, and alkylglucosides, such as cocamide DEA, cocamide MIPA, PEG-5 cocamide MEA, lauramide DEA, lauramine oxide, cocamine oxide, stearamine oxide, stearamidopropylamine oxide, palmitamidopropylamine oxide, decylamine oxide, stearyl alcohol, sorbitan monolaurate, polysorbates, ethoxylated lauryl alcohols, polyethylene glycol distearates, dodecylglucoside, octadecylpolyglucosides, and mixtures thereof.

Examples of useful nonionic surfactants can additionally include condensates of ethylene oxide with a hydrophobic moiety which has an average hydrophilic lipophilic balance (HLB) between about 8 to about 16, and more preferably, between about 10 and about 12.5. These surfactants include the condensation products of primary or secondary aliphatic alcohols having from about 8 to about 24 carbon atoms, in either straight or branched chain configuration, with from about 2 to about 40, and preferably between about 2 and about 9 moles of ethylene oxide per mole of alcohol.

In a preferred embodiment the aliphatic alcohol comprises between about 9 and about 18 carbon atoms and is ethoxylated with between about 3 and about 12 moles of ethylene oxide per mole of aliphatic alcohol. Especially preferred are the about 12 to about 15 carbon primary alcohol ethoxylates containing about 5 to about 9 moles of ethylene oxide per mole of alcohol. One such material is commercially sold under the trade name NEODOL 25-9 by Shell Chemical Company. Other commercial nonionic surfactants include NEODOL 25-6.5 and NEODOL 25-7 sold by Shell Chemical Company.

Other suitable nonionic surfactants include the condensation products of about 6 to about 12 carbon atom alkyl phenols with about 3 to about 30, and preferably between about 5 and 14 moles of ethylene oxide. Examples of such surfactants are sold under the trade names IGEPAL CO 530, IGEPAL CO 630, IGEPAL C0720 and IGEPAL CO 730 by Rhodia, Inc. Still other suitable nonionic surfactants are described in U.S. Pat. No. 3,976,586. To the extent necessary, this patent is expressly incorporated by reference.

Most preferred for use are mixed linear alcohol ethoxylates such as Laureth-7 sold as RHODASURF L-790 by Rhodia, Inc.

In one embodiment, the nonionic surfactant comprises one or more of alkanolamides, amine oxides, fatty alcohols, alkoxylated fatty alcohols, fatty acids, and fatty acid esters.

Suitable alkanolamides include aliphatic acid alkanolamides, such as cocamide DEA, cocamide MIPA, cocamide MEA, PEG-5 cocamide MEA, lauramide DEA, and lauramide MEA, as well as alkoxylated alkanolamides, and mixtures thereof.

Suitable amine oxides comprise, saturated or unsaturated branched or straight chain ($C_{10}$-$C_{24}$) alkyl dimethyl oxides or ($C_{10}$-$C_{24}$) alkyl amidopropyl amine oxides, such as for example, lauramine oxide, cocamine oxide, stearamine oxide, stearamidopropylamine oxide, palmitamidopropylamine oxide, decylamine oxide as well as mixtures thereof.

Suitable fatty alcohols include, for example, saturated or unsaturated branched or straight chain ($C_{10}$-$C_{24}$) alcohols, more typically saturated or unsaturated branched or straight chain ($C_{10}$-$C_{24}$) alcohols, such as for example, decyl alcohol, lauryl alcohol, myristyl alcohol, cetyl alcohol, stearyl alcohol, oleyl alcohol, linoleyl alcohol and linolenyl alcohol, and mixtures thereof.

Suitable alkoxylated fatty alcohols include alkoxylated, typically ethoxylated, derivatives of saturated or unsaturated branched or straight chain ($C_{10}$-$C_{24}$) alcohols, more typically saturated or unsaturated branched or straight chain ($C_{10}$-$C_{24}$) alcohols, which may include, on average, from 1 to 22 alkoxyl units per molecule of alkoxylated alcohol, such as, for example, ethoxylated lauryl alcohol having an average of 5 ethylene oxide units per molecule. Mixtures of these alkoylated alcohols may be used.

Suitable fatty acids include saturated or unsaturated ($C_{10}$-$C_{24}$) carboxylic acids, more typically saturated or unsaturated ($C_{10}$-$C_{24}$) carboxylic acids, such as, for example, lauric acid, oleic acid, stearic acid, myristic acid, cetearic acid, isostearic acid, linoleic acid, linolenic acid, ricinoleic acid, elaidic acid, arichidonic acid, myristoleic acid, and palmitoleic acid, as well as neutralized versions thereof.

Suitable fatty acid esters include esters of saturated or unsaturated ($C_{10}$-$C_{24}$) carboxylic acids, more typically saturated or unsaturated ($C_{10}$-$C_{24}$) carboxylic acids, for example, propylene glycol isostearate, propylene glycol oleate, glyceryl isostearate, and glyceryl oleate, and mixtures thereof.

In one embodiment, the aqueous structured surfactant compositions of the present invention are each substantially free of alkanolamides, amine oxides, fatty alcohols, alkoxylated fatty alcohols, fatty acids, and/or fatty acid esters.

In one embodiment, the non-ionic surfactant is selected from non-ionic surfactants other than alkanolamides, amine oxides, fatty alcohols, alkoxylated fatty alcohols, fatty acids, and fatty acid esters. Suitable non-ionic surfactants other than alkanolamides, amine oxides, fatty alcohols, alkoxylated fatty alcohols, fatty acids, and fatty acid esters include, for example, compounds produced by the condensation of alkylene oxide groups with an organic hydrophobic compound, which may be aliphatic, or alkyl aromatic in nature. Typical nonionic surfactants consist of polyethylene, polypropylene, and polybutylene oxide condensates of alkyl phenols, and alkylpolyglycosides, and mixtures thereof.

Any effective amount of surfactant or blend of surfactants (effective to act as a surfactant) may be used in aqueous energized fluids of the invention. The fluids may incorporate the surfactant or blend of surfactants in an amount of about 0.02 wt % to about 5 wt % of total liquid phase weight, and more particularly from about 0.05 wt % to about 2 wt % of total liquid phase weight.

Latex Paints

The present invention includes an aqueous coating composition, comprising:

(a) the above-described mixture of at least a first cationic or cationizable polymer having a weight average molecular weight of 35,000 to 10,000,000, more typically in the range of about 200,000 to about 3,000,000 grams/mol, and at least a second anionic or hydrolyzable polymer having a weight average molecular weight of 30,000 g/mol to 10,000,000 g/mol, more typically to about 500,000 g/mole, and even more typically from about 150,000 g/mole to about 1,500,000 g/mole, for example about 1,000,000 g/mol or about 800,000 g/mole, wherein the composition has a zeta potential at 25° C. in the range of 0.5 to 100 mV or −0.5 to −100 mV, typically 1 to 60 mV or −1 to −60 mV, also typically 14 to 50 mV or −14 to −50 mV, also typically 30 to 50 mV or −30 to −50 mV or is a precursor convertible at a temperature of 100 to 250° C. to the composition having a zeta potential at 25° C. of 0.5 to 100 mV or −0.5 to −100 mV, typically 1 to 60 mV or −1 to −60 mV, also typically 14 to 50 mV or −14 to −50 mV, also typically 30 to 50 mV or −30 to −50 mV;

(b) at least one pigment;

(c) water;

(d) less than 5.0% by weight based on the total weight of the aqueous coating composition of anti-freeze agents.

The pigment is selected from at least one member of the group consisting of TiO2, clay, CaCO3, aluminum oxide, silicon dioxide, magnesium oxide, talc (magnesium silicate), barytes (barium sulfate), zinc oxide, zinc sulfite, sodium oxide, potassium oxide and mixtures thereof. The anti-freeze agents allow the paints to be used even after they have been subjected to freezing conditions. As mentioned above, the aqueous coating composition includes less than 5.0% of anti-freeze agents based on the total weight of the aqueous coating composition. Exemplary anti-freeze agents include ethylene glycol, diethylene glycol, propylene glycol, glycerol (1,2,3-trihydroxypropane), ethanol, methanol, 1-methoxy-2-propanol, 2-amino-2-methyl-1-propanol, and FTS-365 (a freeze-thaw stabilizer from Inovachem Specialty Chemicals). More typically, the aqueous coating composition includes less than 2.0%, less than 1.0% or is substantially free (e.g. includes less than 0.1%) of anti-freeze agents.

The polymeric thickeners of this invention are advantageous for use with the water-based compositions according to the foregoing description and with compositions containing those materials, especially coating compositions of various types. Mixtures or combinations of two or more thickeners may be used, if desired. Of course the latex polymers used in coating compositions are preferably film-forming at temperatures about 25° C. or less, either inherently or through the use of plasticizers. Such coating compositions include water-based consumer and industrial paints, sizing, adhesives and other coatings for paper, paperboard, textiles, and the like.

Latex paints and coatings may contain various adjuvants, such as pigments, fillers and extenders. Useful pigments include, but are not limited to, titanium dioxide, mica, and iron oxides. Useful fillers and extenders include, but are not limited to, barium sulfate, calcium carbonate, clays, talc, and silica. The compositions of the present invention described herein are compatible with most latex paint systems and provide highly effective and efficient thickening.

In latex paints, the composition is added such that the anionic polymer and cationic polymer according to the present invention are each present at about 0.05 to about 5.0 weight percent and preferably about 0.1 to about 3.0 weight percent based on total weight of the latex paint, including all of its components, such as water, anionic polymer, cationic polymer, latex polymer, pigment, and any adjuvants.

In formulating latexes and latex paints/coatings, physical properties that may be considered include, but are not limited to, viscosity versus shear rate, ease of application to surface, spreadability, and shear thinning.

The aqueous coating composition typically being a latex paint composition further comprising at least one latex polymer.

The latex polymer may be derived from at least one acrylic monomer selected from the group consisting of acrylic acid, acrylic acid esters, methacrylic acid, and methacrylic acid esters. The at least one latex polymer is typically selected from the group consisting of a pure acrylic latex polymer and a butyl acrylate/methyl methacrylate copolymer. Also, the at least one latex polymer is typically selected from the group consisting of pure acrylics, styrene acrylics, vinyl acrylics and acrylated ethylene vinyl acetate copolymers The aqueous coating composition typically further comprises one or more additives selected from the group consisting of binders, dispersants, coalescent agents, surfactants, rheology modifiers, defoamers, thickeners, biocides, mildewcides, colorants, waxes, perfumes and co-solvents.

Fracturing Fluids

The cationic polymer and anionic polymer may each be used in the fracturing fluid in an amount of from 0.01 to 5% by weight of the fluid.

Crosslinking Agent

A crosslinking agent may be used with the fracturing fluids. The crosslinking agents used may include aluminum or antimony or Group 4 transition metal compound crosslinking agents. The crosslinking agent may include zirconium, titanium and hafnium crosslinking agents, and combinations of these, and may include organo-metallic compounds. Examples of suitable zirconium crosslinking agents include zirconium triethanolamine, L-glutamic acid-triethanolamine-zirconium, zirconium diethanolamine, zirconium tripropanolamine, and zirconium lactate complexes, and/or the related salts, and/or their mixtures. Examples of titanium crosslinking agents include titanium triethanolamine, dihydroxybis(ammonium lactato)titanium, and titanium acetylacetonate. The crosslinking agent may be included in the fluid in an amount of from about 0.01% to about 1.5% by weight of the fluid, more particularly, from about 0.02% to about 0.3% by weight of the fluid.

Buffering Agent

A hydroxyl ion releasing agent or buffering agent may be employed to adjust the pH or buffer the fluid, i.e., moderate amounts of either a strong base or acid may be added without causing any large change in pH value of the fluid. These may useful in changing the rate of crosslinking. Alkaline amine or polyamine compounds that are useful to raise the pH to the desirable level are outlined in U.S. Pat. No. 4,579,670, and include tetramethylenediamine, triethylenetetramine, tetraethylenepentamine (TEPA), diethylenetriamine, triethylenediamine, triethylenepentamine, ethylenediamen and similar compounds. The alkali metal hydroxides, e.g., sodium hydroxide, and carbonates can also be used. Other acceptable materials are $Ca(OH)_2$, $Mg(OH)_2$, $Bi(OH)_3$, $Co(OH)_2$, $Pb(OH)_2$, $Ni(OH)_2$, $Ba(OH)_2$, and $Sr(OH)_2$. Acids such as hydrochloric acid, sulfuric acid, nitric acid, citric acid, acetic acid, fumaric acid, maleic acid, can be used to lower the pH.

In various embodiments, the buffering agent is a combination of a weak acid and a salt of the weak acid; an acid salt with a normal salt; or two acid salts. Examples of suitable buffering agents are acetic acid-Na acetate; $NaH_2PO_4$—$Na_2PO_4$; sodium carbonate-sodium bicarbonate; and sodium bicarbonate, or other like agents. By employing a buffering agent instead of merely a hydroxyl ion producing material, a fluid is provided which is more stable to a wide range of pH values found in local water supplies and to the influence of acidic materials located in formations and the like.

Gas Component

The fracturing fluids may contain a gas component, as discussed above. The gas component may be provided from any suitable gas that forms an energized fluid or foam when introduced into the aqueous medium. See, for example, U.S. Pat. No. 3,937,283 (Blauer, et al.), hereinafter incorporated by reference. The gas component may comprise a gas selected from nitrogen, air, argon, carbon dioxide, and any mixtures thereof. Particularly useful are the gas components of nitrogen or carbon dioxide, in any quality readily available. The gas component may assist in the fracturing, and also the capacity of the fluid to carry solids, such as proppants. The presence of the gas also enhances the flowback of the fluid to facilitate cleanup. The fluid may contain from about 10% to about 90% volume gas component based upon total fluid volume percent, more particularly from about 20% to about 80% volume gas component based upon total fluid volume percent, and more particularly from about 30% to about 70% volume gas component based upon total fluid volume percent.

Breaker

Fracturing fluids based on the invention may also comprise a breaker. The purpose of this component is to "break" or diminish the viscosity of the fluid so that this fluid is more easily recovered from the formation during cleanup. With regard to breaking down viscosity, oxidizers, enzymes, or acids may be used. Breakers reduce the polymer's molecular weight by the action of an acid, an oxidizer, an enzyme, or some combination of these on the polymer itself. The breakers may include persulfates such as ammonium persulfate, sodium persulfate, and potassium persulfate, bromates such as sodium bromate and potassium bromate, periodates, metal peroxides such as calcium peroxide, chlorites, and the like, and the combinations of these breakers, live or encapsulated.

Proppant

Embodiments of the invention used as fracturing fluids may also include proppant particles that are substantially insoluble in the fluids of the formation. Proppant particles carried by the treatment fluid remain in the fracture created, thus propping open the fracture when the fracturing pressure is released and the well is put into production. Suitable proppant materials include, but are not limited to, sand, walnut shells, sintered bauxite, glass beads, ceramic materials, naturally occurring materials, or similar materials. Mixtures of proppants can be used as well. If sand is used, it will typically be from about 20 mesh (0.841 mm) to about 100 mesh (0.0059 mm) in size. With synthetic proppants, mesh sizes of about 8 (0.937 mm) or greater may be used. Naturally occurring materials may be underived and/or unprocessed naturally occurring materials, as well as materials based on naturally occurring materials that have been processed and/or derived. Suitable examples of naturally occurring particulate materials for use as proppants include, but are not necessarily limited to: ground or crushed shells of nuts such as walnut, coconut, pecan, almond, ivory nut, brazil nut, etc.; ground or crushed seed shells (including fruit pits) of seeds of fruits such as plum, olive, peach, cherry, apricot, etc.; ground or crushed seed shells of other plants such as maize (e.g., corn cobs or corn kernels), etc.; processed wood materials such as those derived from woods such as oak, hickory, walnut, poplar, mahogany, etc. including such woods that have been processed by grinding, chipping, or other form of particalization, processing, etc. Further information on nuts and composition thereof may be found in Encyclopedia of Chemical Technology, Edited by Raymond E. Kirk and Donald F. Othmer, Third Edition, John Wiley & Sons, Volume 16, pages 248-273 (entitled "Nuts"), Copyright 1981, which is incorporated herein by reference.

The concentration of proppant in the fluid can be any concentration known in the art, and will preferably be in the range of from about 0.03 to about 3 kilograms of proppant added per liter of liquid phase. Also, any of the proppant particles can further be coated with a resin to potentially improve the strength, clustering ability, and flow back properties of the proppant.

Aqueous Media

The aqueous medium of the fracturing fluids of the present invention may be water or brine. In those embodiments of the invention where the aqueous medium is a brine, the brine is water comprising an inorganic salt or organic salt. Inorganic salts may include alkali metal halides, such as potassium chloride. The carrier brine phase may also comprise an organic salt, such as sodium or potassium formate. Inorganic divalent salts include calcium halides, such as calcium chloride or calcium bromide. Sodium bromide, potassium bromide, or cesium bromide may also be used. The salt may be chosen for compatibility reasons i.e. where the reservoir drilling fluid used a particular brine phase and the completion/clean up fluid brine phase is chosen to have the same brine phase. Typical salt levels are 2 to 30 wt % salt based on overall composition of the aqueous brine. The most common level of salt in brine is 2-10 weight % sodium chloride, potassium chloride or mixtures thereof based on overall composition of the aqueous brine.

Fiber Component

A fiber component may be included in the fracturing fluids of the invention to achieve a variety of properties including improving particle suspension, and particle transport capabilities, and gas phase stability. Fibers used may be hydrophilic or hydrophobic in nature, but hydrophilic fibers may be useful for some applications. Fibers can be any fibrous material, such as, but not necessarily limited to, natural organic fibers, comminuted plant materials, synthetic polymer fibers (by non-limiting example polyester, polyaramide, polyamide, novoloid or a novoloid-type polymer), fibrillated synthetic organic fibers, ceramic fibers, inorganic fibers, metal fibers, metal filaments, carbon fibers, glass fibers, ceramic fibers, natural polymer fibers, and any mixtures thereof. Particularly useful fibers are polyester fibers coated to be highly hydrophilic, such as, but not limited to, DACRON® polyethylene terephthalate (PET) fibers available from Invista Corp. Wichita, Kans., USA, 67220. Other examples of useful fibers include, but are not limited to, polylactic acid polyester fibers, polyglycolic acid polyester fibers, polyvinyl alcohol fibers, and the like. When used in fluids of the invention, the fiber component may be include at concentrations from about 1 to about 15 grams per liter of the liquid phase of the fluid, in certain applications the concentration of fibers may be from about 2 to about 12 grams per liter of liquid, and in others from about 2 to about 10 grams per liter of liquid.

Other Optional Ingredients

Fluid embodiments of fracturing fluids of the invention may further contain other additives and chemicals that are known to be commonly used in oilfield applications by those skilled in the art. These include, but are not necessarily limited to, materials such as surfactants in addition to those mentioned herein, clay stabilizers such as tetramethyl ammonium chloride and/or potassium chloride, breaker aids in addition to those mentioned herein, oxygen scavengers, alcohols, scale inhibitors, corrosion inhibitors, fluid-loss additives, bactericides, and the like. Also, they may include a co-surfactant to optimize viscosity or to minimize the formation of stable emulsions that contain components of crude oil or a polysaccharide or chemically modified polysaccharide, polymers such as cellulose, derivatized cellulose, guar gum, derivatized guar gum, xanthan gum, or synthetic polymers such as polyacrylamides and polyacrylamide copolymers, oxidizers such as ammonium persulfate and sodium bromate, and biocides such as 2,2-dibromo-3-nitrilopropionamine. The fluid should be substantially devoid of hectorite clay or other clay components and such components may be present in the fluid only in amounts of less than 0.1% by weight.

Aqueous fluid embodiments of the invention may also comprise an organoamino compound. Examples of suitable organoamino compounds include, but are not necessarily limited to, tetraethylenepentamine (TEPA), triethylenetetramine, pentaethylenehexamine, triethanolamine, and the like, or any mixtures thereof. When organoamino compounds are used in fluids of the invention, they are incorporated at an amount from about 0.01 wt % to about 2.0 wt % based on total liquid phase weight. The organoamino compound may be incorporated in an amount from about 0.05 wt % to about 1.0 wt % based on total weight of the fluid. A particularly useful organoamino compound is tetraethylenepentamine (TEPA).

Hydraulic Fracturing Techniques

The fluids of the invention may be used for hydraulically fracturing a subterranean formation. Techniques for hydraulically fracturing a subterranean formation are known to persons of ordinary skill in the art, and involve pumping the fracturing fluid into the borehole and out into the surrounding formation. The fluid pressure is above the minimum in situ rock stress, thus creating or extending fractures in the formation. See Stimulation Engineering Handbook, John W. Ely, Pennwell Publishing Co., Tulsa, Okla. (1994), U.S. Pat. No. 5,551,516 (Normal et al.), "Oilfield Applications", Encyclopedia of Polymer Science and Engineering, vol. 10, pp. 328-366 (John Wiley & Sons, Inc. New York, N.Y., 1987) and references cited therein, the disclosures of which are incorporated herein by reference thereto.

In the fracturing treatment, fluids of the present invention may be used in the pad treatment, the proppant stages, or both. The components of the liquid phase may be mixed on the surface. Alternatively, the fluid may be prepared on the surface and pumped down tubing while any gas component could be pumped down the annulus to mix down hole, or vice versa.

The fluids of the invention have particular application for use in high temperature environments. In particular, the fluids may be used in treatments where temperatures of 120° C. to 230° C. or higher are encountered. The fluids have particular application for use in environments of from 300° F. (148.9° C.), 325° F. (162.8° C.), 350° F. (176.7° C.) to 375° F. (190° C.), 400° F. (204.4° C.), 425° F. (218.3° C.) or 450° F. (232.2° C.).

In hydraulic fracturing the fracturing fluid comprising water soluble polymer and at least one nonionic surfactant is pumped into the targeted formation at a rate in excess of what can be dissipated through the natural permeability of the formation rock. The fracturing fluids result in a pressure build up until such pressure exceeds the strength of the formation rock. When this occurs, the formation rock fails and a so-called "fracture" is initiated. With continued pumping, the fracture grows in length, width and height.

At a predetermined time in the pumping process, solid particulate is typically added to the fluid that is being pumped. This particulate is carried down the well, out of the wellbore and deposited in the created fracture. It is the purpose of this specially designed particulate to keep the fracture from "healing" to its initial position (after pumping has ceased). The particulate is said to be propping open the fracture and is therefore designated as "proppant". The fracture, which is generated by the application of this stimulation technique, creates a conductive path to the wellbore for the hydrocarbon.

Typical proppant is selected from the group consisting of gravel, quartz sand grains, sintered bauxite, glass and ceramic beads, walnut shell fragments, or aluminum pellets. The fracturing fluid may also include a thermal stabilizer, for example sodium thiosulfate, methanol, ethylene glycol, isopropanol, thiourea, and/or sodium thiosulfite. The fracturing fluid may also include KCl as a clay stabilizer.

Acidizing

Producing oil and gas wells have long been treated to stimulate production thereof utilizing a method termed "acidizing" in which an emulsion of an aqueous mineral acid either alone or in combination with various surfactants, corrosion inhibiting agents, and hydrocarbon oils is added to a producer well. Presumably, such treatments tend to remove deposits from the area of the subterranean oil or gas formation immediately adjacent to the production well bore, thus increasing the permeability of the formation and allowing residual oil or gas to be recovered through the well bore. Another object of such "acidizing" treatment of oil or gas producer wells is the removal of water from the interstices of the formation by the use of a composition which materially lowers the interfacial forces between the water and the oil or gas. Various surface-active agents have been recommended for this use.

Producing oil and gas wells have long been treated to stimulate production thereof utilizing a method termed "acidizing" in which an emulsion of an aqueous mineral acid either alone or in combination with various surfactants, corrosion inhibiting agents, and hydrocarbon oils is added to a producer well. Presumably, such treatments tend to remove deposits from the area of the subterranean oil or gas formation immediately adjacent to the production well bore, thus increasing the permeability of the formation and allowing residual oil or gas to be recovered through the well bore. Another object of such "acidizing" treatment of oil or gas producer wells is the removal of water from the interstices of the formation by the use of a composition which materially lowers the interfacial forces between the water and the oil or gas. Various surface-active agents have been recommended for this use.

Acidizing, and fracturing procedures using acidic treatment fluids, are commonly carried out in subterranean well formations to accomplish a number of purposes including, but not limited to, to facilitate the recovery of desirable hydrocarbons from the formation. As used herein, the term "treatment fluid" refers to any fluid that may be used in a subterranean application in conjunction with a desired function and/or for a desired purpose. The term "treatment fluid" does not imply any particular action by the fluid or any component thereof.

One commonly used aqueous acidic treatment fluid comprises hydrochloric acid. Other commonly used acids for acidic treatment fluids include hydrofluoric acid, acetic acid, formic acid, citric acid, ethylene diamine tetra acetic acid ("EDTA"), glycolic acid, sulfamic acid, and derivatives or combinations thereof.

Acidic treatment fluids are used in various subterranean operations. For example, formation acidizing or "acidizing" is a method for, among other purposes, increasing the flow of desirable hydrocarbons from a subterranean formation. In a matrix acidizing procedure, an aqueous acidic treatment fluid is introduced into a subterranean formation via a well bore therein under pressure so that the acidic treatment fluid flows into the pore spaces of the formation and reacts with (e.g., dissolves) the acid-soluble materials therein. As a result, the pore spaces of that portion of the formation are enlarged, and the permeability of the formation may increase. The flow of hydrocarbons from the formation therefore may be increased because of the increase in formation conductivity caused, inter alia, by dissolution of the formation material. In fracture acidizing procedures, one or more fractures are produced in the formation(s) and an acidic treatment fluid is introduced into the fracture(s) to etch flow channels therein. Acidic treatment fluids also may be used to clean out well bores to facilitate the flow of desirable hydrocarbons. Other acidic treatment fluids may be used in diversion processes and well bore clean-out processes. A specific example is filter cake removal.

To increase the viscosity of an aqueous acidic treatment fluid, a suitable gelling agent may be included in the treatment fluid (often referred to as "gelling" the fluid). Gelling an aqueous acidic treatment fluid may be useful, among other purposes, to prevent the acid from becoming prematurely spent and inactive. Additionally, gelling an aqueous acidic treatment fluid may enable the development of wider fractures so that the gelled acidic treatment fluid may delay the interaction of the acid with an acid soluble component in the well bore or the formation. Moreover, gelling an aqueous acidic treatment fluid may permit better fluid loss control.

Acidic treatment fluids used in subterranean operations are predominantly water-based fluids that comprise gelling agents to increase their viscosities. Common gelling agents include polysaccharides (such as xanthan), synthetic polymers (such as polyacrylamide), and surfactant gel systems. To assist the gelling agents in maintaining these viscosities in the presence of the high temperatures and slat concentrations experienced downhole the composition includes the polymer combinations of the present invention.

The aqueous base fluids of the acidic treatment fluids of the present invention generally comprise fresh water, salt water, sea water, a brine (e.g., a saturated salt water or formation brine), or a combination thereof. Other water sources may be used, including those comprising monovalent, divalent, or trivalent cations (e.g., magnesium, calcium, zinc, or iron) and, where used, may be of any weight. If a water source is used that contains such divalent or trivalent cations in concentrations sufficiently high to be problematic, then such divalent or trivalent salts may be removed, either by a process such as reverse osmosis, or by raising the pH of the water in order to precipitate out such divalent salts to lower the concentration of such salts in the water before the water is used. Another method would be to include a chelating agent to chemically bind the problematic ions to prevent their undesirable interactions with the clarified xanthan. Suitable chelants include, but are not limited to, citric acid or sodium citrate, ethylene diamine tetra acetic acid ("EDTA"), hydroxyethyl ethylenediamine triacetic acid ("HEDTA"), dicarboxymethyl glutamic acid tetrasodium salt ("GLDA"), diethylenetriaminepentaacetic acid ("DTPA"), propylenediaminetetraacetic acid ("PDTA"), ethylenediaminedi(o-hydroxyphenylacetic) acid ("EDDHA"), glucoheptonic acid, gluconic acid, and the like, and nitrilotriacetic acid ("NTA"). Other chelating agents also may be suitable. One skilled in the art will readily recognize that an aqueous base fluid containing a high level of multi-valent ions should be tested for compatibility prior to use.

The gelling agents comprising the polymers of the present invention may be present in an acidic treatment fluid of the present invention in an amount of from about 1 lb/Mgal to about 200 lb/Mgal. In embodiments wherein the gelling agents comprising clarified xanthan further comprise scleroglucan, one may include about 1 lb/Mgal to about 200 lb/Mgal of scleroglucan. In an acidic treatment fluid that comprises hydrochloric acid, one may include about 1 to about 200 lb/Mgal of scleroglucan. In embodiments wherein the gelling agents comprising clarified xanthan further comprise diutan, one may include about 1 to about 200 lb/Mgal of diutan. In an acidic treatment fluid that comprises about 15% hydrochloric acid, one may include about 1 to about 200 lb/Mgal of diutan. In some embodiments, one may include about 10 to about 150 lb/Mgal of clarified xanthan, scleroglucan, and/or diutan. A person of skill in the art with the benefit of this disclosure will recognize that any specific concentration or narrower range of concentrations of the gelling agents of the present invention encompassed by the broader concentration ranges specifically articulated above may be used and/or may be particularly advantageous for a particular embodiment of the present invention.

In certain embodiments, the acidic treatment fluids of the present invention also may comprise any additional additive that may be suitable in a particular application of the present invention, including, but not limited to, any of the following: hydrate inhibitors, clay stabilizers, bactericides, salt substitutes (such as tetramethyl ammonium chloride), relative permeability modifiers (such as HPT-1™ chemical additive available from Halliburton Energy Services, Duncan, Okla.), sulfide scavengers, fibers, nanoparticles, consolidating agents (such as resins and/or tackifiers), corrosion inhibitors, corrosion inhibitor intensifiers, pH control additives, surfactants, breakers, fluid loss control additives, scale inhibitors, asphaltene inhibitors, paraffin inhibitors, salts, bactericides, crosslinkers, stabilizers, chelants, foamers, defoamers, emulsifiers, demulsifiers, iron control agents, solvents, mutual solvents, particulate diverters, gas phase, carbon dioxide, nitrogen, other biopolymers, synthetic polymers, friction reducers, combinations thereof, or the like. The acidic treatment fluids of the present invention also may include other additives that may be suitable for a given application, as will be recognized by a person of ordinary skill in the art, with the benefit of this disclosure.

While typically not required, the acidic treatment fluids of the present invention also may comprise breakers capable of reducing the viscosity of the acidic treatment fluid at a desired time. Examples of such breakers that may be suitable for the acidic treatment fluids of the present invention include, but are not limited to, sodium chlorite, hypochlorites, perborates, persulfates, peroxides (including organic peroxides), enzymes, derivatives thereof, and combinations thereof. Other suitable breakers may include suitable acids. Examples of peroxides that may be suitable include tert-butyl hydroperoxide and tert-amyl hydroperoxide. A breaker may be included in an acidic treatment fluid of the present invention in an amount and form sufficient to achieve the desired viscosity reduction at a desired time. The breaker may be formulated to provide a delayed break, if desired. For example, a suitable breaker may be encapsulated if desired. Suitable encapsulation methods are known to those skilled in the art. One suitable encapsulation method that may be used involves coating the breaker(s) with a material that will degrade when placed downhole so as to release the breaker at the appropriate time. Coating materials that may be suitable include, but are not limited to, polymeric materials that will degrade when downhole. The terms "degrade," "degradation," or "degradable" refer to both the two relatively extreme cases of hydrolytic degradation that the degradable material may undergo, i.e., heterogeneous (or bulk erosion) and homogeneous (or surface erosion), and any stage of degradation in between these two. This degradation can be a result of, inter alia, a chemical or thermal reaction or a reaction induced by radiation. Suitable examples of materials that can undergo such degradation include polysaccharides such as dextran or cellulose; chitins; chitosans; proteins; aliphatic polyesters; poly(lactides); poly(glycolides); poly(.epsilon.-caprolactones); poly(hydroxybutyrates); poly(anhydrides); aliphatic polycarbonates; orthoesters, poly(orthoesters); poly(amino acids); poly(ethylene oxides); polyphosphazenes; derivatives thereof; and combinations thereof. If used, a breaker should be included in a composition of the present invention in an amount sufficient to facilitate the desired reduction in viscosity in a viscosified treatment fluid. For instance, peroxide concentrations that may be used vary from about 0.1 to about 10 gallons of peroxide per 1000 gallons of the acidic treatment fluid.

Enhanced Oil Recovery

The present invention may be employed with other techniques to further improve hydrocarbon recovery from subterranean formations. Initially, oil is produced from the fractured formation by pressure depletion (primary recovery). In this method, the differential pressure between the formation and a production well or wells forces the oil contained within the formation toward a production well where it can be recovered. Traditionally secondary recovery processes through injection of water or gas are used to displace additional oil toward producing wells. Typically, up to about 35 percent of the oil which is initially contained in a formation can be recovered in average through primary and secondary recovery. This leaves a large quantity of oil within the formation. Additionally, some formations contain oil which is too viscous to be efficiently recovered from the formation using primary and secondary processes. Because of the need to recover a larger percentage of the oil from a formation, methods have been developed to recover oil which could not be recovered using only pressure depletion techniques. These methods are typically referred to as "enhanced oil recovery techniques" (EOR).

Thus, the present invention is also directed to a method for recovering crude oil from a subterranean formation, comprising introducing to the formation an aqueous medium comprising water or brine and the composition of the present invention including a combination of anionic polymer and cationic polymer described above.

The global average recovery factor for conventional oil fields is about 35% and it could be raised up to 50% through enhanced oil recovery. There are two essentials components to EOR: improving displacement efficiency and improving macroscopic sweep efficiency. The present invention enhances oil recovery by maintaining stable viscosity at high temperatures. The method of the invention is particularly useful in the stimulation of oil and gas wells which have failed to respond to acidizing treatment of the producing well including the use of various acids with various surfactants.

Chemical Flooding

A promising EOR method is an enhanced oil recovery process referred to as chemical flooding which generally covers the use of polymer and/or surfactant slugs. In polymer flooding, a polymer solution is injected to displace oil toward producing wells. The polymer solution is designed to develop a favorable mobility ratio between the injected polymer solution and the oil/water bank being displaced ahead of the polymer. However, the use of polymer is not always satisfactory as many polymer solutions are sensitive to brine type and concentration which can affect the apparent viscosity of the solution. In surfactant flooding, an aqueous solution containing surfactant is injected into the oil rich formation. Residual oil drops are deformed as a result of low Interfacial Tension provided by surfactant solution and drops are displaced through the pore throats and displaced oil is the recovered. See U.S. Pat. No. 7,789,160 to Hough et al. incorporated herein by reference in its entirety.

The present compositions advantageously are compatible with anionic surfactants typically used to decrease interfacial tension to also assist in enhancing oil recovery from subterranean formations.

The present invention proves enhanced oil recovery. For example, the present invention is also directed to a method for recovering crude oil from a subterranean formation, comprising introducing to the formation an aqueous medium comprising water or brine and the composition of the present invention including a combination of polyanionic polymer and polycationic polymer described above.

There are two essentials components to EOR: improving displacement efficiency and improving macroscopic sweep efficiency. The present invention enhances oil recovery by maintaining stable viscosity at high temperatures. The method of the invention is particularly useful in the stimulation of oil and gas wells which have failed to respond to acidizing treatment of the producing well including the use of various acids with various surfactants.

The present compositions advantageously are compatible with anionic surfactants typically used to decrease interfacial tension to also assist in enhancing oil recovery from subterranean formations.

The aqueous medium of the composition may be soft water, brackish water or brine. Typically the aqueous medium in compositions used to treat subterranean formations comprises brine.

Other Ingredients

It should be also understood the compositions of the invention may contain components in addition to water, the first cationic or cationaizable polymer, the second anionic or anionizable polymer and optional surfactants. Such additional components are, for example, co-solvents, acids, bases, buffers, chelating agents for the control of multivalent cations, freezing point depressants, etc.

For example, a hydrocarbon recovery composition according to the present invention may be provided to the hydrocarbon containing formation alone or with other compounds for enhancing oil recovery. For example, these other compounds may be other nonionic additives (e.g., alcohols, ethoxylated alcohols and/or sugar based esters). Some embodiments have less than 0.3 weight percent of one or more anionic surfactants (e.g. sulfates, sulfonates, ethoxylated sulfates, and/or phosphates). In some embodiments the composition has less than 0.3 wt % each of anionic surfactant, amphoteric surfactant and zwitterionic surfactant. If desired, there may be an absence of anionic surfactant, an absence of amphoteric surfactant, and an absence of zwitterionic surfactant.

Alcohol

Alcohol can be used as mutual solvent to reduce water saturation. The interfacial tension between oil and ethanol is much lower than between oil and brine.

Capillary forces of retention for the alcohol are much reduced compared to those for brine.

It has been reported that isopropyl or butyl alcohol plus methyl alcohol could be used in miscible displacement to increase oil recovery of naphtha and mineral oil.

Others have investigated enhanced oil recovery by alcohol flooding. Their process design was strongly guided by the ternary phase of alcohol/oil/brine. They showed that oil recovery was highly dependent on the choice of alcohol/oil/brine combinations. Others have reported that injection of appropriate combinations of oil-soluble and water-soluble solvents such as alcohols and ketones could significantly enhance oil recovery.

In an embodiment, an aliphatic nonionic additive may be used in a hydrocarbon recovery composition. As used herein, the term "aliphatic" refers to a straight or branched chain of carbon and hydrogen atoms. In some embodiments, an aliphatic portion of an aliphatic nonionic additive may have an average carbon number from 10 to 24. In some embodiments, an aliphatic portion of an aliphatic nonionic additive may have an average carbon number from 12 to 18. In some embodiments, the aliphatic nonionic additive may include a branched aliphatic portion. A branched aliphatic portion of an aliphatic nonionic additive may have an average carbon number from 16 to 17. In some embodiments, a branched aliphatic group of an aliphatic nonionic additive may have less than about 0.5 percent aliphatic quaternary carbon atoms. In an embodiment, an average number of branches per aliphatic nonionic additive ranges from about 0.1 to about 2.5. In other embodiments, an average number of branches per aliphatic nonionic additive ranges from about 0.7 to about 2.5.

Methyl branches may represent between about 20 percent to about 99 percent of the total number of branches present in the branched nonionic additive. In some embodiments, methyl branches may represent greater than about 50 percent of the total number of branches in a branched nonionic additive. The number of ethyl branches in the alcohol may represent, in certain embodiments, less than about 30 percent of the total number of branches. In other embodiments, the number of ethyl branches, if present, may be between about 0.1 percent and about 2 percent of the total number of branches. Branches other than methyl or ethyl, if present, may be less than about 10 percent of the total number of branches. In some embodiments, less than about 0.5 percent of the total number of branches are neither ethyl nor methyl groups.

In an embodiment, an aliphatic nonionic additive may be a long chain aliphatic alcohol. The term "long chain," as used herein, refers to a carbon chain having an average carbon number from 10 to 30. A long chain aliphatic alcohol (e.g., a long chain primary alcohol) may be purchased commercially (e.g., NEODOL alcohols manufactured by Shell Chemical Co., Houston, Tex.). In certain embodiments, a long chain aliphatic alcohol may be prepared by a variety of generally known methods. A long chain aliphatic alcohol may have an average carbon number from 10 to 24. In some embodiments, a long chain aliphatic alcohol may have an average carbon number from 12 to 18. In other embodiments, a long chain aliphatic alcohol may have an average carbon number from 16 to 17.

In an embodiment, a portion of the long chain aliphatic alcohol may be branched. Branched long chain aliphatic alcohols may be prepared by hydroformylation of a branched olefin. Preparations of branched olefins are described in U.S.

Pat. No. 5,510,306 to Murray, entitled "Process for Isomerizing Linear Olefins to Isoolefins;" U.S. Pat. No. 5,648,584 to Murray, entitled "Process For Isomerizing Linear Olefins to Isoolefins" and U.S. Pat. No. 5,648,585 to Murray, entitled "Process For Isomerizing Linear Olefins to Isoolefins," all of which are incorporated by reference herein. Preparations of branched long chain aliphatic alcohols are described in U.S. Pat. No. 5,849,960 to Singleton et al., entitled "Highly Branched Primary Alcohol Compositions, and Biodegradable Detergents Made Therefrom;" U.S. Pat. No. 6,150,222 to Singleton et al., entitled "Highly Branched Primary Alcohol Compositions, and Biodegradable Detergents Made Therefrom;" U.S. Pat. No. 6,222,077 to Singleton et al., entitled "Highly Branched Primary Alcohol Compositions, and Biodegradable Detergents Made Therefrom," all of which are incorporated by reference herein.

In some embodiments, branches of a branched aliphatic group of a long chain aliphatic alcohol may have less than about 0.5 percent aliphatic quaternary carbon atoms. In an embodiment, an average number of branches per long chain aliphatic alcohol ranges from about 0.1 to about 2.5. In other embodiments, an average number of branches per alcohol ranges from about 0.7 to about 2.5.

Methyl branches may represent between about 20 percent to about 99 percent of the total number of branches present in the branched long chain aliphatic alcohol. In some embodiments, methyl branches may represent greater than about 50 percent of the total number of branches in a branched long chain aliphatic alcohol. The number of ethyl branches in the alcohol may represent, in certain embodiments, less than about 30 percent of the total number of branches. In other embodiments, the number of ethyl branches, if present, may be between about 0.1 percent and about 2 percent of the total number of branches. Branches other than methyl or ethyl, if present, may be less than about 10 percent of the total number of branches. In some embodiments, less than about 0.5 percent of the total number of branches are neither ethyl nor methyl groups.

Aliphatic Anionic Surfactants

In an embodiment, an aliphatic anionic surfactant may be used in a hydrocarbon recovery composition. In certain embodiments, an aliphatic portion of an aliphatic anionic surfactant may have an average carbon number from 10 to 24. In some embodiments, an aliphatic portion of an aliphatic anionic surfactant may have an average carbon number from 12 to 18. In other embodiments, an aliphatic portion of an aliphatic anionic surfactant may have an average carbon number from 16 to 17. In some embodiments, the aliphatic anionic surfactant may include a branched aliphatic portion. In some embodiments, a branched aliphatic group of an aliphatic anionic surfactant may have less than about 0.5 percent aliphatic quaternary carbon atoms. In an embodiment, an average number of branches per aliphatic anionic surfactant ranges from about 0.1 to about 2.5. In other embodiments, an average number of branches per aliphatic anionic surfactant ranges from about 0.7 to about 2.5.

Methyl branches may represent between about 20 percent to about 99 percent of the total number of branches present in the branched anionic surfactant. In some embodiments, methyl branches may represent greater than about 50 percent of the total number of branches in a branched anionic surfactant. The number of ethyl branches in the alcohol may represent, in certain embodiments, less than about 30 percent of the total number of branches. In other embodiments, the number of ethyl branches, if present, may be between about 0.1 percent and about 2 percent of the total number of branches. Branches other than methyl or ethyl, if present, may be less than about 10 percent of the total number of branches. In some embodiments, less than about 0.5 percent of the total number of branches are neither ethyl or methyl groups.

In an embodiment which further employs aliphatic anionic surfactant, a solution may provided which contains an effective amount of an aliphatic anionic surfactant selected from the group of compounds having the general formula: $R_1O(C_3H_6O)_m(C_2H_4O)_nYX$ wherein $R_1$ is a linear or branched alkyl radical, an alkenyl radical, or an alkyl or alkenyl substituted benzene radical, the non-aromatic portion of the radical containing from 6 to 24 carbon atoms; m has an average value of from 1 to 10; n has an average value of from 1 to 10; Y is a hydrophilic group; and X is a cation, preferably monovalent, for example N, K, $NH_4^+$. Y is a suitable hydrophilic group or substituted hydrophilic group such as, for example, the sulfate, sulfonate, phosphonate, phosphate or carboxylate radical. Preferably, $R_1$ is a branched alkyl radical having at least two branching groups and Y is a sulfonate or phosphate group.

Other Optional Additives for Enhanced Oil Recovery

The aqueous fluid of the present invention may, optionally, further comprise clay stabilization or sand stabilization material. During oil recovery processes, sands and other materials may become entrained in the recovered oil. This may be mitigated by the addition of a clay stabilization or sand stabilization material. Suitable clay stabilization or sand stabilization materials include epoxy resins, polyfunctional cationic polymers, such as poly(N-acrylamidomethyltnmethyl ammonium chloride) or poly(vinylbenzyltrimethyl ammonium chloride).

Other optional ingredients that may be added to the aqueous fluid of the present invention include, but are not limited to polymers such as biopolysaccharides, cellulose ethers, acrylamide-derived polymers, corrosion inhibitors, oxygen scavengers, bactericides, and so forth, and any combination thereof.

The aqueous fluid of the present invention is introduced into the crude oil-bearing formation, typically by injecting the fluid into the formation.

In the case of a carbonate formation having hydrophobic surfaces, addition of the organophosphorous material to the aqueous flooding fluid modifies such surfaces to increase the surface energy of such surfaces and render such surfaces more readily wettable by water. The surface modified formation more readily imbibes the aqueous flooding fluid, thus increasing the amount of aqueous fluid imbibed by the formation and increasing the amount of crude oil displaced from the formation by the aqueous fluid.

The aqueous fluid may be used in secondary or tertiary oil recovery processes, although the use of such fluids in other applications is also not excluded.

Methods of Use for Enhanced Oil Recovery

The aqueous medium utilized to form the solution including the organophosphorous material of the invention can be soft water, brackish water, or a brine. The aqueous fluid of the present invention is introduced into the crude oil-bearing formation, typically by injecting the fluid into the formation.

Optionally, after injection of the aqueous fluid comprising the present phosphate esters of the present invention addition to crude oil having generally the viscosity of the oil-bearing formation of the oil well to be treated, various hydrocarbon solvents may be employed to displace the aqueous solution out into the reservoir. Such hydrocarbon solvents as the low molecular weight, generally liquid hydrocarbons boiling below the gasoline range, such as the lower alkanes including butane, propane, pentane, hexane and heptane, as well as natural gasoline, petroleum naphtha and kerosene or mixtures of these hydrocarbons, are useful. Both sweet and sour crude oil is useful as a hydrocarbon to displace the aqueous solution out into the subterranean reservoir of oil or gas.

Optionally, injection of a preflush fluid may be utilized prior to injection of the aqueous fluid of the present invention. The preflush may consist of a hydrocarbon fluid, a brine solution, or simply water.

Also, injection of the aqueous fluid comprising the present phosphate esters may optionally be followed by an injection of a surfactant, a mobility control fluid or a polymeric flush, which is typically a polymer-thickened aqueous solution, using, for example the polymers disclosed above, into the formation to further enhance oil recovery. The polymeric solution is utilized to drive or push the now oil bearing surfactant flood out of the reservoir, thereby "sweeping" crude oil out of the reservoir. Further, the polymeric solution has a very high viscosity which helps to prevent what is referred to in the industry as channeling or "fingering", thus improving sweep efficiency.

This polymeric flush or mobility control fluid may once again be followed by a water flush which may be brine or saline or softened water, or fresh water.

Oil is recovered at a production well spaced apart from the injection well as the drive fluid pushes the mobility buffer slug which sweeps the oil out of the pores in the formation and to the production well. Once the water/oil emulsion reaches the surface, it is put into holding tanks where it is subsequently demulsified, thereby allowing the oil to separate from the water through the natural forces of gravity.

For example, a hydrocarbon recovery composition including the phosphate esters of the present invention may be added to a portion of hydrocarbon containing formation that may have an average temperature of less than 80° C. To facilitate delivery of an amount of the hydrocarbon recovery composition to the hydrocarbon containing formation, the hydrocarbon composition may be combined with water or brine to produce an injectable fluid. Typically about 0.01 to about 5 wt % of the phosphate ester, based on the total weight of injectable fluid, may be injected into the hydrocarbon containing formation through an injection well. In certain embodiments, the concentration of the hydrocarbon recovery composition injected through the injection well may be about 0.05% to about 3 wt. %, based on the total weight of injectable fluid. In some embodiments, the concentration of the hydrocarbon recovery composition may be about 0.1% to about 1 wt. % based on the total weight of injectable fluid.

In some embodiments, a hydrocarbon recovery composition may be added to a portion of a hydrocarbon containing formation.

Personal Care Compositions

The polymer of the present invention of the present invention is suitable in the preparation of personal care (cosmetics, toiletries, health and beauty aids, cosmeceuticals) and topical health care products, including without limitation, hair care products, such as shampoos (including combination shampoos, such as "two-in-one" conditioning shampoos), post-shampoo rinses, setting and style maintenance agents including setting aids, such as gels and sprays, grooming aids, such as pomades, conditioners, perms, relaxers, hair smoothing products, and the like, skin care products (facial, body, hands, scalp and feet), such as creams, lotions, conditioners, and cleansing products, anti-acne products, anti-aging products (exfoliant, keratolytic, anticellulite, antiwrinkle, and the like), skin protectants such as sunscreens, sunblock, barrier creams, oils, silicones, and the like, skin color products (whiteners, lighteners, sunless tanning accelerators, and the like), hair colorants (hair dyes, hair color rinses, highlighters, bleaches and the like), pigmented skin colorants (face and body makeups, foundation creams, mascara, rouge, lip products, and the like), bath and shower products (body cleansers, body wash, shower gel, liquid soap, soap bars, syndet bars, conditioning liquid bath oil, bubble bath, bath powders, and the like), nail care products (polishes, polish removers, strengtheners, lengtheners, hardeners, cuticle removers, softeners, and the like), and any aqueous acidic to basic composition to which an effective amount of the associative polymer can be incorporated for achieving a beneficial or desirable, physical or chemical, effect therein during storage and/or usage.

In one embodiment, the present invention is directed to a personal care composition comprising water, one or more surfactants, and a polymer of the present invention.

In one embodiment, the personal care composition comprises, based on 100 parts by weight ("pbw") of the personal care composition, from about 10 to about 80 pbw, more typically from about 20 to about 70 pbw, water, from about 1 to about 50 pbw of one or more surfactants, and from about 0.05 to about 10 pbw, more typically from about 0.1 to about 5 pbw, of the polymer of the present invention.

Suitable surfactants include anionic surfactants, cationic surfactants, amphoteric surfactants, zwitterionic surfactants, nonionic surfactants, and mixtures thereof.

In one embodiment of the composition, the combination of anionic polymers and cationic polymers of the present invention is an effective thickener, that is, the polymer increases the viscosity of the composition, that is responsive, but not overly sensitive, to salt content and or surfactant content, particularly at a pH of greater than or equal to 6.5.

In one embodiment, the personal care composition further comprises, based on 100 pbw of the composition, from greater than 0 to about 30 pbw, more typically from about 0.1 to about 20 pbw, still more typically from about 0.25 to about 10 pbw, still more typically from about 0.5 pbw to about 6 pbw, of one or more non-surfactant electrolytes. Suitable non-surfactant electrolytes include, for example, alkali metal, alkaline earth, ammonium and substituted ammonium salts of inorganic acids, including, for example, calcium chloride, calcium carbonate, potassium chloride, sodium chloride, potassium iodide, sodium bromide, magnesium chloride, sodium sulfate, calcium nitrate, ammonium bromide, ammonium sulfate, ammonium nitrate.

In one embodiment, the personal care composition further comprises one or more benefit agents.

Suitable benefit agents include materials that provide a personal care benefit, such as moisturizing, conditioning, or a sensory benefit, to the user of the personal care composition, such as, for example, emollients, conditioners, moisturizers, polymers, vitamins, abrasives, UV absorbers, antimicrobial agents, anti-dandruff agents, fragrances, and/or appearance modifying additives, such as, for example, colored particles or reflective particles, which may be in the form of a solid, liquid, or gas and may be insoluble or are only partly soluble in the personal care composition. Mixtures of the benefit agents may be used.

In one embodiment, the benefit agent comprises an oil useful as an emollient, or conditioner for the skin or hair. Suitable oils, include for example, vegetable oils, such as arachis oil, castor oil, cocoa butter, coconut oil, corn oil, cotton seed oil, olive oil, palm kernel oil, rapeseed oil, safflower seed oil, sesame seed oil, and soybean oil, esters of ($C_{12}$-$C_{22}$) carboxylic acids, such as butyl myristate, cetyl palmitate, decyloleate, glyceryl laurate, glyceryl ricinoleate, glyceryl stearate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, propylene glycol monolaurate, propylene glycol ricinoleate, propylene glycol stearate, and propylene glycol isostearate, animal fats, such as lanoliin, mink oil, and tallow, hydrocarbon oils, such as mineral oils and petrolatum, and silicone oils, such as polydimethylsiloxanes, polydiethylsiloxanes, polymethylphenylsiloxanes, alkoxylated polyorganosiloxanes, amino-substituted polyorganosiloxanes, amido-substituted polyorganosiloxanes, and mixtures thereof.

In one embodiment, the benefit agent comprises a moisturizer. Suitable moisturizers include, for example, glycerin and hyaluronic acid.

In one embodiment, the benefit agent comprises a cationic polymer and/or an amphoteric polymer. Suitable cationic polymers include synthetic polymers that comprise monomeric units derived from one or more amine- and/or quaternary ammonium-substituted monomers and natural polymers that have been derivatized to include amine- and/or quaternary ammonium-containing pendant groups, each typically having a cationic charge density of from about 0.1 to 4 meq/g. Suitable cationic polymers include, for example: copolymers of 1-vinyl-2-pyrrolidine and 1-vinyl-3-methyl-imidazolium salts (such as Polyquaternium-16), copolymers of 1-vinyl-2-pyrrolidine and dimethylaminoethyl methacrylate (such as Polyquaternium-11), cationic diallyl quaternary ammonium-containing polymers including, for example, dimethyldiallyammonium chloride homopolymers and copolymers of acrylamide and dimethyldiallylammonium chloride (such as Polyquaternium 6 and Polyquaternium 7), cationic polyacrylamides, cationic polysaccharide polymers, such as, for example, cationic cellulose derivatives, cationic starch derivatives, and cationic guar gum derivatives, such as salts of hydroxyethyl cellulose reacted with trimethyl ammonium substituted epoxide (such as Polyquaternium 10), polymeric quaternary ammonium salts of hydroxyethyl cellulose reacted with lauryl dimethyl ammonium-substituted epoxide (such as Polyquaternium 24) and guar hydroxypropyltrimonium chloride, and cationic protein derivatives, such as cocodimonium hydroxypropyl hydrolyzed wheat protein. Suitable amphoteric polymers are polymers that contain both anionic groups, such as phosphate, phosphonate, sulphate, sulphonate or carboxylic acid groups, and cationic groups, such as tertiary amino groups or quaternary ammonium groups, on the same polymer molecule. Suitable amphoteric polymers include, for example, amphoteric acrylic copolymers, such as octylacrylamide/acrylate/butylaminoethyl methacrylate copolymers, and amphoteric polysaccharide compounds obtained by grafting and polymerization of cationic pendant groups, e.g., dimethyldiallylammonium chloride groups, onto anionic polysaccharide, for example, a sodium carboxymethyl-cellulose, backbone Aqueous compositions containing the polymer of the present invention, one or more surfactants and/or non-surfactants salts, and a cationic polymer and/or amphoteric polymer exhibit an enhanced thickening efficiency compared to analogous compositions that lack the cationic polymer and/or amphoteric polymer.

In one embodiment, the personal care benefit agent Is selected from the group consisting of oil, mica, exfoliation beads, emollients, moisturizers, pearlizing agent, a silicone hair conditioning agent, an antidandruff ingredient, a glycol emulsifier.

In another embodiment the composition is for cleaning hair or skin and comprises:
the polymer,
at least one detersive surfactant, and
at least one member of the group consisting of oil, mica, exfoliation beads, emollients, moisturizers, pearlizing agent, a silicone hair conditioning agent, an antidandruff ingredient, a glycol emulsifier provided that a 10% aqueous solution of said composition has a pH from about 4 to about 12.

In one embodiment, the benefit agent comprises an anti-dandruff agent. Suitable anti-dandruff agents include, for example, particulate, crystalline anti-dandruff agents, such as sulfur, selenium disulfide, and heavy metal salts of pyridinethione, such as zinc pyrithione, as well as soluble anti-dandruff agents, such as ketoconazole.

In one embodiment, the composition is a shampoo comprising a personal care benefit agent comprises one or more hair conditioning oils, one or more hair benefit agents other than a hair conditioning oil, or one or more hair conditioning oils and one and more hair benefit agents other than a hair conditioning oil.

In one embodiment, the benefit agent comprises a UV radiation absorber. Suitable UV radiation absorbers include, for example, sodium benzotriazolyl butylphenol sulfonate.

The personal care composition according to the present invention may optionally further comprise, based on 100 pbw of the personal care composition and independently for each such ingredient, up to about 10 pbw, typically from 0.5 pbw to about 5.0 pbw, of other ingredients in addition to the one or more benefit agents, including, for example, preservatives such as benzyl alcohol, methyl paraben, propyl paraben and imidazolidinyl urea, pH adjusting agents such as citric acid, succinic acid, phosphoric acid, sodium hydroxide, sodium carbonate, dyes, and sequestering agents such as disodium ethylenediamine tetra-acetate. Other examples of ingredients commonly used in personal care compositions, which are suitable for use in the compositions of the present invention, are known and are described in, for example, in *Cosmetic Ingredient Handbook*, Eighth Edition, 2000.

In one embodiment, the personal care composition is a body wash that comprises, based on 100 pbw of the composition, from about 0.1 to about 5 pbw, more typically from about 0.5 to about 3 pbw, from of the polymer of the present invention, from about 1 to about 30 pbw, more typically from about 1 to about 20 pbw of one or more surfactants, more typically of a mixture of one or more anionic surfactants with one or more zwitterionic or amphoteric surfactants, and optionally, one or more non-surfactant salts.

In one embodiment of the personal care composition, the polymer of the present invention is an effective thickener, that is, the polymer increases the viscosity of the personal care composition, that is responsive, but not overly sensitive, to salt content and or surfactant content, particularly at a pH of greater than or equal to 6.5. More specifically, the viscosity of an aqueous composition comprising the polymer of the present invention typically increases with increasing surfactant content and/or non-surfactant salt content in a predictable and proportional manner and does not typically undergo undesirably large changes in viscosity in response to relatively small changes in the amount of surfactants and/or non-surfactant salts.

In one embodiment of the personal care composition, the polymer of the present invention imparts a yield strength to the composition that is greater than 0 Pa, more typically of from about 0.01 Pa, and even more typically from about 0.1 to about 10 Pa, and even more typically about 4 Pa, and even more typically about 2 Pa. A non-zero yield strength is useful for suspending water insoluble particles in the personal care composition. As previously mentioned, the polymer of the present invention typically provides a yield strength of greater than 0 Pa even in the absence of any cross-linking of the polymer.

In one embodiment of the personal care composition wherein the personal care composition has a pH of greater than or equal to 6.5, the polymer of the present invention provides thickening properties and imparts a non-zero yield strength in the presence of surfactant without imparting an optically turbid appearance to the composition, thus allowing formulation of optically clear compositions having a non-zero yield strength.

In one embodiment of the personal care composition, typically wherein the personal care composition has a pH of greater than or equal to about 6.5, the polymer of the present invention provides thickening properties and imparts a non-zero yield strength in the presence of surfactants and/or non-surfactant salts and the composition clear, transparent visual appearance, for example, a transmittance at 600 nm of greater than 95%.

In one embodiment of the personal care composition, typically wherein the personal care composition has a pH of less than about 6.5, the polymer of the present invention provides thickening properties and imparts a non-zero yield strength in the presence of surfactants and/or non-surfactant salts, and imparts an opaque visual appearance to the composition. Also, a higher yield strength can typically be obtained with given polymer content at a pH of less than 6, compared to a composition having a pH of greater than or equal to 6.5.

In one embodiment of the personal care composition the polymer of the present invention provides high foam volume. In an embodiment of the personal care composition that comprises a cationic polymer, the polymer of the present invention provides high foam volume and reduces drainage, resulting in a wet, creamy, shiny, white foam.

In one embodiment of the personal care composition the polymer of the present invention provides good sensory properties, such as, for example a smooth, velvety feel and a lack of tacky feeling on the skin.

In one embodiment of the personal care composition, the polymer of the present invention is easily rinsed from the skin with water, leaving minimal or no perceptible polymer residue on the skin.

The present invention also includes a method for promoting personal care comprising applying the composition of the present invention to skin or hair of a user.

Home Care of Industrial Care Compositions

In one embodiment, the present invention is directed to a home care or industrial cleaning composition, such as a liquid detergent, a laundry detergent, a hard surface cleanser, a dish wash liquid, or a toilet bowl cleaner, comprising water, one or more surfactants, and a polymer of the present invention. Suitable surfactants include those described above in regard to the personal care composition embodiments of the present invention. Such cleaning compositions may optionally further comprise one or more of water miscible organic solvents, such as alcohols and glycols, and/or one or more additives.

Suitable additives are known in the art and include, for example, organic builders, such as organophosphonates, inorganic builders, such as ammonium polyphosphates, alkali metal pyrophosphates, zeolites, silicates, alkali metal borates, and alkali metal carbonates, bleaching agents, such as perborates, percarbonates, and hypochlorates, sequestering agents and anti-scale agents, such as citric acid and ethylenediaminetetraacetic acid, inorganic acids, such as phosphoric acid and hydrochloric acid, organic acids, such as acetic acid, abrasives, such as silica or calcium carbonate, antibacterial agents or disinfectants, such as triclosan and cationic biocides, for example (N-alkyl)benzyldimethylammonium chlorides, fungicides, enzymes, opacifing agents, pH modifiers, dyes, fragrances, and preservatives.

In an embodiment the home care or industrial cleaner benefit agent is selected from the group consisting of soil release agents, fabric softener, surfactants, builders, binders, bleach and fragrances.

In an embodiment the home care or industrial cleaning composition for cleaning fabrics or hard surfaces comprising, the composition of the present invention and a surfactant and a home care or industrial cleaner benefit agent.

In an embodiment the composition is a detergent composition and comprises: the polymer, at least one detersive surfactant, and a builder.

The invention also encompasses a method for cleaning a substrate selected from the group consisting of a hard surface and a fabric, comprising applying the composition of the present invention to the substrate.

EXAMPLES

HASE Polymer Synthesis Example A

The following example is presented to illustrate the preparation and properties of the fluids and should not be construed to limit the scope of the invention, unless otherwise expressly indicated in the appended claims. All percentages, concentrations, ratios, parts, etc. are by weight unless otherwise noted or apparent from the context of their use.

Typical families of RHODIA HASE polymers include those of RHODIA HASE Polymer X, RHODIA HASE Polymer Y and RHODIA HASE Polymer Z.

RHODIA HASE Polymer X was composed of two different types of specialty hydrophobic macro monomers, which are Macro Monomer I and Macro Monomer II.

Macro Monomer I was a monomer made from NOPOL alcohol ("NOPOL polyether monomer"). The general family of these momoners is represented in Formula A.XXX (which repeats above-presented Formula A.XIII):

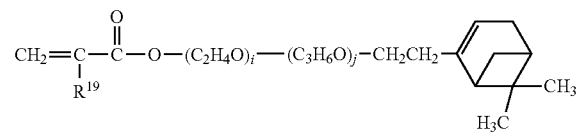

A.XXX wherein i, j, and $R^{19}$ are each as described above. Typically i and j are 1 to 200, for example 5 to 30. More typically, i is an integer of from 10 to 40, and even more typically from 15 to about 30, and j is an integer of from 1 to 20, and even more typically from about 2 to about 10.

Macro Monomer II was made from a mixture of C22, C16 and C18 linear alkyl chains ("$(C_{16}-C_{22})$alkyl-polyether monomer"). It was a branched macro monomer.

The general family of this embodiment of Macro Monomer II is represented by structure A.XXXI (which repeats above-presented Formula A.XX):

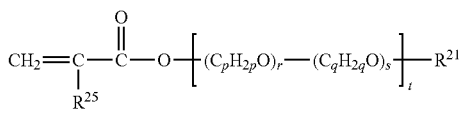
(A.XXXI)

wherein

R²¹ is linear or branched ($C_5$-$C_{50}$)alkyl, hydroxyalkyl, alkoxyalkyl, aryl, or aralkyl, R²⁵ is methyl or ethyl, and p, q, r, s, and t are each as described above. For example: wherein:

p and q are independently integers of from 2 to 5, more typically 2 or 3, each r is independently an integer of from 1 to about 80, more typically from 1 to about 50, each s is independently an integer of from 0 to about 80, more typically from 0 to about 50, t is an integer of from 1 to about 50, provided that the product obtained by multiplying the integer t times the sum of r+s is from 2 to about 100.

An idealized structural formula for RHODIA HASE Polymer X is shown by structural formula A.XXXII. As mentioned above, RHODIA HASE Polymer X was composed of Macro Monomer I and Macro Monomer II.

dently from 1 to 200, typically 5 to 30. More typically, i is an integer of from 10 to 40, and even more typically from 15 to about 30, and j is an integer of from 1 to 20, and even more typically from about 2 to about 10.

The ingredients used to make HASE Polymer X are summarized in TABLE 4.

The HASE Polymer X contained:

first monomeric units derived from a monomeric compound according to structure (XXX) above, wherein R¹⁹=methyl, i=25, and j=5 ("NOPOL polyether monomer, Macro monomer I"), second monomeric units derived from a mixture of ($C_{16}$-$C_{22}$)alkyl-polyethoxylated methacrylates having an average of 25 ethylene oxide units per molecule, according to structure (XXXI), wherein R²⁵ is methyl, R²¹ is a mixture of linear $C_{16}$ alkyl, linear $C_{18}$ alkyl, and linear $C_{22}$ alkyl groups, p=2, r=25, s=0, and t=1 ("($C_{16}$-$C_{22}$)alkyl-polyether monomer, Macro Monomer II"), third monomeric units derived from methacrylic acid ("MAA"), and fourth monomeric units derived from ethyl acrylate ("EA").

Although not synthesized as part of the samples represented in TABLE 4, if desired a HASE Polymer Y comprising Macro Monomer I but not Macro Monomer II could have been blended with a HASE Polymer Z comprising Macro Monomer II but not Macro Monomer I. An idealized struc-

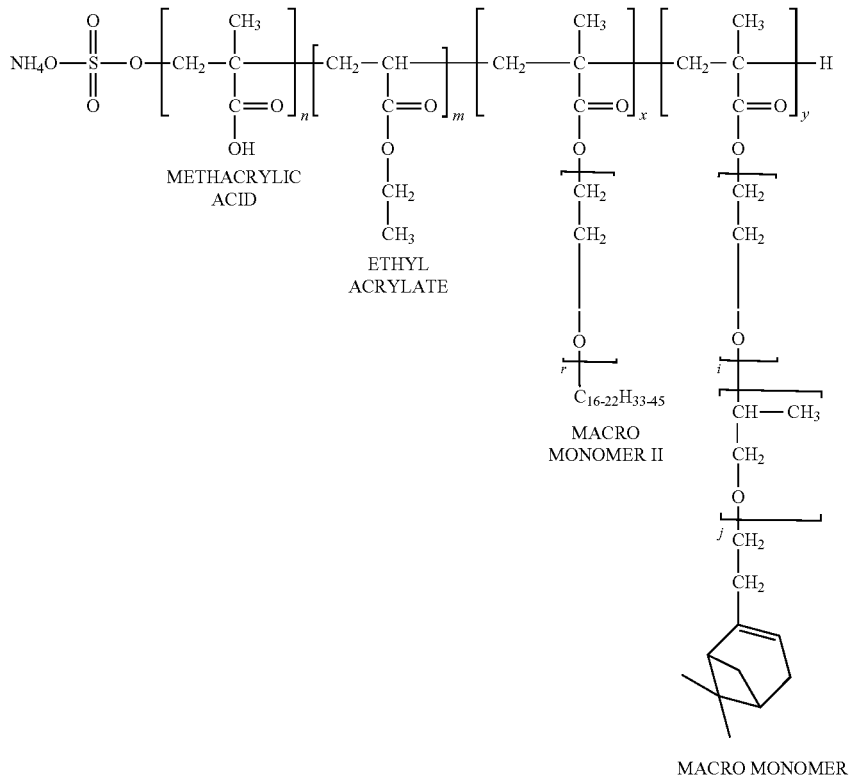

A.XXXII, RHODIA HASE Polymer X

In general for Formula A.XXXII for HASE Polymer X parameters n, m, x and y are sufficient to obtain the desired molecular weight and anionic charge density (ACD); parameter r is an integer from 1 to about 80, more typically an integer from 1 to about 50; parameters i and j are indepentural formula of HASE Polymer Y is shown by structural formula A.XXXIII, wherein y and z are independently from 1 to 200, typically 5 to 30. More typically, y is an integer of from 10 to 40, and even more typically from 15 to about 30, and z is an integer of from 1 to 20, and even more typically from about 2 to about 10. Parameters n, m and x are sufficient to achieve the desired molecular weight. HASE Polymer Y would be the same as HASE Polymer Z but substitute Macro Monomer II of formula A.XXXII for Macro Monomer I.

A.XXXIII, RHODA HASE Polymer Y

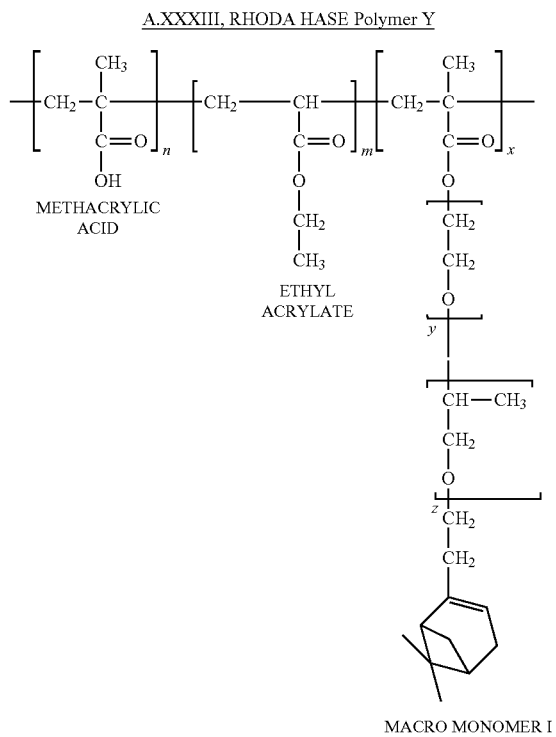

MACRO MONOMER I

HASE Polymers X, Y and Z can be synthesized by emulsion polymerization using conventional radical polymerization. They contain methacrylic acids which contains carboxylic groups which make the polymer anionic.

The following shows a method to make HASE Polymers of the type of RHODIA HASE Polymer X containing Macro Monomers I and II but are not necessarily how HASE polymers of other examples in this specification were made.

To make RHODIA HASE Polymers of the type of RHODIA HASE Polymer X the NOPOL polyether monomer was introduced in the form of an aqueous emulsion ("NOPOL polyether monomer emulsion") that contained, based on 100 pbw of the emulsion, about 50 pbw of the NOPOL polyether monomer and about 25 pbw MAA. The ($C_{16}$-$C_{22}$)alkyl-polyether monomer was introduced in the form of an aqueous emulsion ("($C_{16}$-$C_{22}$)alkyl-polyether emulsion") that contained, based on 100 pbw of the emulsion, about 50 pbw of the ($C_{16}$-$C_{22}$)alkyl-polyether monomer and about 25 pbw MAA. TABLE 4 shows samples S1, S2 and S3 of compositions for making HASE Polymer X.

TABLE 4

| | Charges (grams) | | |
|---|---|---|---|
| | Sample S1 | Sample S2 | Sample S3 |
| Kettle charge | | | |
| Water | 323.9 | 322.8 | 382.8 |
| RHODAPEX AB20 (sulfated alcohol ethoxylate, 29% solids content) | 2.07 | 5.17 | 2.07 |

TABLE 4-continued

| | Charges (grams) | | |
|---|---|---|---|
| | Sample S1 | Sample S2 | Sample S3 |
| Monomer emulsion | | | |
| Water | 300.0 | 300.0 | 300.0 |
| RHODAPEX AB20 (sulfated alcohol ethoxylate, 29% solids content) | 20.7 | 51.7 | 20.7 |
| Ethyl Acrylate (EA) | 159.0 | 159.0 | 144.0 |
| Methacrylic acid (MAA) | 111.0 | 111.0 | 96.0 |
| NOPOL polyether monomer emulsion | 24.0 | 24.0 | 60.0 |
| ($C_{16}$-$C_{22}$) alkyl-polyether monomer emulsion | 36.0 | 36.0 | 60.0 |
| Initiator solution | | | |
| Ammonium persulfate | 0.84 | 0.84 | 0.42 |
| Water | 79.7 | 79.7 | 39.8 |
| Chaser solution Part 1: | | | |
| t-butylperoxybenzoate | 0.60 | 0.60 | 0.60 |
| Part 2: | | | |
| Water | 19.7 | 19.7 | 19.7 |
| Erythorbic acid | 0.30 | 0.30 | 0.30 |
| Total | 1077.8 | 1110.8 | 1126.4 |

The relative amounts of the monomeric units in the each of the respective polymers of Samples S1, S2 and S3 are given in TABLE 5A, as weight percent of total monomers charged and as mole percent of total monomers charged. The average particle size, as determined by light scattering, of each of the latex polymers of Synthesis Samples S1, S2, and S3 are also given in TABLE 5A.

TABLE 5A

| | Sample S1 | Sample S2 | Sample S3 |
|---|---|---|---|
| NOPOL polyether monomer | | | |
| wt % | 3.8 | 3.8 | 9.1 |
| mole % | 0.3 | 0.3 | 0.7 |
| ($C_{16}$-$C_{22}$) alkyl-polyether monomer | | | |
| wt % | 5.7 | 5.7 | 9.1 |
| mole % | 0.4 | 0.4 | 0.7 |
| MAA | | | |
| wt % | 40.00 | 40.00 | 38.2 |
| mole % | 47.6 | 47.6 | 49.8 |
| EA | | | |
| wt % | 50.5 | 50.5 | 43.6 |
| mole % | 51.7 | 51.7 | 48.9 |
| Average particle size (nm) | 103 | 71 | 94 |

Additional samples of HASE polymers synthesized are as listed in TABLES 5B and 5C. Samples S4-S17 contain NOPOL polyether (Macromonomer I) and ($C_{16}$-$C_{22}$) alkyl polyether (Macromonomer II) and thus are of HASE polymer X type. Samples C1-C4 contain NOPOL polyether or ($C_{16}$-$C_{22}$) alkyl polyether and thus are of HASE polymer Y or Z type. Some examples include polyethyleneglycol 400 dimethacrylate (PEG400DMA Li) or ethylene glycol dimethacrylate (EGDMA).

TABLE 5B

Samples with NOPOL polyether and ($C_{16}$-$C_{22}$) alkyl polyether

| Monomer | S4 | S5 | S6 | S7 | S8 | S9 | S10 | S11 | S12 |
|---|---|---|---|---|---|---|---|---|---|
| NOPOL polyether | 4.76 | 6.60 | 3.81 | 3.77 | 3.74 | 1.94 | 3.85 | 5.71 | 5.61 |
| ($C_{16}$-$C_{22}$) alkyl polyether | 4.76 | 4.72 | 5.71 | 7.55 | 9.35 | 3.88 | 3.85 | 3.81 | 7.48 |
| MAA | 40.00 | 39.79 | 40.00 | 39.79 | 39.58 | 40.43 | 40.21 | 40.00 | 39.58 |
| EA | 50.48 | 48.89 | 50.48 | 48.89 | 47.33 | 53.74 | 52.09 | 50.48 | 47.33 |
| EGDMA | — | — | — | — | — | — | — | — | — |
| PEG400DMA Li | — | — | — | — | — | — | — | — | — |

TABLE 5C

| | Samples with NOPOL polyether and ($C_{16}$-$C_{22}$) alkyl polyether | | | | | Samples with NOPOL polyether or ($C_{16}$-$C_{22}$) alkyl polyether | | | |
|---|---|---|---|---|---|---|---|---|---|
| Monomer | S13 | S14 | S15 | S16 | S17 | C1 | C2 | C3 | C4 |
| NOPOL polyether | 7.51 | 9.30 | 3.87 | 3.80 | 5.75 | 4.88 | 0 | 9.52 | 0.00 |
| ($C_{16}$-$C_{22}$) alkyl polyether | 4.69 | 4.65 | 1.94 | 5.71 | 1.92 | 0 | 4.88 | 0.00 | 9.52 |
| MAA | 39.69 | 39.48 | 40.31 | 39.94 | 40.10 | 41.46 | 41.46 | 40.00 | 40.00 |
| EA | 48.11 | 46.56 | 53.58 | 50.40 | 51.94 | 53.66 | 53.66 | 50.48 | 50.48 |
| EGDMA | — | — | 0.31 | — | — | — | — | — | — |
| PEG400DMA Li | — | — | — | 0.15 | 0.29 | — | — | — | — |

Example 1

Several HASE polymers listed in TABLE 6 were screened at room temperature. The HASE (Hydrophobically-modified Alkali Swellable Emulsion) polymer was composed of hydrophilic groups (methacrylic acid and ethyl acrylate) and hydrophobic groups (Macro monomer I and, in some cases, Macro monomer II). The HASE Polymers listed in TABLE 6 were synthesized by emulsion polymerization using conventional radical polymerization. They contain methacrylic acids which contains carboxylic groups which make the polymer anionic.

The compositions of HASE polymers used are presented in TABLE 6.

TABLE 6

| HASE Sample numbers | Methacrylic acid (phm) | Ethyl Acrylate (phm) | Macro Monomer I (phm) | Internal cross Linker[1] (grams) | Chain transfer agent[2] (grams) | Initiator (gr) | PO/EO units Macro Monomer I |
|---|---|---|---|---|---|---|---|
| A | 41.0 | 55.0 | 4.0 | — | — | 0.375 | 5/15 |
| B | 41.0 | 55.0 | 4.0 | — | — | 0.375 | 10/25 |
| C | 41.0 | 55.0 | 4.0 | — | — | 0.375 | 15/40 |
| D | 41.0 | 55.0 | 4.0 | — | — | 0.375 | 5/25 |
| E | 41.0 | 55.0 | 4.0 | 0.56 | 0.81 | 0.375 | 5/25 |
| F | 41.0 | 55.0 | 4.0 | 0.56 | — | 0.375 | 5/25 |

[1] Ethylene glycol dimethyl acrylate
[2] 1-Dodecanethiol
[3] The term "phm" means monomers per hundred monomers of polymer.

The resulting HASE polymer had approximately 30% active level of polymer. The procedure of making the HASE solution and testing it in the Brookfield PVS rheometer for this and other examples in this specification, unless otherwise indicated, is described below.

1. 100 mL of salt solution was made. Several different salt solutions were used, but the typical salt used was 2% KCl solution, which was prepared by mixing 2 grams of KCl with 98 mL of distilled water.

2. If necessary, the appropriate amount of polycationic solution was added. For cationic guar, it was important to hydrate the solution by adding 0.5 mL of 25% acidic acid buffer and leaving it for at least 30 minutes.

3. This solution was sheared for approximately one minute to make sure the polycationic was dissolved.

4. The appropriate amount of HASE cationic polymer was added slowly under high shear.

5. The base was added to increase the pH to around 11-12.5. High shear was needed because the basic condition would tremendously increase the solution viscosity. The solution was sheared until the latex and the polycationic were mixed evenly and no chunk observed.

6. Approximately 35 to 40 grams of sample was put into the sample cup for Brookfield test.

TABLE 7 contains the results of constant shear viscosities at room temperatures. Concentration=3%; Shear rate=0.5 or 1 rpm.

TABLE 7

HASE Polymers

| Sample | PO length | EO length | EO/PO | XL | chain Trans | viscosity in Water viscosity cps at rpm 0.5 | 1 | viscosity in 2% KCl viscosity cps at rpm 0.5 | 1 |
|---|---|---|---|---|---|---|---|---|---|
| A | 5  | 15 | 3 | n | n | 4687 | 3750 | 3984 | 2812 |
| B | 10 | 25 | 3 | n | n | 1594 | 797  | 844  | 422  |
| C | 15 | 40 | 3 | n | n | 1406 | 750  | 844  | 328  |
| D | 5  | 25 | 5 | n | n | 2906 | 1734 | 1406 | 938  |
| E | 5  | 25 | 5 | y | y | 187  | 117  | 281  | 176  |
| F | 5  | 25 | 5 | y | n | 9000 | 4781 | 700  | 469  |

Figure 4:
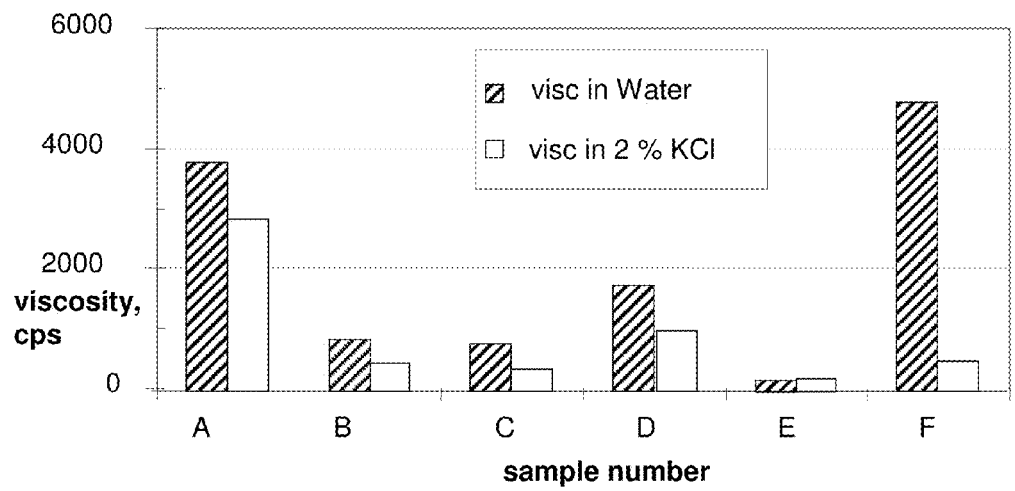
FIG. 4 shows a plot of data of Example 1.

Sample A has the best tolerance to salt. This data is plotted in FIG. 4 (Table 7 Example 1).

Example 2

3% HASE Polymer A, pH 12, 2% KCl

The following HASE polymers listed in TABLE 8 were formulated. TABLE 9 provides additional information.

TABLE 8

Composition of HASE polymer

| HASE Sample | Methacrylic Acid (phm)** | Ethyl Acrylate (phm) | Macro Monomer I (phm) | Macro Monomer II (phm) | Internal Cross-linker Mass (grams)* | Initiator Mass (grams) |
|---|---|---|---|---|---|---|
| A | 40.83 | 55.17 | 4.00 | | | 0.375 |
| G | 40.83 | 55.17 | 4.00 | | 0.557 | 0.375 |
| H | 40.83 | 55.17 | 4.00 | | 1.114 | 0.375 |
| I | 37.34 | 52.66 | 1.67 | 8.33 | | 0.25 |
| J | 39.83 | 56.17 | 2.00 | 2.00 | | 0.25 |
| K | 37.34 | 52.66 | 5.00 | 5.00 | | 0.25 |
| L | 37.34 | 52.66 | 1.67 | 8.33 | | 0.124 |

*The internal crosslinker was ethylene glycol dimethyl acrylate
**The term "phm" means monomers per hundred monomers of polymer.

TABLE 9

Monomer Emulsion Composition by Weight

| HASE Sample | Total Mass (grams) | Methacrylic Acid (grams) | Ethyl Acrylate (wt %) | Macro Monomer I (wt %) | Ethylene glycol dimethyl acrylate | Macro Monomer II (wt %) |
|---|---|---|---|---|---|---|
| A | 320.33 | 15.78 | 25.83 | 6.12 | | |
| G | 320.91 | 15.74 | 25.79 | 6.11 | 0.17 | |
| H | 321.46 | 15.72 | 25.74 | 6.10 | 0.35 | |
| I | 285.98 | 16.71 | 27.04 | 1.71 | | 8.51 |

The resulting HASE polymer had approximately 30% active level of polymer. The procedure of making the HASE solution and testing it in the Brookfield PVS rheometer was described below.

1. 100 mL of salt solution was made. Several different salt solutions were used, but the typical salt used was 2% KCl solution, which was prepared by mixing 2 grams of KCl with 98 mL of distilled water.
2. If necessary, the appropriate amount of polycationic solution was added. For cationic guar, it was important to hydrate the solution by adding 0.5 mL of 25% acidic acid buffer and leaving it for at least 30 minutes.
3. This solution was sheared for approximately one minute to make sure the polycationic was dissolved.
4. The appropriate amount of HASE cationic polymer was added slowly under high shear.
5. The base was added to increase the pH to around 11-12.5. High shear was needed because the basic condition would tremendously increase the solution viscosity. The solution was sheared until the latex and the polycationic were mixed evenly and no chunk observed.
6. Approximately 35 to 40 grams of sample was put into the sample cup for Brookfield test.

Figure 5:
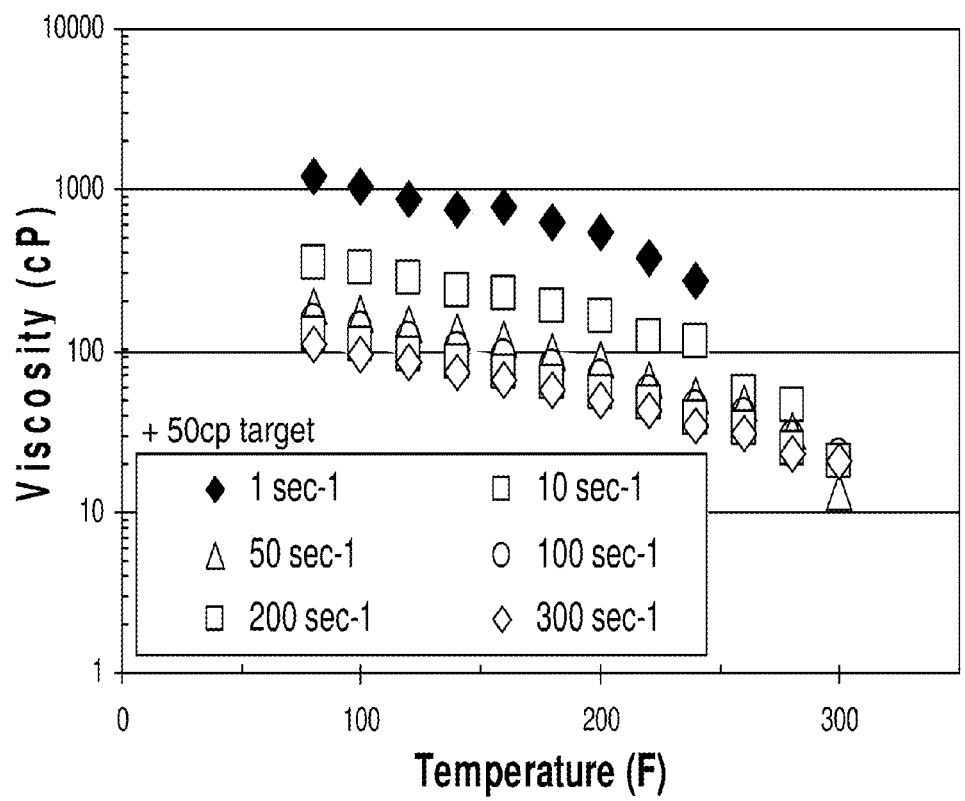
FIG. 5 shows a plot of data of Example 2 for the results of high temperature, high pressure rheology tests of a mixture of 3 wt. % HASE polymer A, at a pH of 12 with 2% KCl.

FIG. 5 shows the results of high temperature, high pressure rheology tests of a mixture of 3 wt. % HASE polymer A, at a pH of 12 with 2% KCl. Typical desired minimum viscosity is 50 cps at 180° F. HASE polymer A can achieve this at 220-230° F. Thus, viscosity is less than 50 cps at temperatures above 220-230° F. In FIG. 5 shear rate is expressed in units of $\sec^{-1}$.

Example 3

3 wt. % HASE Polymer G pH 11 in 2 wt. % KCl

Figure 6:
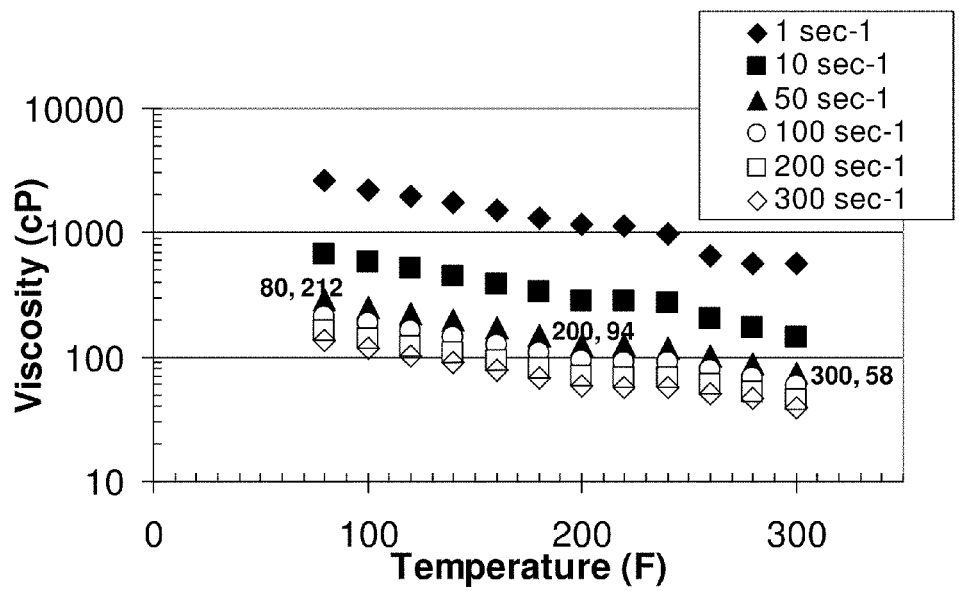
FIG. 6 shows a plot of data of comparative Example 3 for data from a test of a mixture of 3 wt. % HASE polymer A at a pH 12 with 2 wt. % KCl with the crosslinker ethylene glycol dimethacrylate (EGDM).

FIG. 6 shows data from a test of a mixture of 3 wt. % HASE polymer G at a pH 12 with 2 wt. % KCl and the crosslinker ethylene glycol dimethacrylate (EGDM). This shows HASE polymer G can achieve a viscosity of 50 cp at 220-230° F.

Example 4

Overall Charge Effect

Figure 7:
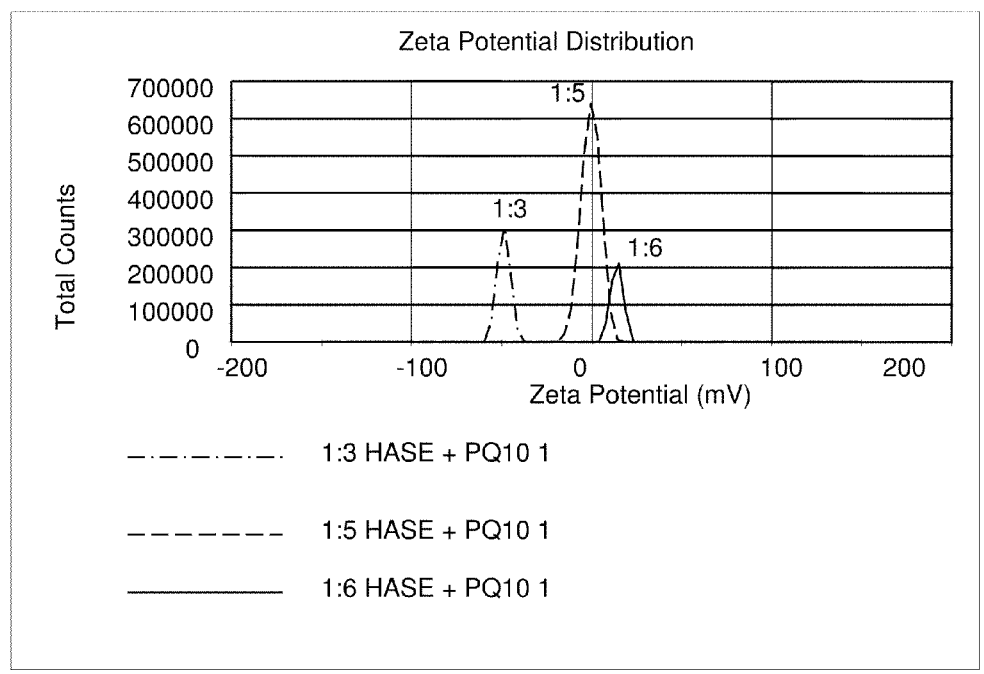
FIG. 7 shows overall charge of 4% HASE solution of Example 4.

These HASE polymers were mixed with different concentration of polycationic compound, such as polyquarternium (PQ) 10 and cationic guar and tested for their high temperature behavior. The main reason for this addition was that HASE polymer was an anionic polymer in which the overall charge of the polymer was negative. This negative overall charge would be susceptible to significant viscosity decrease in high brine condition. Polycationic was used to mask this overall negative charge. FIG. 7 shows the overall charge of the samples when they were tested using MALVERN ZETASIZER.

FIG. 7 showed the overall charge of the solution when the weight ratio between HASE and PQ 10 was 1 to 3 was −50 mV. At 1 to 5 weight ratio, the solution's potential was close to 0. At 1 to 6, the solution's potential was found to be +14 mV. Solutions of HASE and PQ10 with these weight ratios were made and tested for their viscosity behavior. Making 1 to 6 ratio of HASE and PQ 10 was not practical because the difference in the amount added to make this solution was too close to those added to make 1 to 5 weight ratio. Therefore, a 1 to 7 weight ratio solution was tested instead. FIG. 8B displayed the resulting viscosity of these and other samples.

Figure 8:
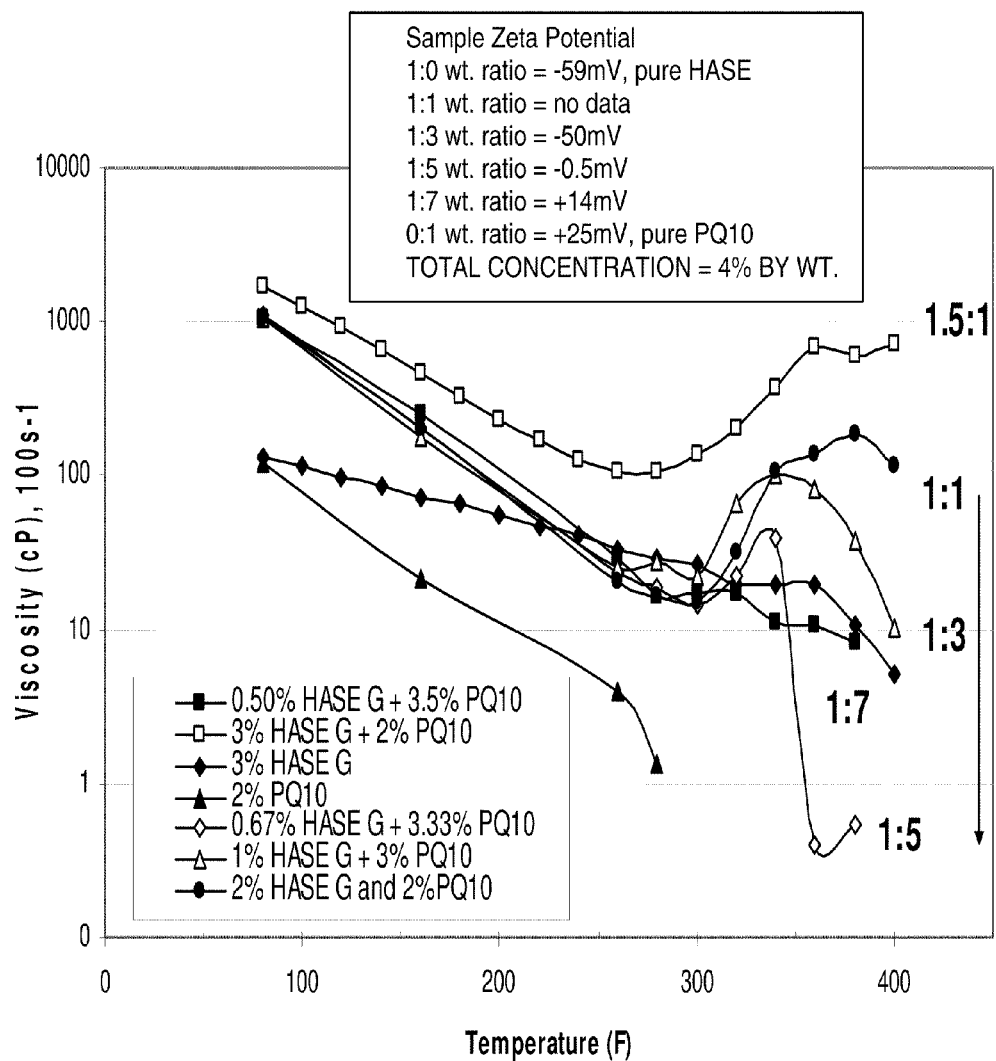
FIG. 8 shows a plot of data of Example 4 for the effect of different overall charge on viscosity behavior of a composition of 4 wt % active polymer level of HASE polymer G plus PQ10 (Polyquaternium-10) at 2 wt. % KCl.

FIG. 8 shows the effect of different overall charge on viscosity behavior of a composition of 4 wt % active polymer level of HASE Polymer G plus PQ-10 (Polyquaternium-10) at 2 wt. % KCl. The overall charge was positive or negative, but not zero. PQ-10 is cationic hydroxyethyl cellulose. PQ-10 is a polymeric quaternary ammonium salt of hydroxyethyl cellulose reacted with a trimethyl ammonium substituted epoxide. Another name for it is cellulose, 2-[2-Hydroxy-3-Trimethylammono)propoxy]ethyl ether, chloride.

FIG. 8 also shows viscosity profiles of HASE G and PQ10 at varying mass ratios from the prior example plus additional samples. A surprising rise in viscosity at temps >300° F. was observed. The immediate explanation can be crosslinking as found of the consistency of the product shown in FIG. 8.

The 1:3 sample with 4% active polymer (HASE G+PQ10) produced a better viscosity than the 1:5 and 1:7 samples with 4% active polymer above 300° F. Below 300° F., the viscosity for these three solutions was almost identical.

The 1:1 sample with 4% active polymer had improved performance above 300° F. The 1:5 sample with 5% active polymer had improved performance above 300° F.

Example 5

2% HASE Polymer with Polycationic in 2% KCl

Figure 9:
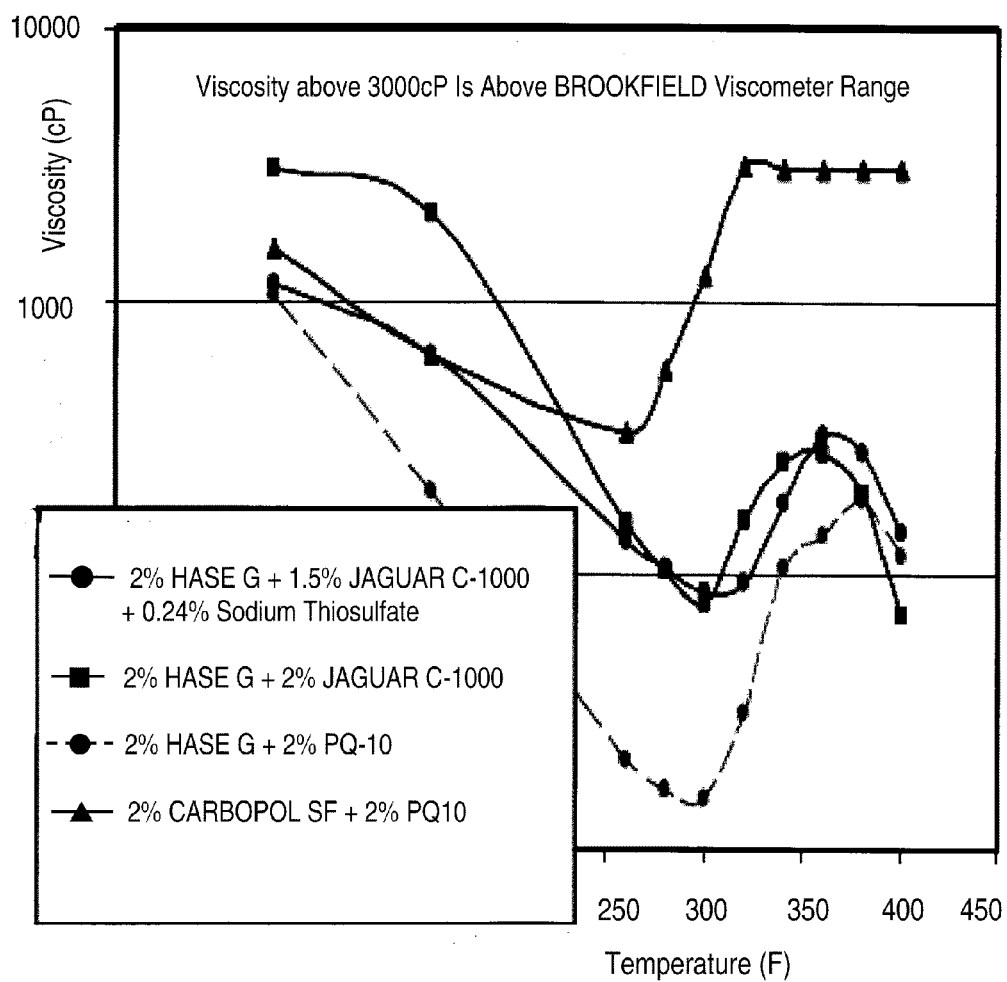
FIG. 9 shows a plot of data of Example 5 for viscosity profiles of various HASE and polycationics.

FIG. 9 shows viscosity profiles of HASE polymer G and various polycationics.

The viscosity exhibited by 2% CARBOPOL SF+2% PQ10 exceeded the Brookfield limit at temperature above 320° F. Comparing the result for 2% HASE G+2% JAGUAR C-1000 and 2% HASE G+1.5% JAGUAR C-1000+0.24% sodium thiosulfate revealed reducing the cationic guar concentration seemed to reduce the overall viscosity at temperature from 80° F. to 280° F. The dip in the curve depended on the concentration of HASE used. The increase in viscosity at temperature above 300° F. depended on the presence of cationic guar or any polycationic. If there was polycationic present, it seemed there was still increase in viscosity. Sodium thiosulfate played a role in delaying the increase in viscosity at higher temperature. Without sodium thiosulfate, viscosity increase started at 300° F., but for the solution with thiosulfate viscosity increase occurred at 320° F.

The rises in viscosity at extreme temperatures were apparently true with various HASE and other methacrylate/acrylate containing copolymers, in combination with various (if not all) polycationics. This shows tolerance at high temperatures for these fluids. This is useful for deep oil and gas wells and off shore oil and gas wells where temperatures are very high.

Example 6

HASE Polymer in 2% KCl

Figure 10:
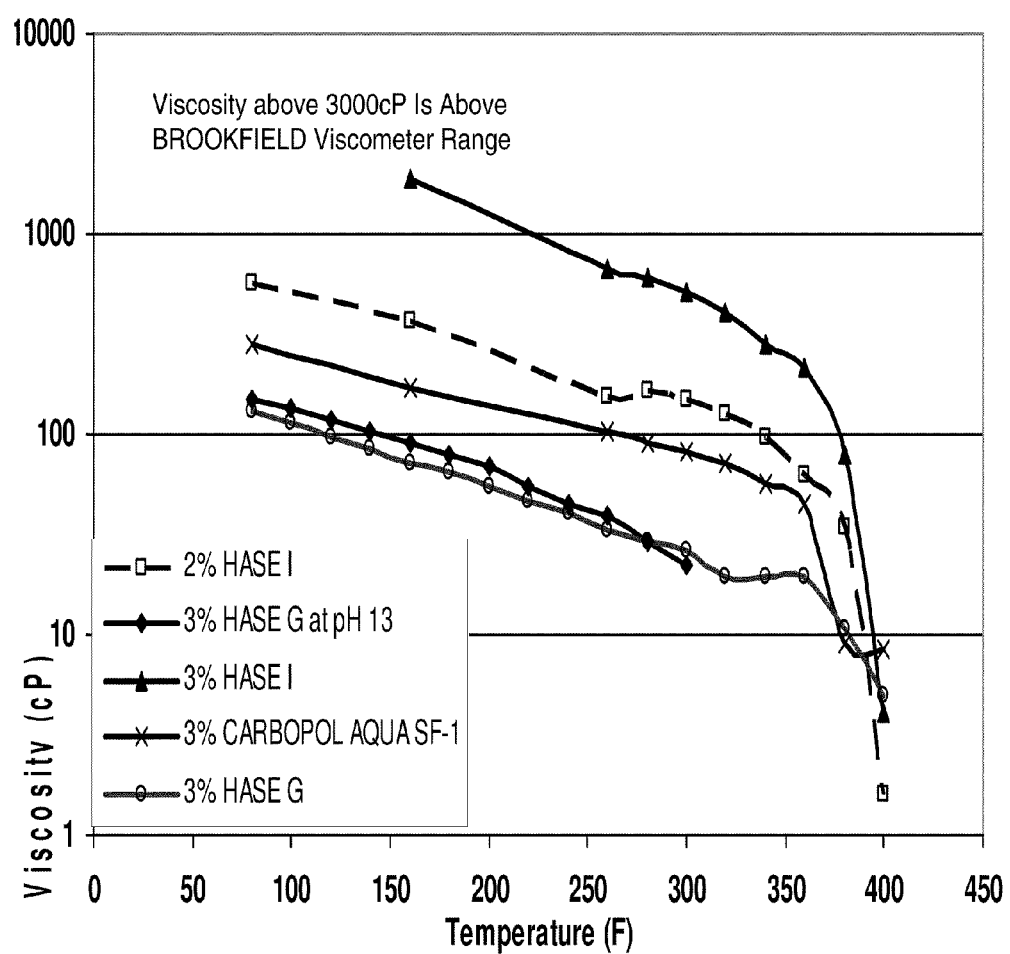
FIG. 10 shows a plot of data of Example 6 for viscosity profiles of a number of HASE compositions compared to CARBOPOL.

FIG. 10 shows viscosity profiles of a number of HASE compositions compared to CARBOPOL AQUA SF-1 Alkali-Swellable acrylic Emulsion (ASE) polymer. The composition of 3% HASE polymer I with 8.3% alkyl and 1.7% Nopol has the best viscosity profile.

Figure 11:
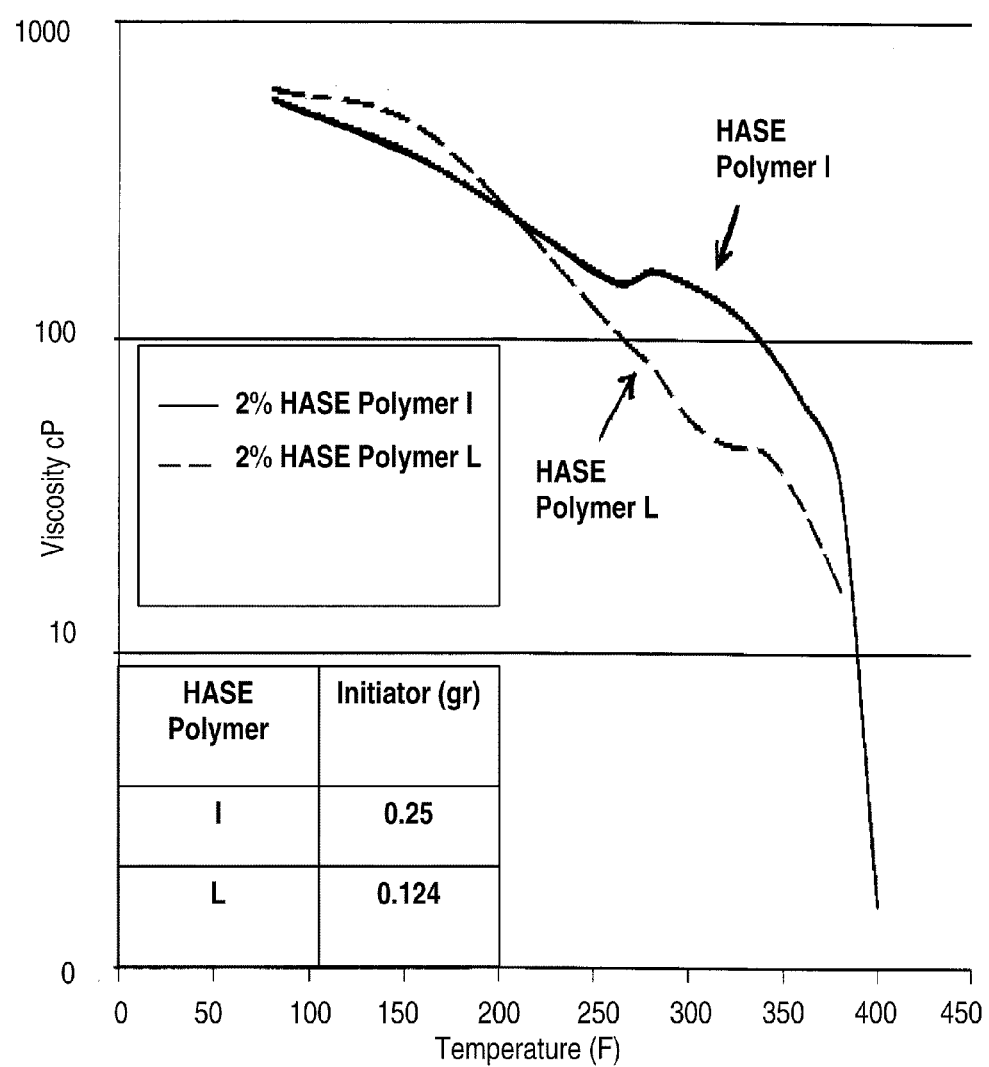
FIG. 11 shows a plot of data of Example 6 comparing HASE polymers I and L both having 8.3% alkyl and 1.7% Nopol but different molecular weights.

FIG. 11 compares HASE polymers I and L both having 8.3% alkyl and 1.7% Nopol, but having different molecular weights. The amount of initiator used in the polymerization reaction to make the HASE polymer I was 0.25 grams. For HASE polymer L the amount of initiator was 0.124 grams. HASE polymer L had a higher molecular weight than HASE polymer I because HASE polymer L used less initiator. The performance at low temperature indicated that HASE polymer L produced a better viscosity. However, at high temperature, HASE polymer L fell more rapidly than lower molecular weight HASE polymer I.

Example 7

2% HASE in 2% KCl

Figure 12:
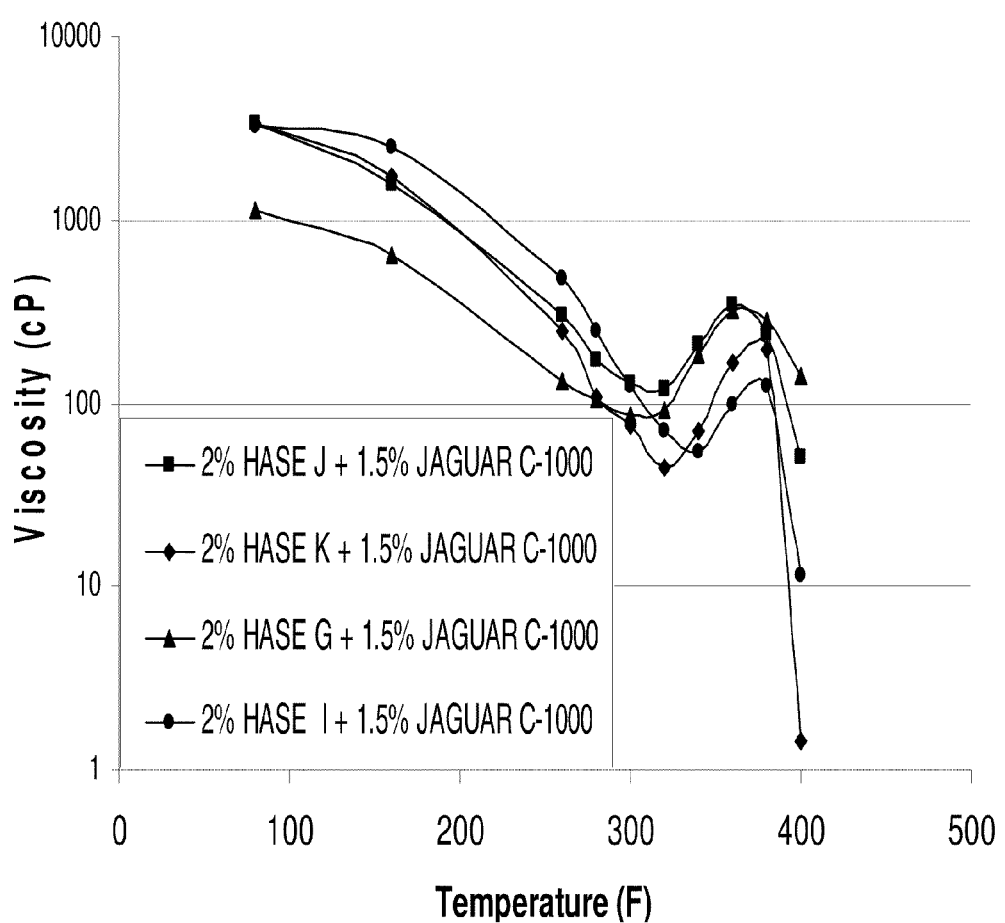
FIG. 12 shows a plot of data of Example 7 for the effect of different ratios of Macro Monomer I and Macro Monomer II towards viscosity behavior in a blend with a cationic polymer.

FIG. 12 shows the effect of different ratios of Macro monomer I and Macro monomer II towards viscosity behavior in a blend with JAGUAR C-1000 cationic polymer. TABLE 10 lists the different ratios of Macro monomer I and Macro monomer II

TABLE 10

| HASE | phm (parts per hundred monomer) in HASE Polymer | |
| --- | --- | --- |
| | Macro monomer I | Macro monomer II |
| G | 4 | 0 |
| I | 1.67 | 8.33 |
| J | 2 | 2 |
| K | 5 | 5 |

HASE polymers G and J had a better bump at higher temperature compared to the other HASE polymers. This meant that Macro monomer I facilitated this interesting high temperature behavior better than Macro monomer II. However, Macro Monomer II provided a better viscosity than Macro Monomer I at low temperature. In addition, the bump at high temperature was favored when the concentration of both Macro monomer I and Macro Monomer II was low.

Example 8

Figure 13:
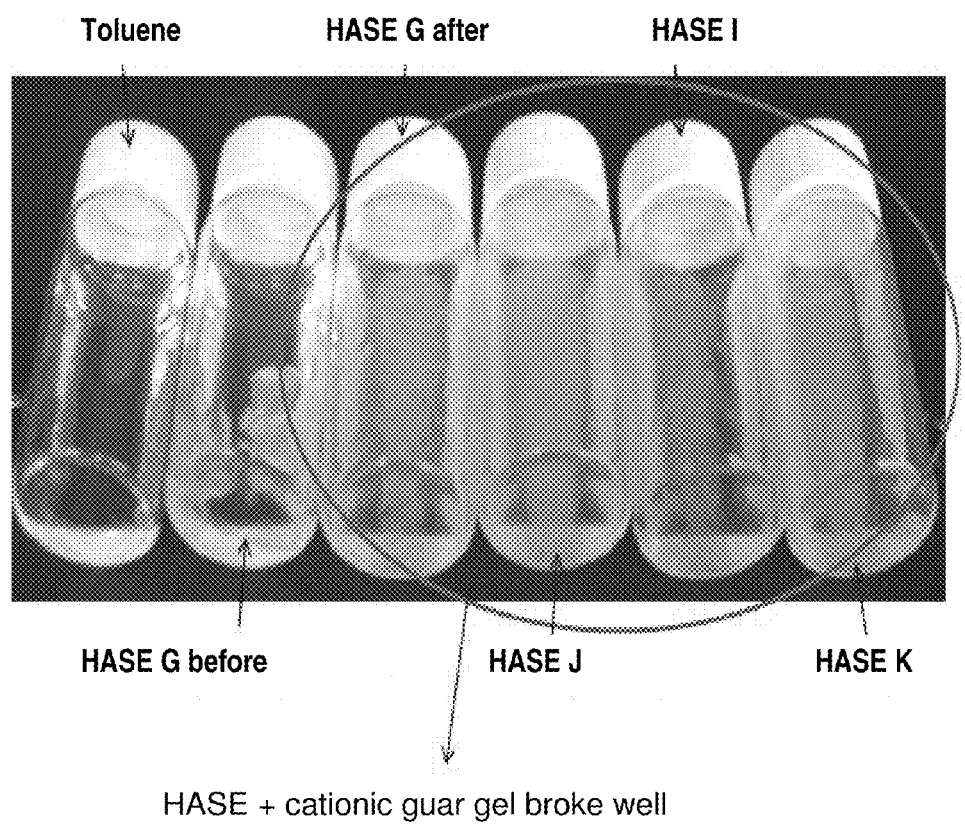
FIG. 13 shows bottles of Example 8 containing mixtures of different HASE polymers with cationic guar solution of Example 11.

To test the solubility in toluene of mixtures of different HASE polymers with cationic guar solution the HASE polymer and JAGUAR C-1000 cationic guar solutions of Example 7, after the test of Example 7, were mixed with toluene to determine how well the gel would break. After undergoing the high temperature Brookfield viscometer test, a portion of each of the test samples of Example 7 was mixed with toluene to see how the solution or gel behaved. FIG. 13 shows bottles containing these mixtures of different HASE polymers with cationic guar solution of Example 7. From left to right in FIG. 14:

Control (toluene)
2% HASE G+1.5% JAGUAR C-1000 before test
2% HASE G+1.5% JAGUAR C-1000 after test
2% HASE J+1.5% JAGUAR C-1000 after test
2% HASE I+1.5% JAGUAR C-1000 after test
2% HASE K+1.5% JAGUAR C-1000 after test As shown by FIG. 13, all the HASE+cationic guar solution/gel broke nicely. There was little difference in the breaking performance between HASE polymer containing more Macro Monomer I or HASE polymer containing more Macro Monomer II.

Example 9

Polyanionic and Polycationic in 2% KCl

Behavior of several polycationic and cationic guar was compared. The result showed the increase in viscosity did not only happen for HASE polymer only but also for these other polyanionic such as CARBOPOL AQUA SF-1 Alkali-Swellable acrylic Emulsion (ASE) polymer, polyacrylamide, polyacrylic acid and RHODIA copolymer AM/AA/AMPS (acrylamidomethylpropane sulfonic and acrylamide copolymer). These polymers contained acrylic acid (or methacrylic acid as in HASE) or produced acrylic acid upon hydrolysis at high temperature.

Figure 14:
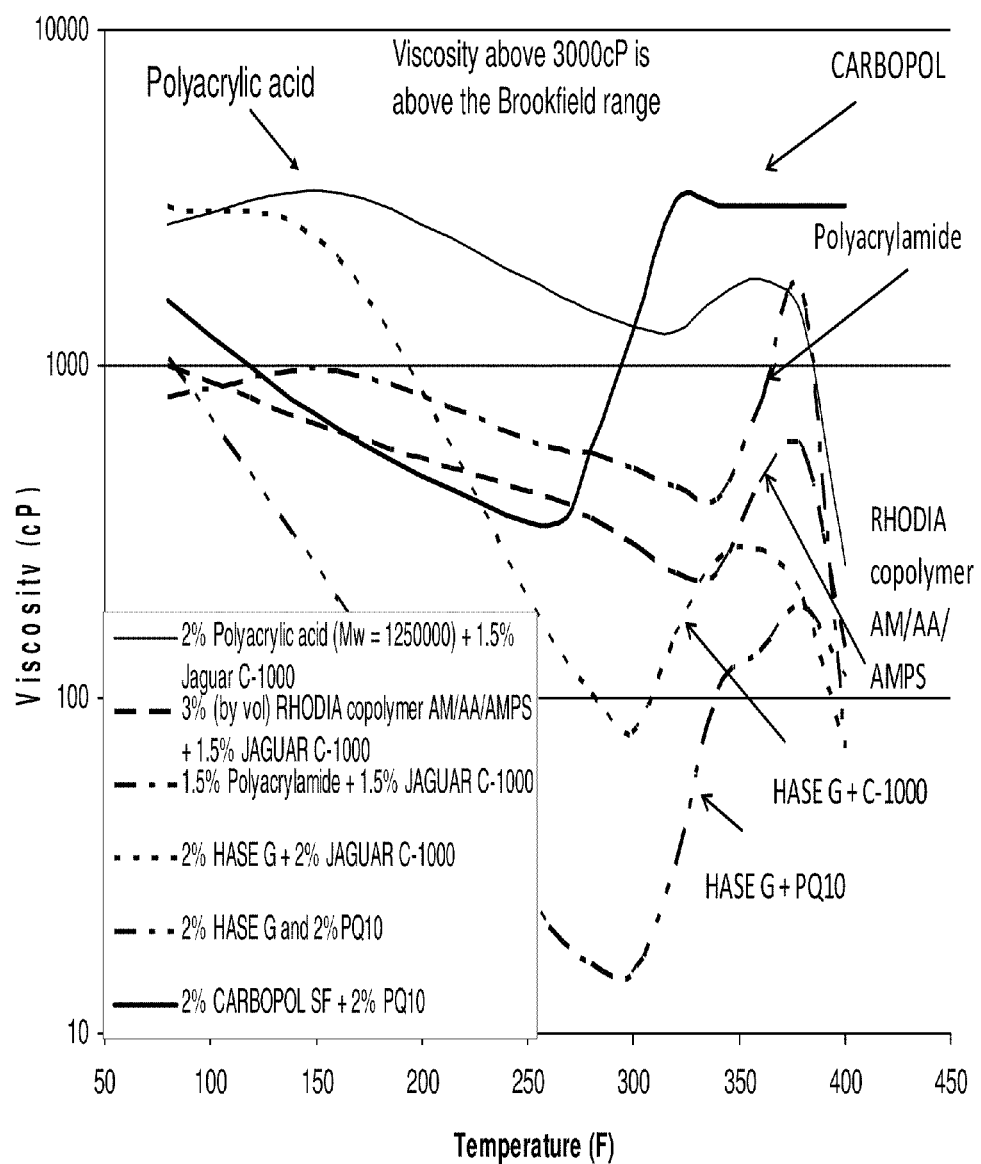
FIG. 14 shows the effect of different anionic polymers with cationic guar or PQ10 of Example 9.

FIG. 14 shows the effect of different anionic polymers with cationic guar or PQ10.

Example 10

The solubility in toluene of mixtures of different anionic HASE polymers with cationic guar solution of Example 9 was tested. The anionic HASE polymer and cationic guar or PQ10 solution after the test of Example 9 were mixed with toluene to determine how well the gel would break. This was also compared with visco elastic surfactant.

Figure 15:
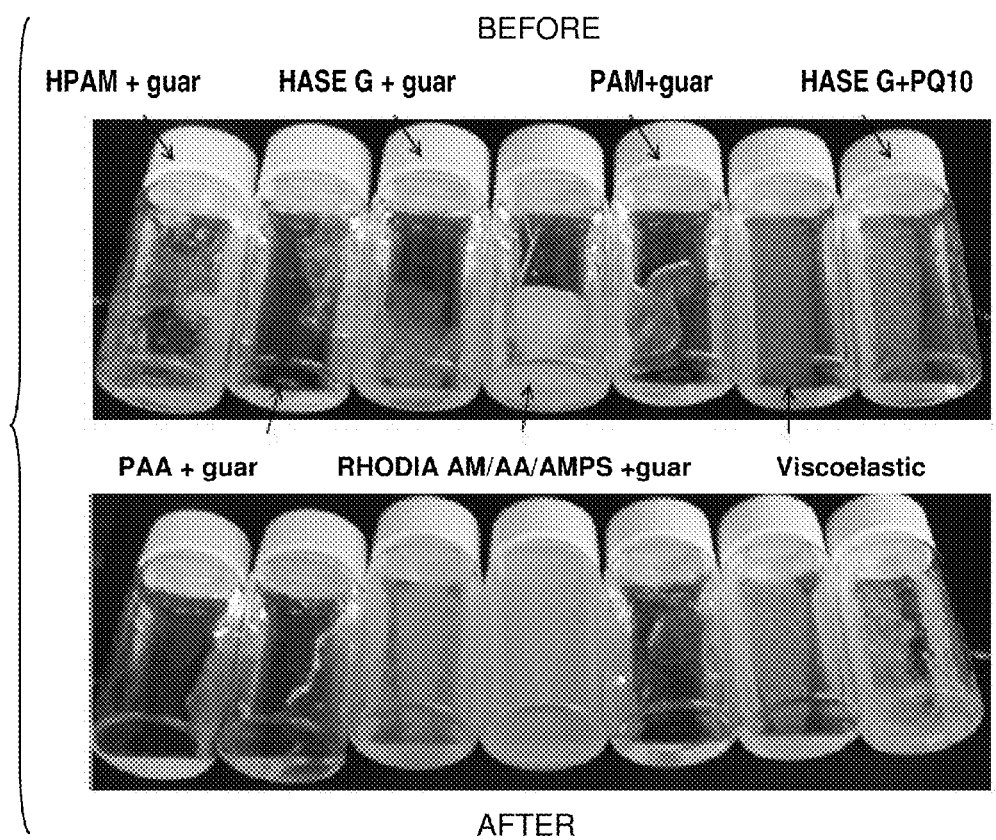
FIG. 15 shows bottles of Example 10 containing mixtures of different HASE polymers with cationic guar solution of Example 9 in toluene.

FIG. 15 shows the BEFORE and AFTER photographs of these samples. From left to right the contents of the samples are as follows:

1.5% Hydrolyzed PAM (polyacrylamide)+1.5% JAGUAR C-1000 cationic guar gum

2% PAA (polyacrylic acid)+1.5% JAGUAR C-1000 cationic guar gum

2% HASE polymer G+1.5% JAGUAR C-1000 cationic guar gum

3% (by vol.) copolymer AM/AA/AMPS+1.5% JAGUAR C-1000 cationic guar gum 1.5% PAM+1.5% JAGUAR C-1000 cationic guar gum visco elastic surfactant 2% anionic HASE polymer G+2% cationic PQ-10 (Polyquaternium 10)

As shown by FIG. 15, the polyacrylic acid (PAA)+cationic guar, hydrolyzed polyacrylamide (HPAM)+cationic guar and polyacrylamide (PAM)+cationic guar did not break in toluene. However, the gel for RHODIA copolymer AM/AA/AMPS surfactant+cationic guar broke nicely despite being cloudy because some of the mixture stayed in the wall of the glass. For anionic HASE polymer+cationic guar, the gel broke as well as visco elastic surfactant. The gel of anionic HASE polymer+cationic PQ-10 broke before and after the test.

The anionic HASE polymer with cationic guar broke as well as visco elastic surfactant.

Example 11

Figure 16:
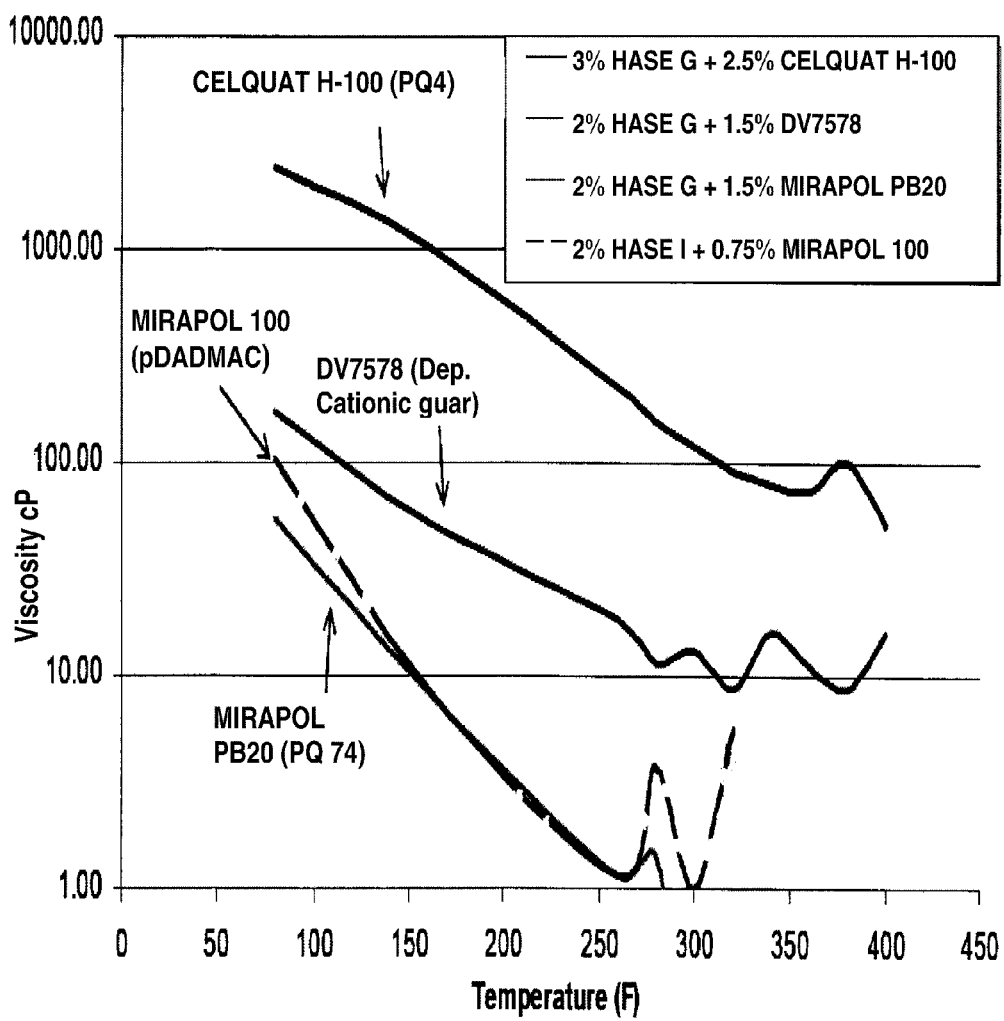
FIG. 16 shows the effect of different cationic polymers with HASE polymer in 2 wt. % KCl for Example 11.

This example shows the effect of different cationic polymers with anionic HASE polymer in 2 wt. % KCl. The results are shown in FIG. 16. MIRAPOL PB20 (PQ-74) and MIRAPOL 100 (polyDADMAC) did not produce any noticeable viscosity increase at high temperature. PQ-74 is a cationic polymer. PQ-74 is a term of art according to the CTFA International Cosmetic Ingredient Dictionary. Polydiallyldimethylammonium chloride, or shortened polyDADMAC, is a homopolymer of diallyldimethylammonium chloride (DADMAC). The molecular weight of polyDADMAC is typically in the range of hundreds of thousands of grams per mole, and even up to a million for some products. In addition, the initial viscosity of these solutions was relatively low compared to those combinations that worked. DV7578 was a depolymerized cationic guar and the result did not show any significant increase at high temperature. However, at high temperature, the viscosity was quite linear around 9 to 11 cPs. This could be attributed to the interaction between the cationic guar and anionic HASE polymer. The absence of viscosity increase might be caused by the short chain length of this DV7578 depolymerized cationic guar.

The best working combination contained CELQUAT Polyquaternium-4 cationic polymer (PQ-4) available from Akzo Nobel. PQ-4 is a copolymer of hydroxyethylcellulose and diallyldimethyl ammonium chloride. The results for CELQUAT H-100 (PQ-4) showed it maintained the highest viscosity but produced only a small viscosity increase at very high temperature.

Example 12

2% HASE+Cationic in 2% KCl

This example compares the effect of mono-substituted versus di-substituted cationic polymers with HASE polymer in 2 wt. % KCl. It does this by comparing the results for 3% anionic HASE polymer G+CELQUAT H-100 (PQ-4) from Example 11 with the results for 2% anionic HASE polymer G+2% JAGUAR C-1000 cationic guar, and 2% anionic HASE polymer G+2% cationic PQ-10 from Example 9.

PQ-10 have a representative structural formula A.XXXIV

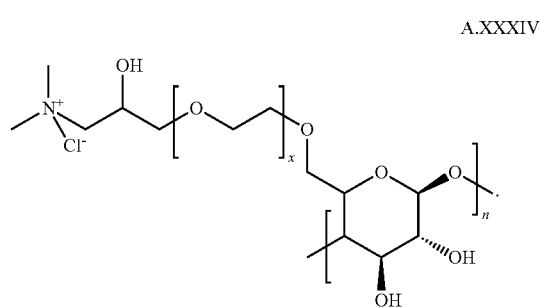

JAGUAR C-1000 cationic guar having a representative structural formula A.XXXV:

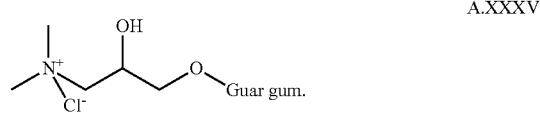

CELQUAT H-1—having a representative structural formula A.XXXVI:

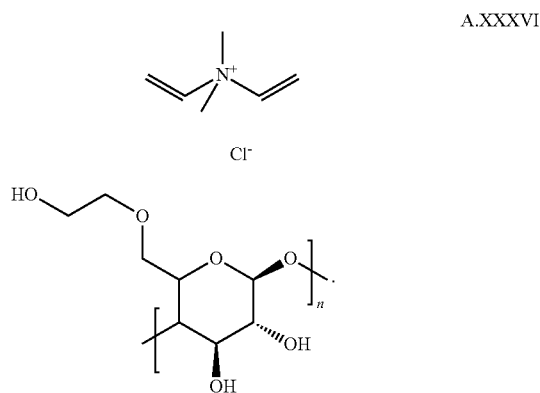

Figure 17:
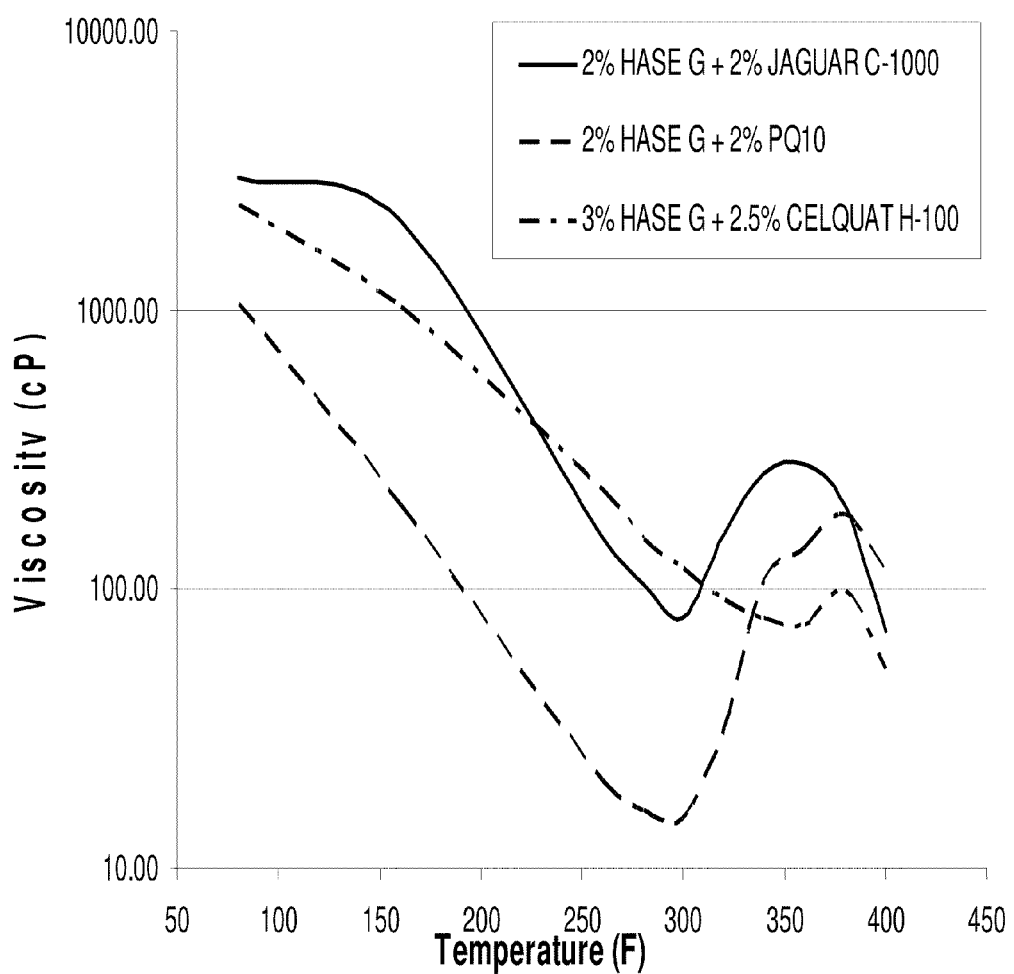
FIG. 17 compares the effect of mono-substituted versus di-substituted cationic polymers with HASE polymer in 2 wt. % KCl for Example 12.

The results are shown in FIG. 17. The mono-substituted cationic polymer such as in PQ-10 and cationic guar provided a bigger bump in viscosity at high temperature than the di-substituted cationic polymer CELQUAT H-100 (PQ-4). The results for CELQUAT H-100 (PQ-4) showed it produced only a small viscosity increase at very high temperature. This implies the polycationic should preferably be monosubstituted quaternary amine such as in PQ-10 and cationic guar. Disubstituted quaternary amine may have generated some hindrance toward intermolecular interaction, which prevented the viscosity increase at very high temperature.

Example 13

Comparative Example

Figure 18:
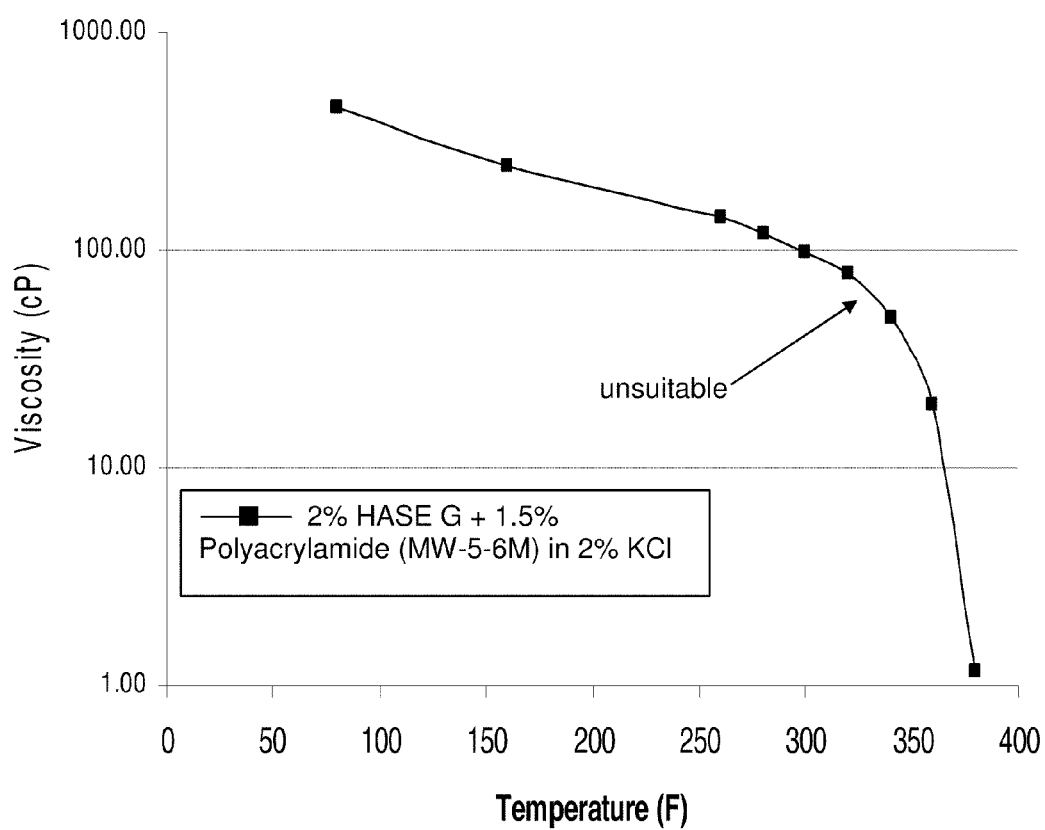
FIG. 18 shows results of a viscosity test of a mixture of two anionic polymers, for Example 12, the mixture containing 2% HASE polymer G and 1.5 wt % polyacrylamide in 2 wt. % KCl.

For comparison purposes a mixture of two anionic polymers was tested. In particular a mixture containing 2% HASE polymer G and 1.5 wt % polyacrylamide in 2 wt. % KCl was tested by a viscosity test. It was found unsuitable as indicated by FIG. 18.

Example 14

Comparative Example—Viscous Polymer in 2% KCl

Figure 19:
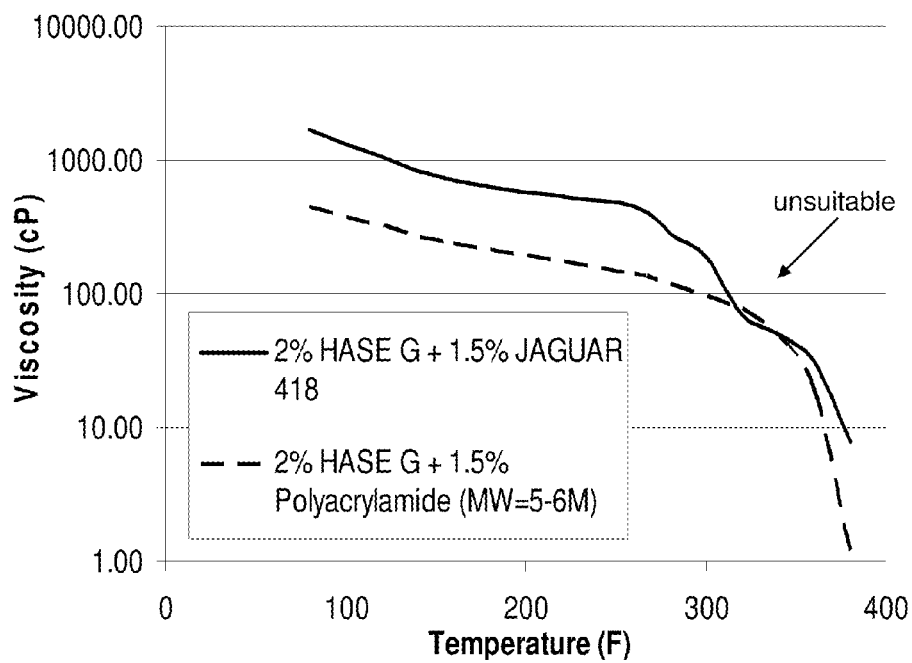
FIG. 19 shows results of a viscosity test of a mixture of a synthetic polymer and a cellulosic based polymer (both anionic polymers) for comparative Example 14, the mixture containing 2% HASE polymer G and 1.5 wt % JAGUAR 418 (CMHPG) in 2 wt. % KCl.

For comparison purposes a mixture of a synthetic anionic polymer and a cellulosic based anionic polymer was tested. In particular a viscosity test was conducted on a mixture containing 2% HASE G polymer and 1.5 wt % JAGUAR 418 (CMHPG, carboxymethylhydroxypropyl guar) in 2 wt. % KCl. It was found unsuitable as indicated by FIG. 19.

Example 15

2% HASE+1.5% JAGUAR C-1000 in 2% KCl

Figure 20:
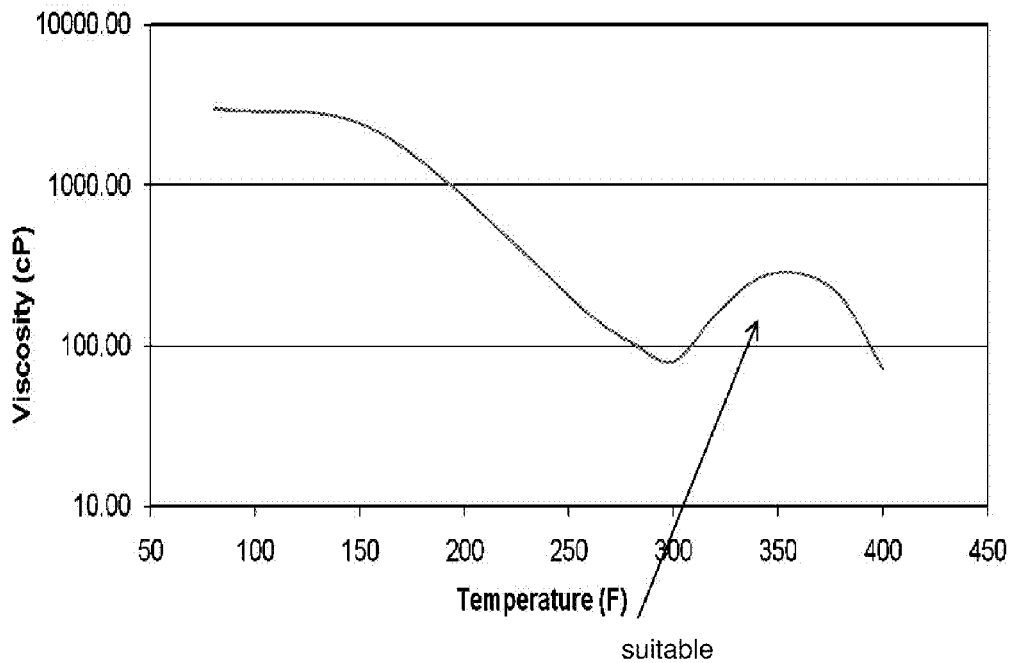
FIG. 20 shows viscosity test results for a combination of 2 viscous solutions with opposite charges, namely 2 wt. % HASE anionic polymer and 1.5 wt.% JAGUAR C-1000 (cationic guar hydroxypropyl trimonium chloride) in 2 wt % KCl solution for Example 15.

In contrast to the comparative examples, a combination of 2 viscous solutions with opposite charges, namely 2 wt. % HASE anionic polymer and 1.5 wt. % JAGUAR C-1000 (cationic guar hydroxypropyl trimonium chloride) in 2 wt % KCl solution was tested and found suitable as shown by FIG. 20.

Example 16

Polyacrylamide vs. Polyacrylic Acid with JAGUAR C-1000

This example compared combinations of 2 viscous solutions with opposite charges to compare the effect of different anionic polymers with JAGUAR C-1000 (cationic guar hydroxypropyl trimonium chloride) in 2 wt % KCl solution. In particular the following mixtures were compared:
1.5 wt. % hydrolyzed polyacrylamide and 1.5 wt. % JAGUAR C-1000
1.5 wt. % polyacrylamide and 1.5 wt. % JAGUAR C-1000, and
2 wt. % polyacrylic acid and 1.5 wt. % JAGUAR C-1000.

Figure 21:
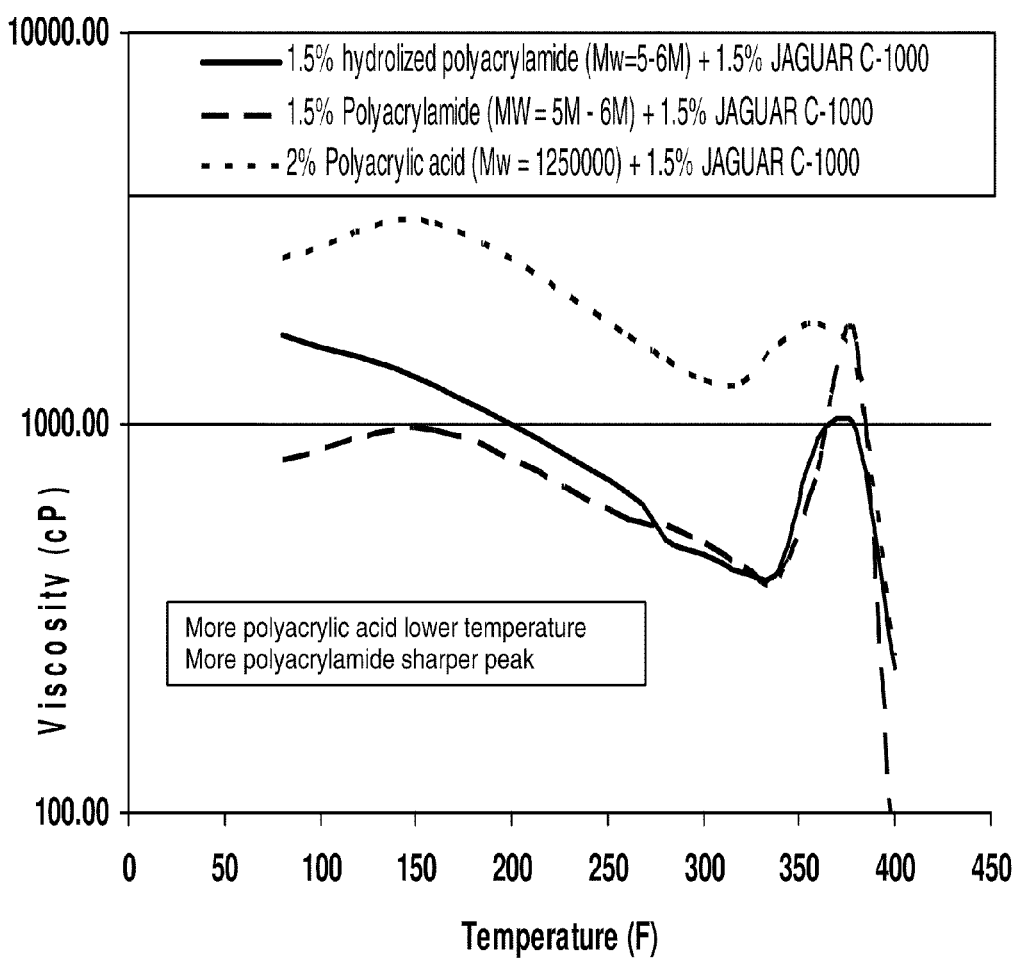
FIG. 21 shows a comparison of combinations of 2 viscous solutions with opposite charges to compare the effect of different anionic polymers with JAGUAR C-1000 (cationic guar hydroxypropyl trimonium chloride) in 2 wt % KCl solution for Example 16

The results are shown in FIG. 21. FIG. 21 shows polyacrylic acid, polyacrylamide and hydrolyzed polyacrylamide exhibited a viscosity increase at high temperature. Since hydrolyzation of acrylamide would produce acrylic acid, this hydrolyzed polyacryamide could be considered as a copolymer of acrylic acid and acrylamide. These three polymers had different ratios of acrylic acid (AA) and acrylamide (AM).

FIG. 21 also shows the relation of AA and AM toward the increase in viscosity. FIG. 21 shows the mixture containing anionic polyacrylic acid had a more constant viscosity but the mixtures containing polyacrylamide had a sharper viscosity peak. The higher the AA/AM ratio, the lower the temperature in which the viscosity started to increase. The lower the AA/AM ratio, the higher the high temperature peak. Thus, if a higher peak at high temperature is desired then a lower AA/AM ratio may be advantageous.

Example 17

Gel Stability of Mixtures—Polyanionic+1.5% JAGUAR C-1000 on 2% KCl at 375 F

In this example a high temperature stability test was conducted at 375° F. to compare combinations of 2 viscous solutions with opposite charges to compare the effect of different anionic polymers with JAGUAR C-1000 in 2 wt % KCl solution. TABLE 11 shows the compositions of the tested samples and the results of testing these combinations of polymers for their stability at 375° F. Stability time indicated how long the solution could maintain a suitable viscosity at 375° F. Delay time indicated the time required for the mixture's viscosity to increase after it reached its lowest viscosity.

TABLE 11

Delay time and stability time for the polyanionic and polycationic at 375° F.

| Polyanionic | Polycationic | Delay | Stability | Viscosity Max. (cP) |
|---|---|---|---|---|
| 3% (by vol) RHODIA copolymer AM/AA/AMPS | 1.5% JAGUAR C-1000 cationic guar | 5 | 60 | 400 |
| 1.5 wt. % Polyacrylamide | 1.5% JAGUAR C-1000 cationic guar | 7 | 100 | 2000 |
| 2 wt. % Polyacrylic acid | 1.5% JAGUAR C-1000 cationic guar | 2 | 210 | 1650 |
| 1.5 wt. % Hydrolyzed polyacrylamide | 1.5% JAGUAR C-1000 cationic guar | 5 | 60 | 1350 |
| 2 wt. % HASE polymer G | 1.5% JAGUAR C-1000 cationic guar | 3 | 40 | 60 |
| 2 wt. % HASE polymer G | 1.5% POLYCARE 400 (PQ-10) | 15 | 110* | 350 |

*The combination did not produce a stable system during the test

Anionic HASE polymer G and cationic guar did not produce a high maximum viscosity, only 60 cPs. Furthermore, anionic HASE polymer G and PQ-10 cationic polymer produced a mixture that had a low shear recovery rate indicated by the fluctuation in viscosity after a shear rate ramp was performed. The longer the delay time, the worse the performance of the mixture would be because the viscosity would decrease below the desired limit of 50 cP.

Figure 22:
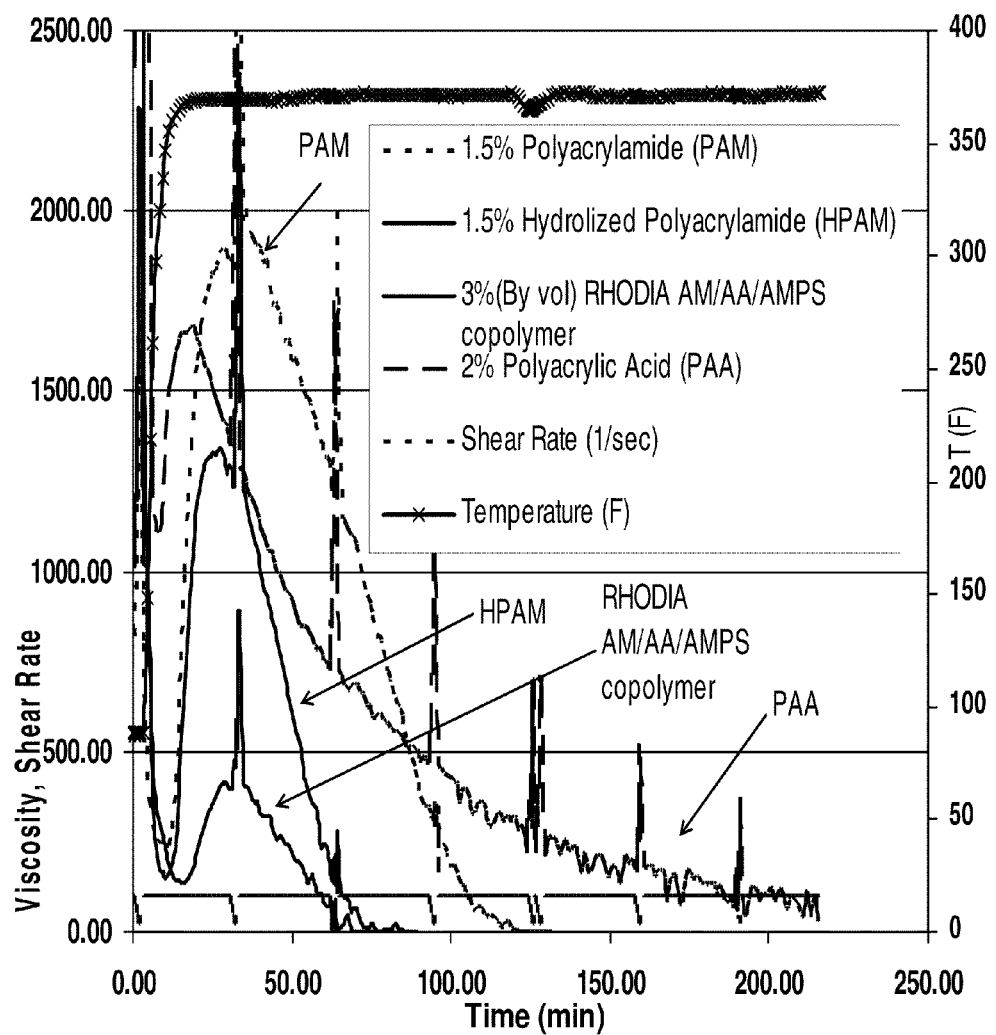
FIG. 22 shows the results of a high temperature stability test conducted at 375° F. to compare combinations of 2 viscous solutions with opposite charges to compare the effect of different anionic polymers with JAGUAR C-1000 in 2 wt % KCl solution for Example 17.

FIG. 22 plots the stability data for a number of the samples listed in TABLE 11. It shows the mixture containing polyacrylamide had a higher maximum viscosity and was more stable.

Example 18

2% HASE G+POLYCARE 400 (PQ10) in 2% KCl at 375° F.

Figure 23:
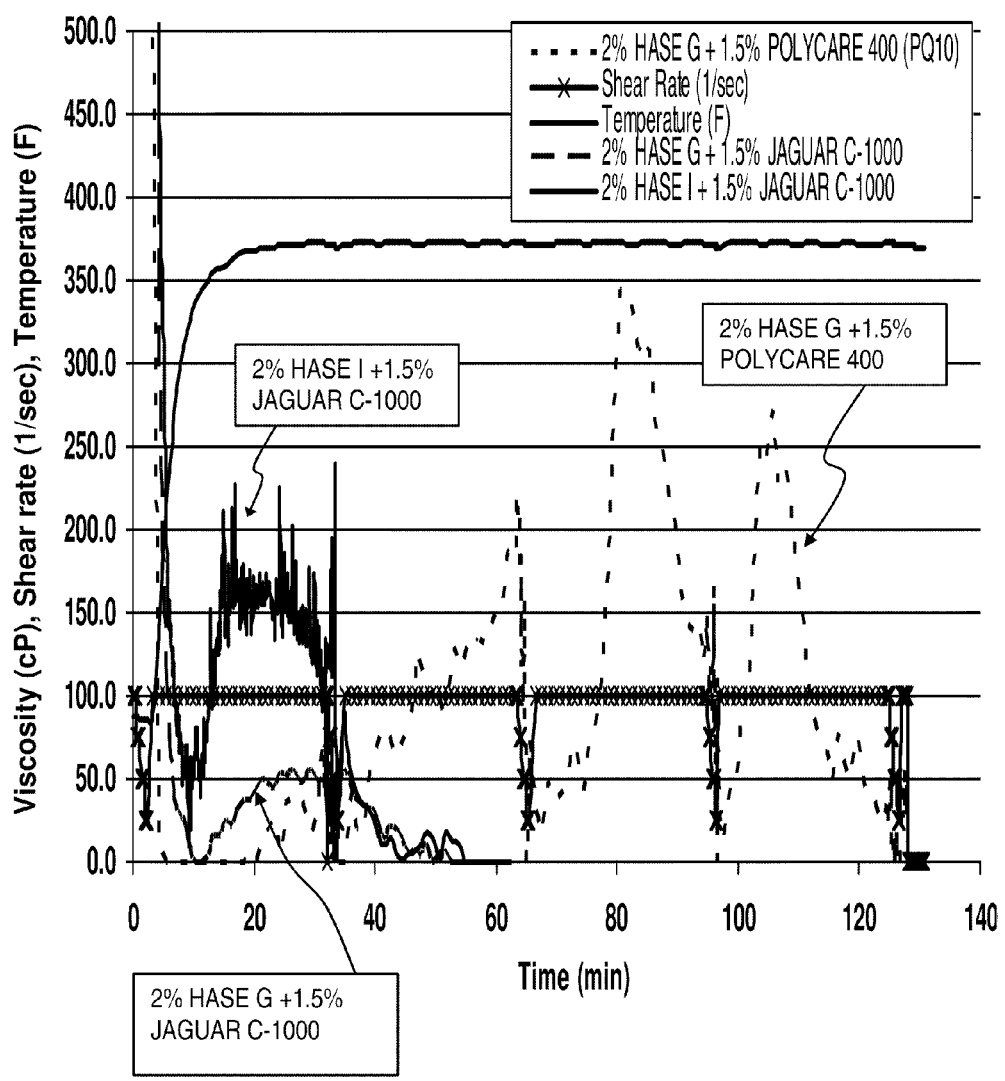
FIG. 23 shows the results of a high temperature stability test conducted at 375° F. to compare combinations of 2 viscous solutions with opposite charges to compare the effect of different HASE anionic polymers with JAGUAR C-1000 or POLYCARE 400 (PQ 10) in 2 wt % KCl solution for Example 18.

In this example a high temperature stability test was conducted at 375° F. to compare combinations of 2 viscous solutions with opposite charges to compare the effect of different anionic HASE polymers with JAGUAR C-1000 cationic guar or POLYCARE 400 (PQ 10) cationic polymer in 2 wt % KCl solution. In particular the following mixtures were compared:
2 wt. % HASE polymer G and 1.5 wt. % cationic JAGUAR C-1000,
2 wt. % HASE polymer 1 and 1.5 wt. % cationic JAGUAR C-1000, and 2 wt. % HASE polymer G and 1.5 wt. % POLYCARE 400 (PQ 10) cationic polymer. FIG. 23 shows the mixture containing HASE polymer I+cationic guar and the mixture containing HASE polymer G+cationic guar had relatively lower stability. FIG. 23 also shows the mixture of HASE anionic polymer G and PQ-10 cationic polymer had relatively lower shear recovery.

Example 19

2% HASE G+1.5% JAGUAR C-1000 in 2% KCL at 375° F.

Figure 24:
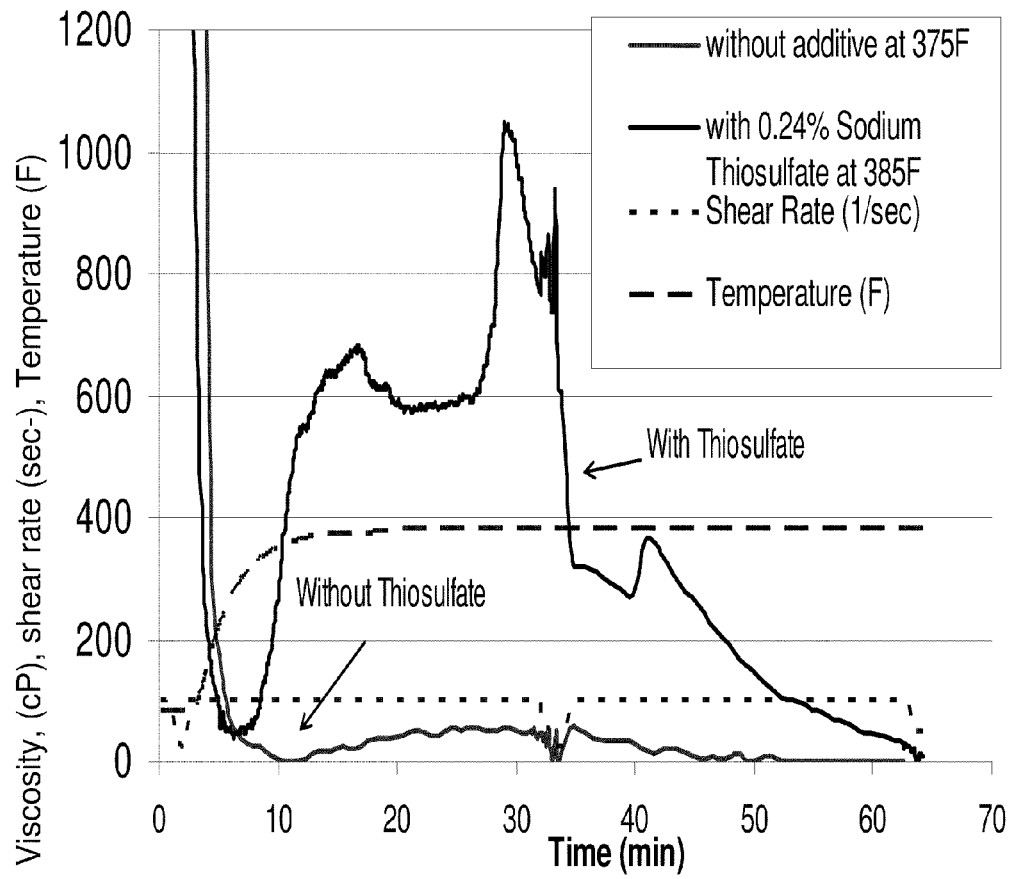
FIG. 24 shows the results of a high temperature stability test conducted at 375° F. to compare combinations of 2 viscous solutions with opposite charges to compare the effect of different HASE anionic polymers with JAGUAR C-1000 or POLYCARE 400 (PQ 10) in 2 wt % KCl solution for Example 19.

In this example the effect on stability of adding 0.24 wt. % sodium thiosulfate was tested. Sodium thiosulfate is an oxygen scavenger. In particular a mixture of 0.24 wt. % sodium thiosulfate, 2 wt. % anionic HASE polymer G and 1.5 wt. % JAGUAR C-1000 cationic guar was subjected to a viscosity test and compared to the same mixture without the sodium thiosulfate. FIG. 24 shows the results. As seen on FIG. 24, the thiosulfate results in a more stable guar with a better viscosity profile. Thus, adding the sodium thiosulfate preserves the natural polymer from degrading to boost the performance of the system.

It should be apparent that the present invention is not limited by the above-provided description, but rather is defined by the claims appended hereto.

What is claimed is:

1. A composition for enhancing viscosity of a fluid comprising a mixture of:
  (A) at least a first polymer having a weight average molecular weight of 35,000 to 10,000,000 selected from at least one member of the group consisting of:
    (1) cationic polysaccharides with quaternized amino functional groups and cationic charge density of 0.3 to 2 milliequivalents/gram selected from a cationically modified member of the group consisting of glucomannan gums and their derivatives, guar gum, locust bean gum, cara gum, hydroxyethyl guar, hydroxypropyl guar, cationically modified cellulose, hydroxypropyl cellulose, hydroxymethyl cellulose, and hydroxyethyl cellulose, wherein the composition has only a single cationic polysaccharide,
    (2) cationizable polymers with at least one member of the group consisting of primary, secondary and tertiary amino groups and which are at least partially cationizable to a cationic polymer having a cationic charge density of 0.3 to 2 milliequivalents/gram at a temperature of 100 to 250° C. selected from the group consisting of, acrylamide, polyvinyl alcohol, a copolymer of acrylamide, and combinations thereof;
  (B) at least a second polymer having a weight average molecular weight of 30,000 g/mol to 10,000,000 g/mol selected from at least one member of the group consisting of:
    (1) anionic polymers selected from the group consisting of polyacrylic acid, polyacrylamide and acrylate copolymer, and having an anionic charge density of 0.1 to 20 milliequivalents/gram, wherein the anionic polymer has functional groups selected from the group consisting of carboxylate, sulfate, sulfonate, phosphate or phosphonate, and
    (2) hydrolysable polymers selected from the group consisting of polyalkylacrylate, polyacrylamide and copolymers of polyalkylacrylate and polyacrylamide, the at least one hydrolysable polymer having a weight average molecular weight of 30,000 g/mol to 10,000,000 g/mol, and which is at least partially hydrolyzable to an anionic polymer having an anionic charge density of 0.1 to 20 milliequivalents/gram at a temperature of 100 to 250° C., wherein the hydrolysable polymer optionally has functional groups selected from the group consisting of sulfate, sulfonate, phosphate or phosphonate;
  wherein the composition has a zeta potential at 25° C. in the range of 0.5 to 100 mV or −0.5 to −100 mV.

2. The composition of claim 1, wherein the composition has a pH of 6 to 12 and the first polymer is selected from at least one member of the group consisting of the cationic polysaccharide with quaternized amino functional groups and cationic charge density of 0.4 to 1.7 milliequivalents/gram.

3. The composition of claim 1, wherein the first polymer comprises the cationic polysaccharide with the quaternized amino functionality selected from said cationically modified member the group consisting of guar gum, hydroxyethyl guar, hydroxypropyl guar, cellulose, hydroxypropyl cellulose, hydroxymethyl cellulose, and hydroxyethyl cellulose, wherein the composition has only a single cationic polysaccharide.

4. The composition of claim 3, wherein the anionic polymer comprises a HASE anionic polymer comprising:
  (a) one or more first monomeric units, each independently comprising at least one bicycloheptyl-polyether, bicycloheptenyl-polyether per monomeric unit, wherein the bicycloheptyl-polyether or bicycloheptenyl-polyether group may optionally be substituted on one or more ring carbon atoms by one or two ($C_1$-$C_6$)alkyl groups per carbon atom, wherein the anionic HASE polymer has 2 to 10 parts per hundred by weight of the first monomeric unit derived from a monomer of formula I:

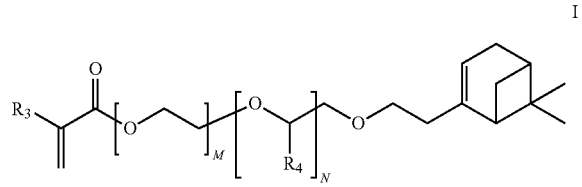

I wherein, R4 is CH3 and M and N are each 0-200, wherein, M and N are each 0-50, but M and N cannot both be 0; and 0 to 10 parts per hundred by weight a mixture of C22, C16 and C18 linear alkyl chains; and (b) optionally one or more second monomeric units, each independently comprising at least one pendant linear or branched ($C_5$-$C_{50}$)alkyl-polyether group per monomeric unit, provided that the first and second monomeric units cannot both comprise a branched ($C_5$-$C_{50}$)alkyl-polyether group;
  (c) at least one third monomeric unit selected from the group consisting of acrylic acid groups, methacrylic acid groups, and mixtures thereof and
  (d) at least one fourth monomeric unit selected from the group consisting of ethyl acrylate, butyl acrylate and ethylhexyl acrylate.

5. The composition of claim 4, wherein the cationic polysaccharide with a quaternized amino functionality is selected from the group consisting of hydroxypropyl guar and hydroxyethyl cellulose, wherein the composition has only a single cationic polysaccharide.

6. The composition of claim 5, wherein the composition has a zeta potential at 25° C. in the range of 14 to 60 mV or −0.5 to −100 mV.

7. The composition of claim 1, further comprising a monovalent salt concentration of 2 to 25 wt. % on a wet aqueous basis and/or a divalent salt concentration of 0.1 to 25 wt. % on a wet aqueous basis, wherein the composition is a first composition having no phase separation at 20° C., whereas a second composition having the same composition as the first composition but having an absence of the cationic polymer has phase separation at 20° C.

8. The composition of claim 1, further comprising a monovalent salt concentration of 2 to 25 wt. % on a wet aqueous basis and/or a divalent salt concentration of 0.1 to 25 wt. % on a wet aqueous basis, wherein the composition has a viscosity of at least 50 cp as measured by Brookfield rheometer at a temperature of 350° F. at a shear rate of 100 sec-1.

9. The composition of claim 4, wherein the composition comprises calcium chloride.

10. The composition of claim 6, wherein the HASE anionic polymer has said first, third, and fourth monomers but not said second monomer.

11. The composition of claim 10, wherein the anionic polymer contains,
wherein the third monomeric units are selected from the group consisting of acrylic acid groups, methacrylic acid groups, and mixtures thereof and the fourth monomeric units are selected from at least one member of the group consisting of ethyl acrylate, butyl acrylate and ethylhexyl acrylate.

12. The composition of claim 10, wherein the anionic polymer third monomeric units are selected from the group consisting of acrylic acid groups, methacrylic acid groups, and mixtures thereof and the fourth monomeric units are selected from at least one member of the group consisting of ethyl acrylate, and butyl acrylate.

13. The composition of claim 1, wherein at least one said anionic polymer comprises a HASE anionic polymer comprising:
(a) one or more first monomeric units, each independently comprising at least one bicycloheptyl-polyether, bicycloheptenyl-polyether or branched ($C_5$-$C_{50}$)alkyl-polyether group per monomeric unit, wherein the bicycloheptyl-polyether or bicycloheptenyl-polyether group may optionally be substituted on one or more ring carbon atoms by one or two ($C_1$-$C_6$)alkyl groups per carbon atom.

14. The composition of claim 1, wherein the anionic polymer comprises a HASE anionic polymer comprising:
(a) one or more first monomeric units, each independently comprising at least one bicycloheptyl-polyether, bicycloheptenyl-polyether or branched ($C_5$-$C_{50}$)alkyl-polyether group per monomeric unit, wherein the bicycloheptyl-polyether or bicycloheptenyl-polyether group may optionally be substituted on one or more ring carbon atoms by one or two ($C_1$-$C_6$)alkyl groups per carbon atom; and optionally
(b) one or more second monomeric units, each independently comprising at least one pendant linear or branched ($C_5$-$C_{50}$)alkyl-polyether group per monomeric unit, provided that the first and second monomeric units cannot both comprise a branched ($C_5$-$C_{50}$)alkyl-polyether group.

15. The composition of claim 14, wherein the HASE anionic polymer comprises:
(a) the one or more first monomeric units each independently comprising at least one bicycloheptyl-polyether, bicycloheptenyl-polyether per monomeric unit, wherein the bicycloheptyl-polyether or bicycloheptenyl-polyether group may optionally be substituted on one or more ring carbon atoms by one or two ($C_1$-$C_6$)alkyl groups per carbon atom, and
(b) the one or more second monomeric units, each independently comprising at least one pendant linear ($C_5$-$C_{50}$)alkyl-polyether group per monomeric unit.

16. The composition of claim 14, wherein the HASE anionic polymer comprises:
(a) the one or more first monomeric units each independently comprising at least one branched ($C_5$-$C_{50}$)alkyl-polyether group per monomeric unit, and
(b) one or more second monomeric units each independently comprising at least one pendant linear ($C_5$-$C_{50}$) alkyl-polyether group per monomeric unit.

17. The composition of claim 14, wherein the HASE anionic polymer further comprises at least one third monomeric unit independently comprising at least one acid monomeric unit, each acid monomeric unit independently comprising at least one member of the group consisting of a carboxylic acid-functional group, a sulfuric-acid functional group, a sulfonic acid-functional group, a phosphonic acid-functional group, and a phosphoric acid-functional group.

18. The composition of claim 17, wherein the HASE anionic polymer further comprises at least one fourth monomeric unit independently comprising at least one member of the group consisting of an alkyl group, hydroxyalkyl group, alkoxyalkyl group, cycloalkyl group, aryl group, aralkyl group, or aryloxy group.

19. The composition of claim 18, wherein the third monomeric units are selected from the group consisting of acrylic acid groups, methacrylic acid groups, and mixtures thereof and the fourth monomeric units are selected from at least one member of the group consisting of ethyl acrylate, butyl acrylate and ethylhexyl acrylate.

20. The composition of claim 19, wherein the anionic HASE polymer has 2 to 10 parts per hundred by weight of the first monomeric unit derived from a monomer of formula I:

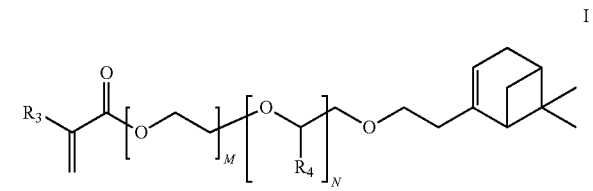

wherein, R4 is CH3 and M and N are each 0-200, wherein, M and N are each 0-50, but M and N cannot both be 0; and
0 to 10 parts per hundred by weight a mixture of C22, C16 and C18 linear alkyl chains.

21. The composition of claim 1, comprising 0.1 to 15 parts by weight anionic polymer and 0.1 to 15 parts by weight cationic polymer.

22. The composition of claim 1,
wherein the composition has a zeta potential at 25° C. in the range of 1 to 60 mV or −1 to −60 mV, or is a precursor convertible at a temperature of 100 to 250° C. to the composition having a zeta potential at 25° C. of 1 to 60 mV or −1 to −60 mV.

23. The composition of claim 10, wherein the composition has a zeta potential at 25° C. in the range of 14 to 50 mV or −14 to −50 mV.

24. The composition of claim 10, wherein the composition further comprises brine.

25. A treatment fluid for treating a subterranean formation comprising: the composition of claim 1 wherein the first polymer and the second polymer are each in an amount of from about 0.01 percent to about 1 percent by weight of the fluid, wherein water and dissolved salts in an amount of greater than 50 parts per thousand by weight of the fluid.

26. The treatment fluid of claim 25, further comprising proppant.

27. The treatment fluid of claim 25, further comprising a surfactant.

28. The treatment fluid of claim 25, further comprising at least one member of the group consisting of: crosslinking agents, buffering agents, breakers, tetraethylenepentamine, triethylenetetramine, pentaethylenehexamine, triethanolamine, sodium thiosulfate, alcohol, methanol, ethylene glycol, isopropanol, thiourea, sodium thiosulfate, co-solvents, acids, bases, buffers, chelating agents for the control of multivalent cations, freezing point depressants.

29. The treatment fluid of claim 25, further comprising at least one member selected from the group consisting of acids and gelling agents.

30. The treatment fluid of claim 25, wherein the acid is selected from the group consisting of hydrochloric acid, hydrofluoric acid, acetic acid, formic acid, citric acid, ethylene diamine tetra acetic acid ("EDTA"), glycolic acid, sulfamic acid, and combinations thereof; wherein the gelling agent is selected from at least one member of the group consisting of xanthan, polyacrylamide, scleroglucan and dilutan.

31. The treatment fluid of claim 25, comprising a breaker selected from at least one member of the group consisting of persulfates, ammonium persulfate, sodium persulfate, and potassium persulfate, bromates, sodium bromate, potassium bromate, periodates, metal peroxides, calcium peroxide, chlorites, sodium chlorite, hypochlorites, perborates, peroxides, enzymes, tert-butyl hydroperoxide, and tert-amyl hydroperoxide.

32. A personal care composition comprising, the composition of claim 1 and a personal care benefit agent.

33. A home care or industrial cleaning composition for cleaning fabrics or hard surfaces comprising, the composition of claim 1 and a surfactant and a home care or industrial cleaner benefit agent.

34. An aqueous coating composition, comprising:
(a) the composition of claim 1
(b) at least one pigment;
(c) water; and
(d) less than 5.0% by weight based on the total weight of the aqueous coating composition of anti-freeze agents; and
(e) optionally at least one latex polymer.

35. A composition for enhancing viscosity of a fluid comprising a mixture of:
(A) a first polymer having a weight average molecular weight of 35,000 to 10,000,000 selected from at least one member of the group consisting of:
(1) cationic polysaccharides with quaternized amino functional groups and cationic charge density of 0.3 to 2 milliequivalents/gram, wherein the cationic polysaccharide with a quaternized amino functionality of the composition consists of a cationically modified member selected from the group consisting of, glucomannan gums and their derivatives, guar gum, hydroxyethyl guar, hydroxypropyl guar, cellulose, hydroxypropyl cellulose, hydroxymethyl cellulose, hydroxyethyl cellulose, and combinations thereof.

(B) a second polymer having a weight average molecular weight of 30,000 g/mol to 10,000,000 g/mol selected from at least one member of the group consisting of:
HASE anionic polymers having an anionic charge density of 0.1 to 20 milliequivalents/gram, comprising:
(a) one or more first monomeric units, each independently comprising at least one bicycloheptyl-polyether, bicycloheptenyl-polyether per monomeric unit, wherein the bicycloheptyl-polyether or bicycloheptenyl-polyether group may optionally be substituted on one or more ring carbon atoms by one or two $(C_1\text{-}C_6)$alkyl groups per carbon atom, wherein the anionic HASE polymer has 2 to 10 parts per hundred by weight of the first monomeric unit derived from a monomer of formula I:

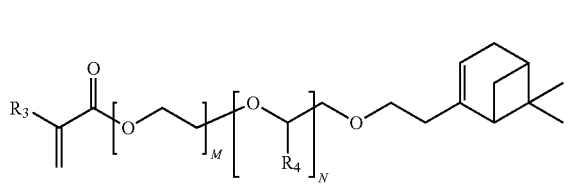

wherein, R4 is CH3 and M and N are each 0-200, wherein, M and N are each 0-50, but M and N cannot both be 0; and 0 to 10 parts per hundred by weight a mixture of C22, C16 and C18 linear alkyl chains; and (b) optionally one or more second monomeric units, each independently comprising at least one pendant linear or branched $(C_5\text{-}C_{50})$alkyl-polyether group per monomeric unit, provided that the first and second monomeric units cannot both comprise a branched $(C_5\text{-}C_{50})$alkyl-polyether group;

(c) at least one third monomeric unit independently comprising at least one acid monomeric unit, each acid monomeric unit independently comprising at least one member of the group consisting of a carboxylic acid-functional group, a sulfuric-acid functional group, a sulfonic acid-functional group, a phosphonic acid-functional group, and a phosphoric acid-functional group, wherein the third monomeric units are selected from the group consisting of acrylic acid groups, methacrylic acid groups, and mixtures thereof and (d) at least one fourth monomeric unit independently comprising at least one member of the group consisting of an alkyl group, hydroxyalkyl group, alkoxyalkyl group, cycloalkyl group, aryl group, aralkyl group, or aryloxy group, wherein the fourth monomeric units are selected from at least one member of the group consisting of ethyl acrylate, butyl acrylate and ethylhexyl acrylate;

wherein the composition has a zeta potential at 25° C. in the range of 14 to 60 mV or —0.5 to −100 mV.

36. The composition of claim 35, wherein the cationic polysaccharide is selected from the group consisting of guar gum, hydroxyethyl guar, hydroxypropyl guar, cellulose, hydroxypropyl cellulose, hydroxymethyl cellulose, hydroxyethyl cellulose and combinations thereof.

37. The composition of claim 36, wherein the cationic polysaccharide is a cationically modified member selected from the group consisting of hydroxypropyl guar, hydroxyethyl cellulose, and combinations thereof.

38. The composition of claim 37, wherein the HASE anionic polymer has said first, third, and fourth monomers but not said second monomer.

39. The composition of claim 38, wherein the composition has a zeta potential at 25° C. in the range of 14 to 50 mV or −14 to −50 mV.

40. The composition of claim 38, wherein the composition further comprises brine.

41. The composition of claim 38, wherein cationic polysaccharides of the first polymer consist of the cationic polysaccharides with quaternized amino functional groups and cationic charge density of 0.3 to 2 milliequivalents/gram, wherein the cationic polysaccharide with a quaternized amino functionality of the composition consists of a cationically modified member selected from the group consisting of, glucomannan gums and their derivatives, guar gum, hydroxyethyl guar, hydroxypropyl guar, cellulose, hydroxypropyl cellulose, hydroxymethyl cellulose, hydroxyethyl cellulose, and combinations thereof.

42. The composition of claim 38, wherein cationic polysaccharides of the first polymer consist of the cationic polysaccharides with quaternized amino functional groups selected from said cationically modified member of the group consisting of, guar gum, hydroxyethyl guar, hydroxypropyl guar, cellulose, hydroxypropyl cellulose, hydroxymethyl cellulose, hydroxyethyl cellulose, and combinations thereof.

* * * * *